United States Patent
Funyuu et al.

(10) Patent No.: US 9,051,246 B2
(45) Date of Patent: Jun. 9, 2015

(54) COMPOUND HAVING TRIMETHYLENE STRUCTURE, POLYMER COMPOUND CONTAINING UNIT THAT HAS TRIMETHYLENE STRUCTURE, AND REACTIVE COMPOUND HAVING TRIMETHYLENE STRUCTURE

(75) Inventors: Shigeaki Funyuu, Tsukuba (JP); Kenichi Ishitsuka, Tsukuba (JP); Hideo Nakako, Tsukuba (JP); Sentaro Okamoto, Yokohama (JP)

(73) Assignee: HITACHI CHEMICAL COMPANY, LTD. (JP)

( * ) Notice: Subject to any disclaimer, the term of this patent is extended or adjusted under 35 U.S.C. 154(b) by 0 days.

(21) Appl. No.: 13/575,943

(22) PCT Filed: Jan. 28, 2011

(86) PCT No.: PCT/JP2011/051799
§ 371 (c)(1),
(2), (4) Date: Jul. 27, 2012

(87) PCT Pub. No.: WO2011/093463
PCT Pub. Date: Aug. 4, 2011

(65) Prior Publication Data
US 2012/0289674 A1 Nov. 15, 2012

(30) Foreign Application Priority Data
Jan. 29, 2010 (JP) .................................. 2010-018744

(51) Int. Cl.
| | | |
|---|---|---|
| *C08G 79/08* | (2006.01) | |
| *C08G 77/00* | (2006.01) | |
| *C07C 33/24* | (2006.01) | |
| *C07C 33/46* | (2006.01) | |
| *C07C 43/164* | (2006.01) | |
| *C08G 61/02* | (2006.01) | |
| *C08G 61/12* | (2006.01) | |
| *C07C 33/48* | (2006.01) | |
| *C07C 69/65* | (2006.01) | |
| *C07C 25/24* | (2006.01) | |
| *C07F 5/02* | (2006.01) | |
| *C07F 7/18* | (2006.01) | |

(52) U.S. Cl.
CPC ............... *C07C 33/24* (2013.01); *C07C 33/46* (2013.01); *C07C 43/164* (2013.01); *C08G 61/02* (2013.01); *C08G 61/126* (2013.01); *C08G 2261/132* (2013.01); *C08G 2261/312* (2013.01); *C08G 2261/3142* (2013.01); *C08G 2261/3223* (2013.01); *C08G 2261/411* (2013.01); *C07C 33/486* (2013.01); *C07C 69/65* (2013.01); *C07C 25/24* (2013.01); *C07F 5/02* (2013.01); *C07F 7/1844* (2013.01)

(58) Field of Classification Search
CPC ................... C08G 2261/312; C08G 2261/411; C08G 61/126

USPC ......................................................... 528/8, 43
See application file for complete search history.

(56) References Cited

U.S. PATENT DOCUMENTS

| | | | | |
|---|---|---|---|---|
| 4,841,001 | A * | 6/1989 | Hawkins ........................ | 525/468 |
| 5,034,472 | A * | 7/1991 | Hawkins ........................ | 525/391 |
| 5,807,961 | A * | 9/1998 | Sawai et al. ................... | 528/170 |
| 2003/0136958 | A1 * | 7/2003 | Ong et al. ....................... | 257/40 |
| 2003/0164495 | A1 * | 9/2003 | Ong et al. ........................ | 257/40 |
| 2005/0288480 | A1 | 12/2005 | Marck et al. | |
| 2008/0015289 | A1 * | 1/2008 | Siripurapu ..................... | 524/115 |
| 2008/0311412 | A1 * | 12/2008 | Fokin et al. .................... | 428/457 |
| 2009/0127547 | A1 * | 5/2009 | Luebben et al. ................ | 257/40 |
| 2009/0326181 | A1 * | 12/2009 | Lens et al. ...................... | 528/25 |
| 2010/0168441 | A1 * | 7/2010 | Okamoto ....................... | 548/482 |
| 2010/0184942 | A1 * | 7/2010 | Chen et al. ..................... | 528/423 |

FOREIGN PATENT DOCUMENTS

| | | |
|---|---|---|
| CN | 100551902 C | 10/2009 |
| JP | 2005-154436 A | 6/2005 |

(Continued)

OTHER PUBLICATIONS

Watanabe et al. (Marcomolecules 2010, 43, 6562-6569).*

(Continued)

*Primary Examiner* — Liam J Heincer
(74) *Attorney, Agent, or Firm* — Fitch, Even, Tabin & Flannery

(57) ABSTRACT

A compound represented by a formula 1 shown below.

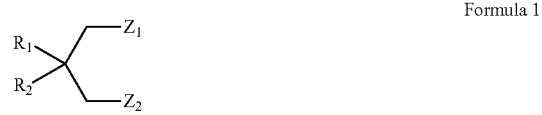

Formula 1

In the formula 1, each of R1 and R2 independently represents a group selected from the group consisting of a hydrogen atom and substituents composed of C, H and/or X (wherein X represents a hetero atom), and each of Z1 and Z2 independently represents a group selected from the group consisting of aromatic substituents composed of C and H, aromatic substituents composed of C, H and X (wherein X represents a hetero atom), groups containing an aromatic ring and a double-bonded and/or triple-bonded conjugated structure composed of C and H, and groups containing an aromatic ring and a double-bonded and/or triple-bonded conjugated structure composed of C, H and/or X (wherein X represents a hetero atom).

8 Claims, 3 Drawing Sheets

(56) References Cited

FOREIGN PATENT DOCUMENTS

| JP | 2005-258397 A | 9/2005 |
|----|---------------|--------|
| JP | 2005-534689 A | 11/2005 |
| WO | WO 02/088202 A | 11/2002 |
| WO | WO 2004/013086 A1 | 2/2004 |

OTHER PUBLICATIONS

W. Wang et al. "To Fold or to Assemble?" J. Am. Chem. Society, 2003, vol. 125, pp. 1120-1121.

F.D. Lewis et al., "Electronic Interactions in Tertiary Oligophenylureas," J. Phys. Chem. B, 2005, vol. 109, pp. 4893-4899.

Nakano et al., "Synthesis, Structure, and Photophysical and Electrochemical Properties of a π Stacked Polymer," J. Am. Chem. Soc., 2003, vol. 125, pp. 15474-15484.

D.A. Alonso et al. "π- Deficient α-arylsulfonyl Esters As Soft Nucleophiles in Organic Synthesis," Tetrahedron Letters, 42 (2001), pp. 8845-8848.

C.M. Lichtenfeld et al., "Carbolithiation of Cinnamyl Methyl Ethers and 2-Cinnamyl-2-methyl-1, 3-dioxolane: High Diastereoselectivity After Electrophilic Substitution," Tetrahedron, 55 (1999), pp. 2609-2624.

D.P. Nabar et al., Reactions of Organometallic Compounds With Conjugated Enol Ethers: Synthesis of β-Arylacrylates, Diarylmethylmalonates and Analogous Compounds, Bulletin of the Chemical Society of Japan, vol. 41, 1969, pp. 2991-2993.

J. Nishimura et al., "Efficient Intramolecular 2+2 Photocycloaddition of Styrene Derivatives Toward Cyclophanes," J. Am. Chem. Soc., 1987, vol. 109, pp. 5293-5295.

Staab et al., "Distance Dependence of Photoinduced Electron-Transfer: Syntheses and Structure of Naphthalene-Spacered Porphyrin-Quinone Cyclophanes," Liebigs Ann./Recueil, Nov. 1997, vol. 11, pp. 2321-2356.

Yamaguchi, Kentaro et al., "Aromatic Architecture. Use of the N-Methylamide Structure as a Molecular Splint," J. Am. Chem. Soc., vol. 113, 1991, pp. 5474-5475.

International Preliminary Report on Patentability, issued from the International Bureau, in corresponding International Application No. PCT/JP2011/051799, mailed Sep. 27, 2012, pp. 1-9.

Communication mailed May 20, 2014, in connection with Japanese Patent Application No. 2011-551938, 3 pages; Japanese Patent Office, Japan.

Office Action from State Intellectual Property Office of the P.R.C. in the corresponding Patent Application No. 201180007070.4 dated Apr. 23, 2014, 11 pages in Chinese and 7 pages in English Translation.

Kwon, Tae Woo et al., "Mass Spectra of 2-Substituted Diethyl Malonate Derivatives", Molecules, vol. 4, 1999, pp. 62-68.

Office Action from the Taiwan, Republic of China Patent Office in the corresponding Application No. 100103843, dated Mar. 19, 2014, 7 pages in Chinese, with 8 pages of its English translation.

Office Action in Taiwan Patent Appln. 100103843, issued Jan. 12, 2015.

Office Action in Chinese Patent Appln. 201180007070.4, issued Jan. 12, 2015.

* cited by examiner

COMPOUND HAVING TRIMETHYLENE STRUCTURE, POLYMER COMPOUND CONTAINING UNIT THAT HAS TRIMETHYLENE STRUCTURE, AND REACTIVE COMPOUND HAVING TRIMETHYLENE STRUCTURE

This application is a National Stage and claims the priority of International Application No. PCT/JP2011/051799, filed Jan. 28, 2011, which claims the priority from Japanese Patent Application No. 2010-018744 filed on Jan. 29, 2010, the content of which is hereby incorporated by reference into this application.

TECHNICAL FIELD

The present invention relates to a compound having a trimethylene structure within the molecule, a polymer compound containing a unit having a trimethylene structure within the molecule, a reactive compound having a trimethylene structure within the molecule, methods of producing the compound and the polymer compound using the reactive compound, and a composition and organic device containing the compound or the polymer compound.

BACKGROUND ART

Controlling the spatial arrangement of π-conjugated groups or π-conjugated molecules is an extremely important matter in the field of organic material development. In other words, the spatial interactions between π-conjugated groups or π-conjugated molecules has an effect on the optical properties, electrical properties, electrochemical properties or the like of organic materials, including the excimer emission and charge transfer of the material within solution or within a solid state.

By controlling the spatial arrangement to achieve a certain aligned arrangement of the π-conjugated groups or π-conjugated molecules, organic materials can be obtained that have favorable optical properties, electrical properties, electrochemical properties or the like that can be used within field effect transistors (FET), light emitting diodes (LED), solar cells, chemical sensors, biosensors, laser materials or the like. For this reason, molecular design and synthesis aimed at controlling the orientation and arrangement of π-conjugated groups or π-conjugated molecules by using methods of controlling molecular crystals, self-assembly and supramolecular chemistry has been the subject of active research. However, free arrangement and orientation of π-conjugated groups or π-conjugated molecules is still a distant goal.

On the other hand, three dimensional spatial control of polymer materials is attracting much attention as an effective means of controlling the arrangement of π-conjugated groups or π-conjugated molecules. A number of examples have been reported.

In the case of straight-chain polymers having π-conjugated groups within the main chain, the following reports have been disclosed regarding structures in which π-conjugated groups are stacked (π-stacked structures) and structures in which straight-chain polymers adopt a repeating folded structure.

Non-Patent Literature 1 discloses that an oligomer having perylene tetracarboxylic acid diimide as the π-conjugated groups, with these groups linked by comparatively long linking portions, adopts a repeating folded structure in solution. With this oligomer, a stabilized structure is obtained in which the perylene tetracarboxylic acid diimide groups that represent the π-conjugated groups adopt a continuous stacked structure (π-stacked structure).

Further, Non-Patent Literature 2 and Non-Patent Literature 3 disclose that tertiary diarylurea oligomers preferentially adopt a repeating folded structure within solution.

On the other hand, in relation to these reports, Non-Patent Literature 4 and Patent Literature 1 have reported examples of polymers that adopt a π-stacked structure in which the arrangement of substituent groups (pendants) bonded consecutively to the polymer main chain are controlled. In these Literatures, it was determined that in polymers prepared using 1,1-dibenzofulvene or a derivative thereof as a monomer, by selecting an appropriate polymerization method, the fluorene groups bonded consecutively to the polymer main chain folded and adopted a stacked arrangement. In this type of polymer, a shortening of the ultraviolet absorption wavelength and a lengthening of the fluorescence emission wavelength are observed as a result of the folding and stacking of the fluorene groups. Moreover, charge transfer measurement by laser excitation in the solid state confirms a high-speed charge transfer.

CITATION LIST

Patent Literature

Patent Literature 1: WO 02/088202

Non-Patent Literature

Non-Patent Literature 1: A. D. Q. Li et al., J. Am. Chem. Soc., 2003, vol. 125, pp. 1120 to 1121
Non-Patent Literature 2: K. Yamaguchi et al., J. Am. Chem. Soc., 1991, vol. 113, pp. 5474 to 5475
Non-Patent Literature 3: F. D. Lewis et al., J. Phs. Chem., B 2005, vol. 109, pp. 4893 to 4899
Non-Patent Literature 4: Nakano et al., J. Am. Chem. Soc., 2003, vol. 125, pp. 15474 to 15484

SUMMARY OF INVENTION

Technical Problem

An object of the present invention is to provide a compound that can adopt a π-stacked structure.

Further, another object of the present invention is to provide a polymer compound that can adopt a π-stacked structure.

Furthermore, yet another object of the present invention is to provide a reactive compound that can be used as a raw material for the above compound and the above polymer compound, and a method of producing the above compound or polymer compound using the reactive compound.

Moreover, yet another object of the present invention is to provide a composition and an organic device containing the above compound or the above polymer compound.

Solution to Problem

As a result of researching [(trimethylene-type linking portion)-(π-conjugated group)]$_n$ type polymer compounds having trimethylene-type linking portions, the inventors of the present invention discovered that when the trimethylene-type linking portion was a trimethylene derivative having a substituent on position-2 of the trimethylene structure, the polymer compound adopted a stacked structure in which the π-conjugated groups were stacked in a consecutive manner.

Further, they also discovered that, as a result of this stacked structure, the polymer compound exhibited unique properties, and they were thus able to complete the present invention.

In other words, the present invention relates to a compound represented by a formula 1 shown below.

[Chemical Formula 1]

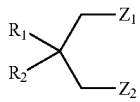

Formula 1

Embodiments of the compound of the present invention include, for example, the compounds described below.

A compound represented by a formula 2 shown below.

[Chemical Formula 2]

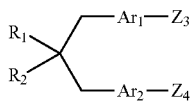

Formula 2

In the compounds shown above, each of R1 and R2 independently represents a group selected from the group consisting of a hydrogen atom and substituents composed of C, H and/or X (wherein X represents a hetero atom), each of Z1 to Z4 independently represents a group selected from the group consisting of aromatic substituents composed of C and H, aromatic substituents composed of C, H and X (wherein X represents a hetero atom), groups containing an aromatic ring and a double-bonded and/or triple-bonded conjugated structure composed of C and H, and groups containing an aromatic ring and a double-bonded and/or triple-bonded conjugated structure composed of C, H and/or X (wherein X represents a hetero atom), and each of Ar1 and Ar2 independently represents a group selected from the group consisting of divalent aromatic rings composed of C and H, and divalent aromatic rings composed of C, H and X (wherein X represents a hetero atom).

More specific embodiments of the compound of the present invention include the compounds described below.

The compound of any one of aforementioned compounds, wherein R1 is a hydrogen atom.

The compound of any one of aforementioned compounds, wherein R1 is a hydrogen atom and R2 is a carbon atom having not more than 2 hydrogen atoms bonded thereto.

The compound of any one of aforementioned compounds, wherein R1 is a hydrogen atom and R2 is a carbon atom having not more than 1 hydrogen atom bonded thereto.

The compound of any one of aforementioned compounds, wherein two or more of the aromatic rings within the compound adopt a stacked structure (a structure in which the aromatic rings overlap each other).

The compound of any one of aforementioned compounds, wherein the emission wavelength of the compound differs from the emission wavelengths for the stand-alone structures of Z1 to Z4, Ar1 or Ar2 contained within the compound.

Further, another aspect of the present invention relates to a polymer compound containing a unit represented by a formula 11 shown below.

[Chemical Formula 3]

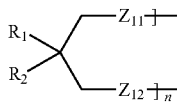

Formula 11

Furthermore, another aspect of the present invention relates a polymer compound containing a unit represented by a formula 12 shown below.

[Chemical Formula 4]

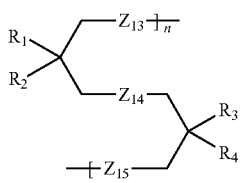

Formula 12

Embodiments of the polymer compound of the present invention include, for example, the polymer compounds described below.

A polymer compound containing a unit represented by a formula 3 shown below.

[Chemical Formula 5]

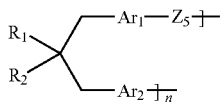

Formula 3

A polymer compound containing a unit represented by a formula 5 shown below.

[Chemical Formula 6]

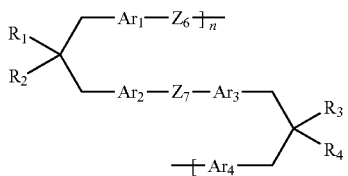

Formula 5

In the polymer compounds shown above, each of R1 to R4 independently represents a group selected from the group consisting of a hydrogen atom and substituents composed of C, H and/or X (wherein X represents a hetero atom), each of Z5 to Z7 and Z11 to Z15 independently represents a group selected from the group consisting of divalent aromatic rings composed of C and H, divalent aromatic rings composed of C, H and X (wherein X represents a hetero atom), divalent groups containing an aromatic ring and a double-bonded and/or triple-bonded conjugated structure composed of C and H, and divalent groups containing an aromatic ring and a double-bonded and/or triple-bonded conjugated structure composed of C, H and/or X (wherein X represents a hetero atom), each of Ar1 to Ar4 independently represents a group selected from the group consisting of divalent aromatic rings composed of C and H, and divalent aromatic rings composed of C, H and X (wherein X represents a hetero atom), and n represents an integer of 1 or greater.

More specific embodiments of the polymer compound of the present invention include the polymer compounds described below.

The polymer compound of any one of aforementioned polymer compounds, wherein the number-average molecular weight is within a range from 1,000 to 500,000.

The polymer compound of any one of aforementioned polymer compounds, wherein the number-average molecular weight is within a range from 2,500 to 100,000.

The polymer compound of any one of aforementioned polymer compounds, wherein R1 and R3 are hydrogen atoms.

The polymer compound of any one of aforementioned polymer compounds, wherein R1 and R3 are hydrogen atoms, and R2 and R4 are carbon atoms having not more than 2 hydrogen atoms bonded thereto.

The polymer compound of any one of aforementioned polymer compounds, wherein R1 and R3 are hydrogen atoms, and R2 and R4 are carbon atoms having not more than 1 hydrogen atom bonded thereto.

The polymer compound of any one of aforementioned polymer compounds, wherein two or more of the aromatic rings within the polymer compound adopt a stacked structure (a structure in which the aromatic rings overlap each other).

The polymer compound of any one of aforementioned polymer compounds, wherein the emission wavelength of the polymer compound differs from the emission wavelengths for the stand-alone structures of Z5 to Z7, Z11 to Z15, or Ar1 to Ar4 contained within the polymer compound.

Furthermore, another aspect of the present invention relates to a reactive compound represented by a formula 13 shown below.

[Chemical Formula 7]

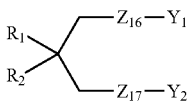

Formula 13

Further, another aspect of the present invention relates to a reactive compound represented by a formula 14 shown below.

[Chemical Formula 8]

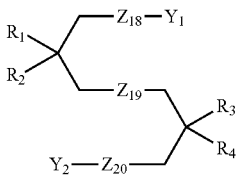

Formula 14

Embodiments of the reactive compound of the present invention include, for example, the reactive compounds described below.

A reactive compound represented by a formula 4 shown below.

[Chemical Formula 9]

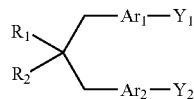

Formula 4

A reactive compound represented by a formula 7 shown below.

[Chemical Formula 10]

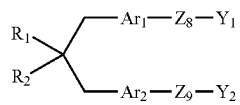

Formula 7

In the reactive compounds shown above, each of R1 to R4 independently represents a group selected from the group consisting of a hydrogen atom and substituents composed of C, H and/or X (wherein X represents a hetero atom), each of Z8, Z9 and Z16 to Z20 independently represents a group selected from the group consisting of divalent aromatic rings composed of C and H, divalent aromatic rings composed of C, H and X (wherein X represents a hetero atom), divalent groups containing an aromatic ring and a double-bonded and/or triple-bonded conjugated structure composed of C and H, and divalent groups containing an aromatic ring and a double-bonded and/or triple-bonded conjugated structure composed of C, H and/or X (wherein X represents a hetero atom), each of Ar1 and Ar2 independently represents a group selected from the group consisting of divalent aromatic rings composed of C and H, and divalent aromatic rings composed of C, H and X (wherein X represents a hetero atom), and each of Y1 and Y2 independently represents a functional substituent that participates in bond formation via a condensation reaction.

More specific embodiments of the reactive compound of the present invention include the compounds described below.

The reactive compound of any one of aforementioned reactive compounds, wherein R1 and R3 are hydrogen atoms.

The reactive compound of any one of aforementioned reactive compounds, wherein R1 and R3 are hydrogen atoms, and R2 and R4 are carbon atoms having not more than 2 hydrogen atoms bonded thereto.

The reactive compound of any one of aforementioned reactive compounds, wherein R1 and R3 are hydrogen atoms, and R2 and R4 are carbon atoms having not more than 1 hydrogen atom bonded thereto.

The reactive compound of any one of aforementioned reactive compounds, wherein two or more of the aromatic rings within the reactive compound adopt a stacked structure (a structure in which the aromatic rings overlap each other).

The reactive compound of any one of aforementioned reactive compounds, wherein the emission wavelength of the reactive compound differs from the emission wavelengths for the stand-alone structures of Z8, Z9, Z16 to Z20, Ar1 or Ar2 contained within the reactive compound.

Further, another aspect of the present invention relates to a method of producing a compound, the method including subjecting the reactive compound described above to a condensation reaction with a compound having one substituent that participates in the condensation reaction, thereby producing a compound represented by the formula 1 or formula 2 shown above.

Furthermore, another aspect of the present invention relates to a method of producing a polymer compound, the method including subjecting the reactive compound described above to a condensation reaction with the reactive compound and/or a compound having two substituents that participate in the condensation reaction, thereby producing a polymer compound containing at least one unit represented by the formula 11, the formula 12, the formula 3 or the formula 5 shown above.

Furthermore, another aspect of the present invention relates to a composition containing the aforementioned compound or the aforementioned polymer compound.

Furthermore, another aspect of the present invention relates to an organic device containing the aforementioned compound or the aforementioned polymer compound.

This application is related to the subject matter disclosed in prior Japanese Application 2010-18744 filed on Jan. 29, 2010, the entire contents of which are incorporated by reference herein.

Advantageous Effects of Invention

The present invention is able to provide a compound that adopts a π-stacked structure in which π-conjugated groups are stacked upon each other. Another aspect of the present invention can provide a polymer compound that adopts a π-stacked structure in which π-conjugated groups are stacked upon each other. Further, yet another aspect of the present invention can provide a reactive compound that can be used as a raw material for producing the above compound and polymer compound, and methods of efficiently producing the target compound or polymer compound using the reactive compound. Moreover, yet another aspect of the present invention can provide a composition or organic device which exhibits unique properties as a result of including the above compound or the above polymer compound having a π-stacked structure.

DESCRIPTION OF EMBODIMENTS

Figure 1:
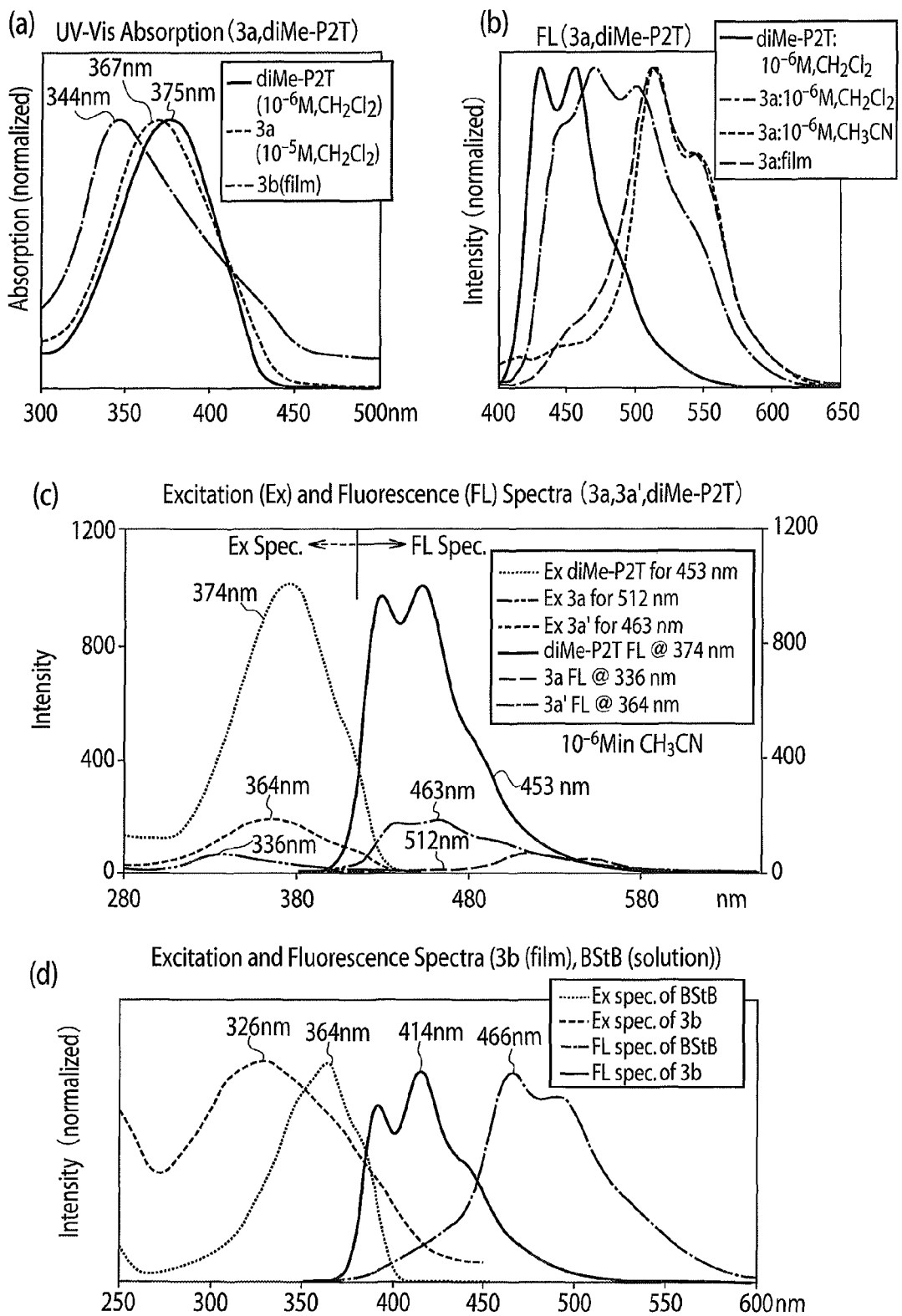
FIG. 1 illustrates the UV absorption spectrum (a) and emission spectra (b), (c) and (d) of a compound evaluated in an example 34.

<1> Compound Having a Trimethylene Structure within the Molecule (Trimethylene Compound Having a Substituent at Position-2)

The compound of the present invention is represented by a formula 1 shown below. In other words, the compound of the present invention is a compound having conjugated structure regions (π-conjugated groups) bonded to each other via a trimethylene structure (a trimethylene-type linking portion), wherein position-2 of the trimethylene structure has substituents R1 and R2.

[Chemical Formula 11]

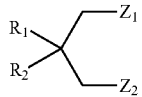

Formula 1

Moreover, in order to ensure preferential stacking of the conjugated structure regions (the π-conjugated groups Z1 and Z2) in the above formula 1, thereby predominantly obtaining optical properties, electrical properties, electrochemical properties or the like that are difficult to obtain with the stand-alone π-conjugated groups, a structure represented by a formula 2 shown below, in which groups Ar1 and Ar2 selected from the group consisting of divalent aromatic rings composed of C and H, and divalent aromatic rings composed of C, H and X (wherein X represents a hetero atom) are bonded to the trimethylene structure, is particularly preferred. The term "stand-alone π-conjugated group" describes the compound corresponding with the π-conjugated group, or more specifically, the compound obtained by adding a hydrogen atom to the π-conjugated group.

[Chemical Formula 12]

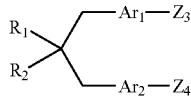

Formula 2

In the formula 1 and the formula 2, each of R1 and R2 independently represents a group selected from the group consisting of a hydrogen atom and substituents composed of C, H and/or X (wherein X represents a hetero atom), each of Z1 to Z4 independently represents a group selected from the group consisting of aromatic substituents composed of C and H, aromatic substituents composed of C, H and X (wherein X represents a hetero atom), groups containing an aromatic ring and a double-bonded and/or triple-bonded conjugated structure composed of C and H, and groups containing an aromatic ring and a double-bonded and/or triple-bonded conjugated structure composed of C, H and/or X (wherein X represents a hetero atom), and each of Ar1 and Ar2 independently represents a group selected from the group consisting of divalent aromatic rings composed of C and H, and divalent aromatic rings composed of C, H and X (wherein X represents a hetero atom).

Z1 to Z4 may have a non-conjugated region. Z1 to Z4 may include two or more different types of groups selected from among the groups described above. R1 and R2 can not both be hydrogen atoms.

Further, C represents a carbon atom and H represents a hydrogen atom. Examples of X include O (an oxygen atom), N (a nitrogen atom), S (a sulfur atom), Si (a silicon atom) and halogen atoms.

R1 and R2 are described below.

R1 and R2 are each selected from among a hydrogen atom and substituents composed of C, H and/or X. Examples of the substituents composed of C, H and/or X include aliphatic substituents composed of C and H, aromatic substituents composed of C and H, aromatic substituents composed of C, H and X, and other substituents composed of C, H and/or X (including aliphatic substituents).

Examples of the aliphatic substituents composed of C and H include linear and branched alkyl groups of 1 to 12 carbon atoms, cycloalkyl groups of 1 to 12 carbon atoms, alkenyl groups of 1 to 12 carbon atoms, and alkynyl groups of 1 to 12 carbon atoms.

Examples of the aromatic substituents composed of C and H include aryl groups, arylalkyl groups, arylalkenyl groups, arylalkynyl groups, polycyclic aryl groups such as a biphenylyl group, and condensed-ring aryl groups such as a naphthyl group or anthracenyl group, which may have a linear or branched alkyl group of 1 to 12 carbon atoms, a cycloalkyl group of 1 to 12 carbon atoms or the like as a substituent.

Examples of the aromatic substituents composed of C, H and X include aryloxy groups, arylthio groups, arylalkoxy groups, arylalkylthio groups, thienyl group, pyrrolyl group, furyl group, pyridyl group, piperidyl group, quinolyl group and isoquinolyl group, which may have a linear or branched alkyl group of 1 to 12 carbon atoms, a cycloalkyl group of 1 to 12 carbon atoms, an alkoxy group of 1 to 12 carbon atoms or the like as a substituent.

More specific examples of the other substituents composed of C, H and/or X (including aliphatic substituents) include substituents composed of C, H and X, substituents composed of C and X, substituents composed of H and X, and substituents composed of X.

Specific examples of the substituents composed of C, H and/or X include alkoxy groups, alkylthio groups, hydroxyl group, hydroxyalkyl groups, amino group, substituted amino groups, silyl group, substituted silyl groups, silyloxy group, substituted silyloxy groups, halogen atoms, acyl groups, acyloxy groups, imino group, amide group, imide group, carboxyl group, substituted carboxyl groups, cyano group, and alkyl groups having one of these substituents.

R1 and R2 may have a substituent, and examples of the substituent include substituents composed of C, H and/or X.

In order to ensure preferential stacking of the conjugated structure regions, thereby predominantly obtaining optical properties, electrical properties, electrochemical properties or the like that are difficult to obtain with the stand-alone π-conjugated groups, a compound in which R1 is a hydrogen atom is preferred, and a compound in which R1 is a hydrogen atom and R2 is a carbon atom having not more than 2 hydrogen atoms bonded thereto is more preferred. Moreover, a compound in which R1 is a hydrogen atom and R2 is a carbon atom having not more than 1 hydrogen atom bonded thereto is still more preferred, and a compound in which R1 is a hydrogen atom and R2 is a carbon atom having no hydrogen atoms bonded thereto is the most desirable.

In the present invention, the expression that "R2 is a carbon atom having not more than 2 hydrogen atoms (or not more than one hydrogen atom, or no hydrogen atoms) bonded thereto" means that R2 is a substituent having a free carbon atom, wherein the number of hydrogen atoms bonded to the free carbon atom is not more than 2. In other words, R2 is a monovalent group having a free valency on the carbon atom (the carbon atom bonded to the trimethylene structure), in which the number of hydrogen atoms bonded to the carbon atom is not more than 2.

For example, comparing the R2 groups represented by the formulas shown below, (b) to (d) are preferred, (c) and (d) are more preferred, and (d) is the most desirable.

[Chemical Formula 13]

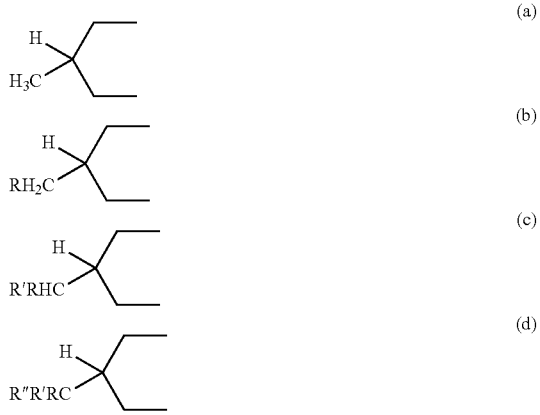

In these formulas, RH$_2$C—, R'RHC— and R"R'RC— can each be selected from among the substituents composed of C, H and/or X. Further, RH$_2$C—, R'RHC— and R"R'RC— may form a cyclic structure.

Z1 to Z4 (Zn (wherein n=1 to 4)) are described below.

Examples of the aromatic substituents composed of C and H include aryl groups, arylalkyl groups, arylalkenyl groups, arylalkynyl groups, polycyclic aryl groups such as a biphenylyl group, and condensed-ring aryl groups such as a naphthyl group or anthracenyl group, which may have a linear or branched alkyl group of 1 to 12 carbon atoms, a cycloalkyl group of 1 to 12 carbon atoms or the like as a substituent. Additional examples include monovalent aromatic rings obtained by adding a hydrogen atom to the divalent aromatic rings composed of C and H described below for Ar1 and Ar2.

Examples of the aromatic substituents composed of C, H and X (wherein X represents a hetero atom) include aryloxy groups, arylthio groups, arylalkoxy groups, arylalkylthio groups, thienyl group, pyrrolyl group, furyl group, pyridyl group, piperidyl group, quinolyl group and isoquinolyl group, which may have a linear or branched alkyl group of 1 to 12 carbon atoms, a cycloalkyl group of 1 to 12 carbon atoms, an alkoxy group of 1 to 12 carbon atoms or the like as a substituent. Additional examples include monovalent aromatic rings obtained by adding a hydrogen atom to the divalent aromatic rings composed of C, H and X described below for Ar1 and Ar2.

Examples of the groups containing an aromatic ring and a double-bonded and/or triple-bonded conjugated structure composed of C and H include groups containing an aromatic ring and a carbon-carbon double-bonded and/or carbon-carbon triple-bonded conjugated structure. Examples of the carbon-carbon double-bonded conjugated structure include an ethenyl group and a propenyl group, whereas examples of the carbon-carbon triple-bonded conjugated structure include an ethynyl group and a propynyl group.

Examples of the groups containing an aromatic ring and a double-bonded and/or triple-bonded conjugated structure composed of C, H and/or X (wherein X represents a hetero atom) include groups containing an aromatic ring, together with a double-bonded and/or triple-bonded conjugated structure composed of C, H and X, a double-bonded and/or triple-bonded conjugated structure composed of C and X, or a double-bonded and/or triple-bonded conjugated structure composed of H and X. More specific examples of the groups containing an aromatic ring and a double-bonded and/or triple-bonded conjugated structure composed of C, H and/or X (wherein X represents a hetero atom) include groups containing an aromatic ring and a conjugated structure such as an imino group.

Examples of the aromatic ring in Zn include aromatic rings composed of C and H, and aromatic rings composed of C, H and X (wherein X represents a hetero atom). More specific examples of these aromatic rings composed of C and H, and aromatic rings composed of C, H and X (wherein X represents a hetero atom) include the same aromatic rings as the divalent aromatic rings composed of C and H, and the divalent aromatic rings composed of C, H and X (wherein X represents a hetero atom) described below for Ar1 and Ar2 (although the ring may be a monovalent aromatic ring in some cases).

Zn may be composed of any one of the groups described above, or may be composed of two or more identical or different groups selected from among these groups. In other words, Zn may be a group in which, for example, 2 to 20, 2 to 10, or 2 to 5, identical or different groups selected from among the groups described above are linked together.

Zn is preferably a group having a broad π-surface, and in this regard, the use of a condensed ring is preferable.

Ar1 and Ar2 are described below.

Examples of the divalent aromatic rings composed of C and H include aromatic hydrocarbon rings such as divalent monocyclic rings or divalent condensed rings in which at least 2, and preferably 2 to 5, rings are condensed. Specific examples include aromatic hydrocarbon rings such as a divalent benzene ring, naphthalene ring, anthracene ring, phenanthrene ring, pyrene ring, perylene ring, tetracene ring, pentacene ring, fluorene ring, indenofluorene ring, azulene ring, heptalene ring, biphenylene ring, indacene ring, acenaphthylene ring, phenalene ring, fluoranthene ring, acephenanthrylene ring, aceanthrylene ring, triphenylene ring, chrysene ring, naphthacene ring, picene ring, pentaphene ring, tetraphenylene ring, hexaphene ring, hexacene ring, rubicene ring, coronene ring, trinaphthylene ring, heptaphene ring or heptacene ring.

Examples of the divalent aromatic rings composed of C, H and X (wherein X represents a hetero atom) include heterocyclic aromatic rings such as divalent monocyclic heterocyclic rings or divalent condensed rings in which at least 2, and preferably 2 to 5, rings are condensed. Specific examples include heterocyclic aromatic rings such as a divalent pyridine ring, pyrimidine ring, pyridazine ring, pyrazine ring, quinoline ring, isoquinoline ring, quinoxaline ring, quinazoline ring, acridine ring, phenanthroline ring, thiophene ring, benzothiophene ring, dibenzothiophene ring, thiophene oxide ring, benzothiophene oxide ring, dibenzothiophene oxide ring, thiophene dioxide ring, benzothiophene dioxide ring, dibenzothiophene dioxide ring, furan ring, benzofuran ring, dibenzofuran ring, pyrrole ring, indole ring, dibenzopyrrole ring, silole ring, benzosilole ring, dibenzosilole ring, borole ring, benzoborole ring, dibenzoborole ring, pyrazole ring, imidazole ring, oxadiazole ring, carbazole ring, pyrroloimidazole ring, pyrrolopyrazole ring, pyrrolopyrrole ring, thienopyrrole ring, thienothiophene ring, furopyrrole ring, furofuran ring, thienofuran ring, benzisooxazole ring, benzisothiazole ring, benzimidazole ring, triazine ring, cinnoline ring, phenanthridine ring, perimidine ring, quinazolinone ring, isobenzofuran ring, isoindole ring, indolizine ring, chromene ring, benzopyran ring, xanthene ring, quinolizine ring, phenanthyridine ring, naphthyridine ring, indazole ring, phthalazine ring, purine ring, pteridine ring, thianthrene ring, phenoxathiin ring, phenoxazine ring, phenothiazine ring or phenazine ring.

Among the above possibilities for Ar1 and Ar2, aromatic hydrocarbon rings are preferable, and a benzene ring, naphthalene ring and anthracene ring are particularly preferable.

Further, Ar1 and Ar2 are preferably groups having a broad π-surface, and in this regard, the use of condensed rings is preferable.

The groups of Zn, Ar1 and Ar2 may have a substituent, and examples of the substituent include an alkyl group, alkoxy group, alkylthio group, aryl group, aryloxy group, arylthio group, arylalkyl group, arylalkoxy group, arylalkylthio group, arylalkenyl group, arylalkynyl group, hydroxyl group, hydroxyalkyl group, amino group, substituted amino group, silyl group, substituted silyl group, silyloxy group, substituted silyloxy group, halogen atom, acyl group, acyloxy group, imino group, amide group, imide group, carboxyl group, substituted carboxyl group, cyano group or monovalent heterocyclic group.

The compound of the present invention may adopt a stacked structure in which two or more aromatic rings within the compound are stacked. Further, the emission wavelength of the compound of the present invention differs from the emission wavelength of the stand-alone aromatic rings within the compound. For example, the emission wavelength of the compound represented by the above formula 1 differs from the emission wavelength of the stand-alone form of Z1 or Z2, and the emission wavelength of the compound represented by the above formula 2 differs from the emission wavelength of the stand-alone form of Z3, Z4, Ar1 or Ar2. In other words, the absorption coefficient attributable to the aromatic rings of the compound of the present invention is smaller than the absorption coefficient corresponding with the substituents used for introducing the aromatic rings (Z1 or Z2 in the compound represented by the formula 1, or Z3, Z4, Ar1 or Ar2 in the compound represented by the formula 2). As a result, the compound can be used as an ultraviolet-transparent material, and is also useful as a light-resistant material.

<2> Polymer Compound Containing a Unit Having a Trimethylene Structure within the Molecule (Polymer Compound Having a Trimethylene-Type Linking Portion)

The polymer compound of the present invention is a polymer compound containing a unit having conjugated structure regions (π-conjugated groups) bonded to each other via a trimethylene structure (a trimethylene-type linking portion), wherein position-2 of the trimethylene structure has substituents R1 and R2. The polymer compound of the present invention is described below.

One aspect of the polymer compound of the present invention is a polymer compound containing a unit represented by a formula 11 shown below.

[Chemical Formula 14]

Formula 11

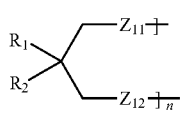

Examples of the polymer compound of the present invention include a polymer compound containing a unit represented by a formula 3 shown below.

[Chemical Formula 15]

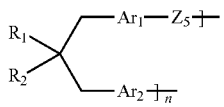

Formula 3

Further, examples of the polymer compound of the present invention include a polymer compound containing at least one of the units represented by a formula 9 shown below.

[Chemical Formula 16]

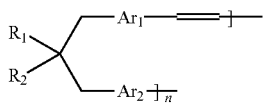

Formula 9

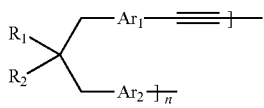

Moreover, examples of the polymer compound of the present invention include a polymer compound containing a unit represented by a formula 6 shown below.

[Chemical Formula 17]

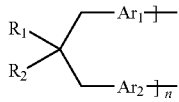

Formula 6

Furthermore, another aspect of the polymer compound of the present invention is a polymer compound containing a unit represented by a formula 12 shown below.

[Chemical Formula 18]

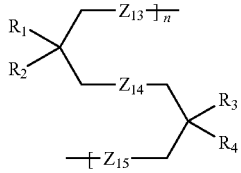

Formula 12

Examples of the polymer compound of the present invention include a polymer compound containing a unit represented by a formula 5 shown below.

[Chemical Formula 19]

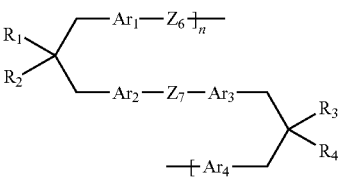

Formula 5

In the formulas 11, 3, 9, 6, 12 and 5:

each of R1 to R4 independently represents a group selected from the group consisting of a hydrogen atom and substituents composed of C, H and/or X (wherein X represents a hetero atom), each of Z5 to Z7 and Z11 to Z15 independently represents a group selected from the group consisting of divalent aromatic rings composed of C and H, divalent aromatic rings composed of C, H and X (wherein X represents a hetero atom), divalent groups containing an aromatic ring and a double-bonded and/or triple-bonded conjugated structure composed of C and H, and divalent groups containing an aromatic ring and a double-bonded and/or triple-bonded conjugated structure composed of C, H and/or X (wherein X represents a hetero atom), each of Ar1 to Ar4 independently represents a group selected from the group consisting of divalent aromatic rings composed of C and H, and divalent aromatic rings composed of C, H and X (wherein X represents a hetero atom), and n represents an integer of 1 or greater.

Z5 to Z7 and Z11 to Z15 may have a non-conjugated region. Z5 to Z7 and Z11 to Z15 may include two or more different types of groups selected from among the groups described above. R1 and R2 can not both be hydrogen atoms, and R3 and R4 can not both be hydrogen atoms.

Further, C represents a carbon atom and H represents a hydrogen atom. Examples of X include O (an oxygen atom), N (a nitrogen atom), S (a sulfur atom), Si (a silicon atom) and halogen atoms.

The polymer compound of the present invention may be a homopolymer or a copolymer. The copolymer may be an alternating, random, block or graft copolymer. The polymer compound of the present invention may be a polymer composed solely of the units represented by the above formulas, or may be a polymer compound containing a unit represented by one of the above formulas together with another repeating unit.

In the polymer compound of the present invention, the proportion of the unit represented by one of the above formulas is preferably within a range from 10 to 100% in terms of the monomer charge ratio, and in terms of ensuring that a stacked structure is adopted efficiently, a proportion of 25 to 100% is particularly preferred. The monomer charge ratio refers to the ratio (number of mols of monomer that gives rise to the unit represented by the above formula)/(total number of mols of monomers).

In those cases where the polymer compound of the present invention is composed solely of one type of repeating unit, the polymer compound of the present invention can be represented by one of the above formulas (wherein n in the formula is 2 or greater). From the viewpoint of obtaining optical properties, electrical properties, electrochemical properties or the like that are difficult to obtain with a monomer having the π-conjugated groups, n is preferably within a range from 3 to 500, and more preferably from 4 to 100. Here, "the monomer having the π-conjugated groups" refers to the monomer used in producing the polymer compound of the present invention, or a compound that corresponds with the repeating unit that constitutes the polymer compound of the present invention.

Examples of R1 to R4 and Ar1 to Ar4 include the same groups as those described above in relation to the compound represented by the formula 1 or formula 2. Further, examples of preferred groups for R1 to R4 and Ar1 to Ar4 include the same groups as the preferred groups described above in relation to the compound represented by the formula 1 or formula 2.

In order to ensure that the polymer compound preferentially adopts a stacked structure, thereby predominantly obtaining optical properties, electrical properties, electrochemical properties or the like that are difficult to obtain with a monomer having the π-conjugated groups, or with stand-alone aromatic rings or stand-alone combinations of an aromatic ring and a double-bonded and/or triple-bonded conjugated structure region, in terms of R1 and R2, a polymer compound in which R1 is a hydrogen atom is preferable, a polymer compound in which R1 is a hydrogen atom and R2 is a carbon atom having not more than 2 hydrogen atoms bonded thereto is more preferable, a polymer compound in which R1 is a hydrogen atom and R2 is a carbon atom having not more than 1 hydrogen atom bonded thereto is still more preferable, and a compound in which R1 is a hydrogen atom and R2 is a carbon atom having no hydrogen atoms bonded thereto is the most desirable. Similar, in terms of R3 and R4, a polymer compound in which R3 is a hydrogen atom is preferable, a polymer compound in which R3 is a hydrogen atom and R4 is a carbon atom having not more than 2 hydrogen atoms bonded thereto is more preferable. Moreover, a polymer compound in which R3 is a hydrogen atom and R4 is a carbon atom having not more than 1 hydrogen atom bonded thereto is still more preferable, and a compound in which R3 is a hydrogen atom and R4 is a carbon atom having no hydrogen atoms bonded thereto is the most desirable.

Z5 to Z7 and Z11 to Z15 (Zn (wherein n=5 to 7 and 11 to 15)) are described below.

Zn represents a group selected from the group consisting of divalent aromatic rings composed of C and H, divalent aromatic rings composed of C, H and X (wherein X represents a hetero atom), divalent groups containing an aromatic ring and a double-bonded and/or triple-bonded conjugated structure composed of C and H, and divalent groups containing an aromatic ring and a double-bonded and/or triple-bonded conjugated structure composed of C, H and/or X (wherein X represents a hetero atom). Zn may have a non-conjugated region.

Examples of the divalent groups containing an aromatic ring and a double-bonded and/or triple-bonded conjugated structure composed of C and H include divalent groups containing an aromatic ring and a carbon-carbon double-bonded and/or carbon-carbon triple-bonded conjugated structure. Examples of the carbon-carbon double-bonded conjugated structure include an ethenylene group, whereas examples of the carbon-carbon triple-bonded conjugated structure include an ethynylene group.

Examples of the divalent groups containing an aromatic ring and a double-bonded and/or triple-bonded conjugated structure composed of C, H and/or X (wherein X represents a hetero atom) include groups containing an aromatic ring, together with a double-bonded and/or triple-bonded conjugated structure composed of C, H and X, a double-bonded and/or triple-bonded conjugated structure composed of C and X, or a double-bonded and/or triple-bonded conjugated structure composed of H and X.

In the divalent groups containing an aromatic ring and a double-bonded and/or triple-bonded conjugated structure composed of C and H, and the divalent groups containing an aromatic ring and a double-bonded and/or triple-bonded conjugated structure composed of C, H and/or X (wherein X represents a hetero atom), examples of the aromatic ring include divalent aromatic rings composed of C and H, and divalent aromatic rings composed of C, H and X (wherein. X represents a hetero atom).

Examples of the aromatic rings for Zn include the same groups as those used for Ar1 and Ar2 in the compound represented by the above formula 2.

Zn may be composed of any one of the groups described above, or may be composed of two or more identical or different groups selected from among these groups. For example, Zn may be a group in which, for example, 2 to 20, 2 to 10, or 2 to 5, identical or different groups selected from among the groups described above are linked together. Further, Zn may have the same substituents as those described above for the substituents which Zn may have in the compounds represented by the above formulas 1 and 2. Zn is preferably a group having a broad π-surface, and in this regard, the use of a condensed ring is preferable.

In order to ensure that the polymer compound preferentially adopts a stacked structure, thereby predominantly obtaining optical properties, electrical properties, electrochemical properties or the like that are difficult to obtain with a monomer having the π-conjugated groups, or with stand-alone aromatic rings or stand-alone combinations of an aromatic ring and a double-bonded and/or triple-bonded conjugated structure region, Zn is preferably a structure shown below.

[Chemical Formula 20]

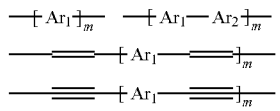

In the above formulas, m represents an integer of 1 or greater. From the viewpoint of achieving optical properties, electrical properties or electrochemical properties that are difficult to obtain with a monomer having the π-conjugated groups, m is preferably 1 to 10, and more preferably 1 to 3. Further, examples of Ar1 and Ar2 in the above formulas include the same groups as those described above in relation to the compound represented by the formula 2.

The number-average molecular weight of the polymer compound of the present invention is preferably within a range from 1,000 to 500,000. In order to improve the handling of the polymer compound, and predominantly achieve the optical properties, electrical properties or electrochemical properties attributable to the stacked structure of the aromatic rings of the polymer compound, the number-average molecular weight is more preferably within a range from 2,500 to 100,000. The number-average molecular weight can be measured by gel permeation chromatography (GPC) using a calibration curve of standard polystyrenes.

In the polymer compound of the present invention, two or more aromatic rings within the polymer compound can adopt a stacked structure. Further, the emission wavelength of the polymer compound of the present invention differs from the emission wavelength of the stand-alone aromatic rings within the polymer compound or the emission wavelength of a monomer having the π-conjugated groups. For example, taking a compound containing a unit represented by the above formula 3 as an example of the polymer compound of the present invention, the emission wavelength of the compound containing the unit represented by the formula 3 differs from the emission wavelengths of Z5, Ar1 and Ar2 in their respective stand-alone forms, and differs from the emission wavelength of a compound composed solely of the unit represented by the formula 3. In other words, the absorption coefficient attributable to the aromatic rings of the polymer compound of the present invention is smaller than the absorption coefficient corresponding with the substituents used for introducing the aromatic rings (such as Z5, Ar1 or Ar2 in the case of a compound containing a unit represented by the formula 3). As a result, the polymer compound can be used as an ultraviolet-transparent material, and is also useful as a light-resistant material.

<3> Reactive compound having a trimethylene structure within the molecule

The reactive compound having a trimethylene structure of the present invention can be used in the production of the compound and polymer compound of the present invention.

One aspect of the reactive compound of the present invention is a reactive compound represented by a formula 13 shown below.

[Chemical Formula 21]

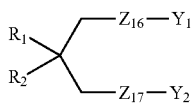

Formula 13

Examples of the reactive compound of the present invention include reactive compounds represented by a formula 4 shown below.

[Chemical Formula 22]

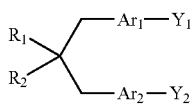

Formula 4

Further, examples of the reactive compound of the present invention include reactive compounds represented by a formula 7 shown below.

[Chemical Formula 23]

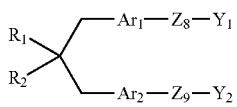

Formula 7

Moreover, examples of the reactive compound of the present invention include reactive compounds represented by one of the formulas 8 shown below.

[Chemical Formula 24]

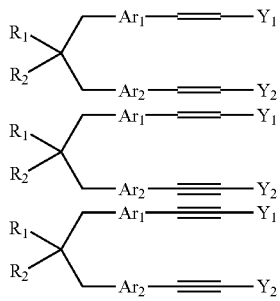

Formula 8

Further, another aspect of the reactive compound of the present invention is a reactive compound represented by a formula 14 shown below.

[Chemical Formula 25]

Formula 14

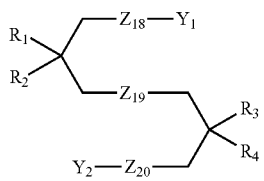

Examples of the reactive compound of the present invention include reactive compounds represented by a formula 10 shown below.

[Chemical Formula 26]

Formula 10

In the above formulas 13, 4, 7, 8, 14 and 10:

each of R1 to R4 independently represents a group selected from the group consisting of a hydrogen atom and substituents composed of C, H and/or X (wherein X represents a hetero atom), each of Z8 to Z10 and Z16 to Z20 independently represents a group selected from the group consisting of divalent aromatic rings composed of C and H, divalent aromatic rings composed of C, H and X (wherein X represents a hetero atom), divalent groups containing an aromatic ring and a double-bonded and/or triple-bonded conjugated structure composed of C and H, and divalent groups containing an aromatic ring and a double-bonded and/or triple-bonded conjugated structure composed of C, H and/or X (wherein X represents a hetero atom), each of Ar1 to Ar4 independently represents a group selected from the group consisting of divalent aromatic rings composed of C and H, and divalent aromatic rings composed of C, H and X (wherein X represents a hetero atom), and each of Y1 and Y2 independently represents a functional substituent that participates in bond formation via a condensation reaction.

Z8 to Z10 and Z16 to Z20 may have a non-conjugated region. Z8 to Z10 and Z16 to Z20 may include two or more different types of groups selected from among the groups described above. R1 and R2 can not both be hydrogen atoms, and R3 and R4 can not both be hydrogen atoms. Here, the term "condensation reaction" includes coupling reactions.

Further, C represents a carbon atom and H represents a hydrogen atom. Examples of X include O (an oxygen atom), N (a nitrogen atom), S (a sulfur atom), Si (a silicon atom) and halogen atoms.

In the reactive compound represented by the above formulas, examples of R1 to R4, Ar1 to Ar4 and Zn (wherein n=8 to 10 and 16 to 20) include the same groups as those described above for R1 to R4, Ar1 to Ar4 and Zn in relation to the aforementioned compound and polymer compound. Further, examples of preferred groups for R1 to R4, Ar1 to Ar4 and Zn (wherein n=8 to 10 and 16 to 20) include the same groups as the preferred groups described above in relation to the aforementioned compound and polymer compound.

Y1 and Y2 are described below.

Examples of Y1 and Y2 (functional substituents that participate in bond formation via a condensation reaction) include halogen atoms, alkyl sulfonate groups, aryl sulfonate groups, aryl alkyl sulfonate groups, borate ester groups, sulfonium methyl groups, phosphonium methyl groups, phosphonate methyl groups, methyl monohalide groups, as well as a boric acid group, formyl group, cyanomethyl group, vinyl group, ethynyl group, carboxyl group, ester groups and amide group. Examples of the alkyl sulfonate groups include a methane sulfonate group, ethane sulfonate group and trifluoromethane sulfonate group, examples of the aryl sulfonate groups include a benzene sulfonate group and p-toluene sulfonate group, and examples of the aryl alkyl sulfonate groups include a benzyl sulfonate group.

Examples of preferred substituents for the functional substituent that participates in bond formation via a condensation reaction vary depending on the type of polymerization reaction, and for example, in those cases where a zero-valent nickel complex is used, such as the Kumada-Tamao coupling reaction, a halogen atom, alkyl sulfonate group, aryl sulfonate group or aryl alkyl sulfonate group is preferred. Further, in those cases where a nickel catalyst or a palladium catalyst is used, such as the Suzuki coupling reaction, a halogen atom, borate ester group, boric acid group or the like is preferred.

The reactive compound of the present invention can be obtained using the two methods (a) and (b) described below. The following description takes the reactive compound represented by the above formula 4 as an example.

(a) Route Using a Malonate Diester as a Raw Material

The reactive compound of the present invention can be obtained using a malonate diester or a derivative thereof as a raw material, by performing an alkylation with an alkylating agent X—CH$_2$—Ar1-Y1 and/or X—CH$_2$—Ar2-Y2 (X=halogen), followed by a decarboxylation reaction. Moreover, the reactive compound of the present invention can also be produced using synthesis methods that use either the α,α-dialkylated malonate diester obtained upon alkylation of the malonate diester, or the α,α-dialkylacetate ester obtained upon decarboxylation, as a reaction intermediate. The reaction for obtaining the reactive compound from a malonate diester or a derivative thereof, and the reaction relating to the substituents R1 and R2 of the reactive compound are described below.

Using a malonate diester as a raw material, reaction with X—CH$_2$—Ar1-Y1 (X=halogen) under basic conditions causes either monoalkylation that yields a monoalkyl product or dialkylation (when Ar1=Ar2, Y1=Y2) that yields a dialkyl product (reactive compound). In the case of monoalkylation, a second alkylation reaction with X—CH$_2$—Ar2-Y2 (X=halogen) under basic conditions yields a dialkyl product (reactive compound).

One of the ester groups of the obtained dialkyl product (α,α-dialkylated malonate diester or derivative thereof) may be decomposed and decarboxylated to obtain a monoester (reactive compound). Further, the thus obtained monoester may be subjected to an addition reaction with an excess of a Grignard reagent or an alkyllithium reagent to form a tertiary alcohol (reactive compound). Moreover, the thus obtained tertiary alcohol (reactive compound) may be further reacted under basic conditions, either by alkylation to form an alkoxy compound (reactive compound) or by silylation to form a silyloxy compound (reactive compound).

By appropriately altering the X—CH$_2$—Ar1-Y1 or X—CH$_2$—Ar2-Y2 reacted with the malonate diester, Ar1, Ar2, Y1 and Y2 within the reactive compound represented by the above formula 4 can be altered to the desired groups. Specifically, by derivatizing Y1 and Y2 in X—CH$_2$—Ar1-Y1 and X—CH$_2$—Ar2-Y2, the desired functional substituents can be introduced into the reactive compound.

(b) Route Using an Acetoacetate Ester as a Raw Material

The reactive compound of the present invention can be obtained using an acetoacetate ester or a derivative thereof as a raw material, by performing an alkylation with an alkylating agent X—CH$_2$—Ar1-Y1 and/or X—CH$_2$—Ar2-Y2 (X=halogen), followed by a decarboxylation reaction. Moreover, the reactive compound of the present invention can also be produced using synthesis methods that use either the α,α-dialkylated acetoacetate ester obtained upon alkylation, or the α,α-dialkyl ketone obtained upon decarboxylation, as a reaction intermediate. The reaction for obtaining the reactive compound from an acetoacetate ester or a derivative thereof, and the reaction relating to the substituents R1 and R2 of the reactive compound are described below.

Using an acetoacetate ester or a derivative thereof as a raw material, reaction with X—CH$_2$—Ar1-Y1 (X=halogen) under basic conditions causes either monoalkylation that yields a monoalkyl product or dialkylation (when Ar1=Ar2, Y1=Y2) that yields a dialkyl product (reactive compound). In the case of monoalkylation, a second alkylation reaction with X—CH$_2$—Ar2-Y2 (X=halogen) under basic conditions yields a dialkyl product (reactive compound).

The ester group of the obtained dialkyl product (α,α-dialkylated acetoacetate ester or derivative thereof) may be decomposed and decarboxylated to obtain a ketone (reactive compound). Further, the thus obtained ketone may be subjected to an addition reaction with a Grignard reagent or an alkyllithium reagent to form a tertiary alcohol (reactive compound). Moreover, the thus obtained tertiary alcohol (reactive compound) may be further reacted under basic conditions, either by alkylation to form an alkoxy compound (reactive compound) or by silylation to form a silyloxy compound (reactive compound).

Furthermore, by subjecting the above ketone to a Horner-Emmons-Wittig reaction to obtain an α,β-unsaturated ester (reactive compound), and then reacting this α,β-unsaturated ester with a Grignard reagent or an alkyllithium reagent in the presence of an equivalent amount or a catalytic amount of a copper reagent, a conjugate adduct ester (reactive compound) can be obtained. By reducing the thus obtained conjugate adduct ester, a primary alcohol (reactive compound) can be obtained. Moreover, the thus obtained primary alcohol may be further reacted under basic conditions, by alkylation to form an alkoxy compound (reactive compound), by esterification to form an ester compound (reactive compound), or by silylation to form a silyloxy compound (reactive compound).

By appropriately altering the X—CH$_2$—Ar1-Y1 or X—CH$_2$—Ar2-Y2 reacted with the acetoacetate ester or derivative thereof, Ar1, Ar2, Y1 and Y2 within the reactive compound represented by the above formula 4 can be altered to the desired groups. Specifically, by derivatizing Y1 and Y2 in X—CH$_2$—Ar1-Y1 and X—CH$_2$—Ar2-Y2, the desired functional substituents can be introduced into the reactive compound.

<4> Method of Producing the Compound and Polymer Compound

The compound of the present invention can be obtained, in a similar manner to the reactive compound of the present invention, using a malonate ester or derivative thereof or an acetoacetate ester or derivative thereof as a raw material. Further, the compound and the polymer compound of the present invention can be obtained, for example, using the reactive compound of the present invention and a compound having a substituent that participates in a condensation reaction as raw materials.

The compound of the present invention can be obtained, for example, by combining and reacting a reactive compound represented by one of the above formulas 13, 4, 7 or 8 and a compound having one substituent that participates in a condensation reaction.

Furthermore, the polymer compound of the present invention can be obtained, for example, by combining and then performing a condensation reaction between a reactive compound represented by one of the above formulas 13, 4, 7, 8, 14 or 10, and a compound having two substituents that participate in a condensation reaction or a compound having three or more such substituents, or alternatively, by performing a condensation reaction between reactive compounds represented by the above formulas 13, 4, 7, 8, 14 or 10.

In the method of producing the compound or polymer compound of the present invention, a conventional condensation reaction may be used. The compound having a substituent that participates in the condensation reaction varies depending on the variety of the polymerization reaction. For example, in those cases where a zero-valent nickel complex is used, such as the Kumada-Tamao coupling reaction, any compound having one halogen atom, alkyl sulfonate group, aryl sulfonate group or aryl alkyl sulfonate group as the substituent that participates in the condensation reaction may be used without any particular limitations. Further, in those cases where a nickel catalyst or a palladium catalyst is used, such as the Suzuki coupling reaction, any compound having one halogen atom, borate ester group or boric acid group as the substituent that participates in the condensation reaction may be used without any particular limitations.

Examples of the compound having a substituent that participates in the condensation reaction include any compounds having a substituent that is able to participate in a condensation reaction such as a halogen atom, alkyl sulfonate group, aryl sulfonate group, aryl alkyl sulfonate group, borate ester group, sulfonium methyl group, phosphonium methyl group, phosphonate methyl group, methyl monohalide group, boric acid group, formyl group, cyanomethyl group, vinyl group, ethynyl group, carboxyl group, ester group or amide group. Examples of the alkyl sulfonate group include a methane sulfonate group, ethane sulfonate group and trifluoromethane sulfonate group, and examples of the aryl sulfonate groups include a benzene sulfonate group and p-toluene sulfonate group.

Examples of the compound having two substituents that participate in the condensation reaction include compounds represented by the formula shown below.

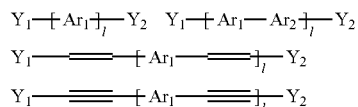

$$Y_1\text{—}Z\text{—}Y_2 \quad \text{[Chemical Formula 27]}$$

In this formula, Z, Y1 and Y2 are the same as defined above for Zn, Y1 and Y2 of the reactive compound.

Compounds represented by formulas shown below can be used particularly favorably as the compound having two substituents that participate in the condensation reaction.

[Chemical Formula 28]

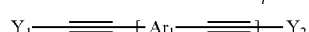
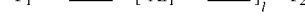

In these formulas, l represents an integer of 1 or greater. From the viewpoint of the optical properties, electrical properties or electrochemical properties of the compound and polymer compound obtained using the reactive compound, l is preferably within a range from 1 to 10, and more preferably from 1 to 3.

In the above formulas, Ar1, Ar2, Y1 and Y2 are the same as defined above for Ar1, Ar2, Y1 and Y2 of the reactive compound.

Specific examples of the method of producing the polymer compound of the present invention include a method of performing a polymerization using a nickel catalyst or a palladium catalyst, such as the Suzuki coupling reaction, a method of performing a polymerization using the Grignard reaction, a method of performing a polymerization using a zero-valent nickel complex, such as the Kumada-Tamao coupling reaction, a method of performing a polymerization using an oxide such as FeCl$_3$, a method of performing an oxidative polymerization electrochemically, and a method that involves decomposing an intermediate polymer having an appropriate leaving group.

In those cases where double bonds are to be generated within the main chain of the polymer compound of the present invention by condensation polymerization (for example, Z5 in the polymer compound represented by the above formula 3), examples of methods that may be used include the methods disclosed in JP 05-202355 A. Namely, specific examples of the method include polymerization of a compound having a formyl group and a compound having a phosphonium methyl group via the Wittig reaction, polymerization of a compound having both a formyl group and a phosphonium methyl group via the Wittig reaction, polymerization of a compound having a vinyl group and a compound having a halogen atom via the Heck reaction, polycondensation of a compound having two or more methyl monohalide groups via a dehydrohalogenation method, polycondensation of a compound having two or more sulfonium methyl groups via a sulfonium salt decomposition method, polymerization of a compound having a formyl group and a compound having a cyanomethyl group via the Knoevenagel reaction, and polymerization of a compound having two or more formyl groups via the McMurry reaction. The above groups can be used as the groups Y1 and Y2 of the reactive compound, or as the substituents of either the compound having two substituents that participate in the above condensation reaction or the compound having three or more substituents that participate in the condensation reaction.

In those cases where triple bonds are to be generated within the main chain of the polymer compound of the present invention by condensation polymerization (for example, Z5 in the polymer compound represented by the above formula 3), the Heck reaction or Sonogashira reaction can be used.

Of the above methods, a method of performing a polymerization using a nickel catalyst or a palladium catalyst, such as the Suzuki coupling reaction, a method of performing a polymerization using the Grignard reaction, a method of performing a polymerization using a zero-valent nickel complex, such as the Kumada-Tamao coupling reaction, and methods of performing polymerization using the Wittig reaction, the Heck reaction, the Sonogashira reaction or the Knoevenagel reaction are preferred in terms of facilitating control of the structure.

<5> Applications of the Compound and Polymer Compound of the Present Invention

In the compound and polymer compound of the present invention, because the aromatic rings readily adopt a stacked structure, a hypochromic effect is obtained, and the absorption coefficient attributable to the aromatic rings is smaller than the corresponding absorption coefficients of the substituents used for introducing the aromatic rings (for example, Z1 and Z2 in the formula 1, Z3, Z4, Ar1 and Ar2 in the formula 2, and Z5, Ar1 and Ar2 in the formula 3). Accordingly, the compound or polymer compound of the present invention is useful as a material for inclusion within compositions for light-emitting materials, light-resistant materials, ultraviolet-transparent materials, heat-conductive materials or the like. Further, by utilizing the excimer emission of the compound or polymer compound of the present invention, applications as laser materials or electroluminescent materials are also possible.

Figure 3:
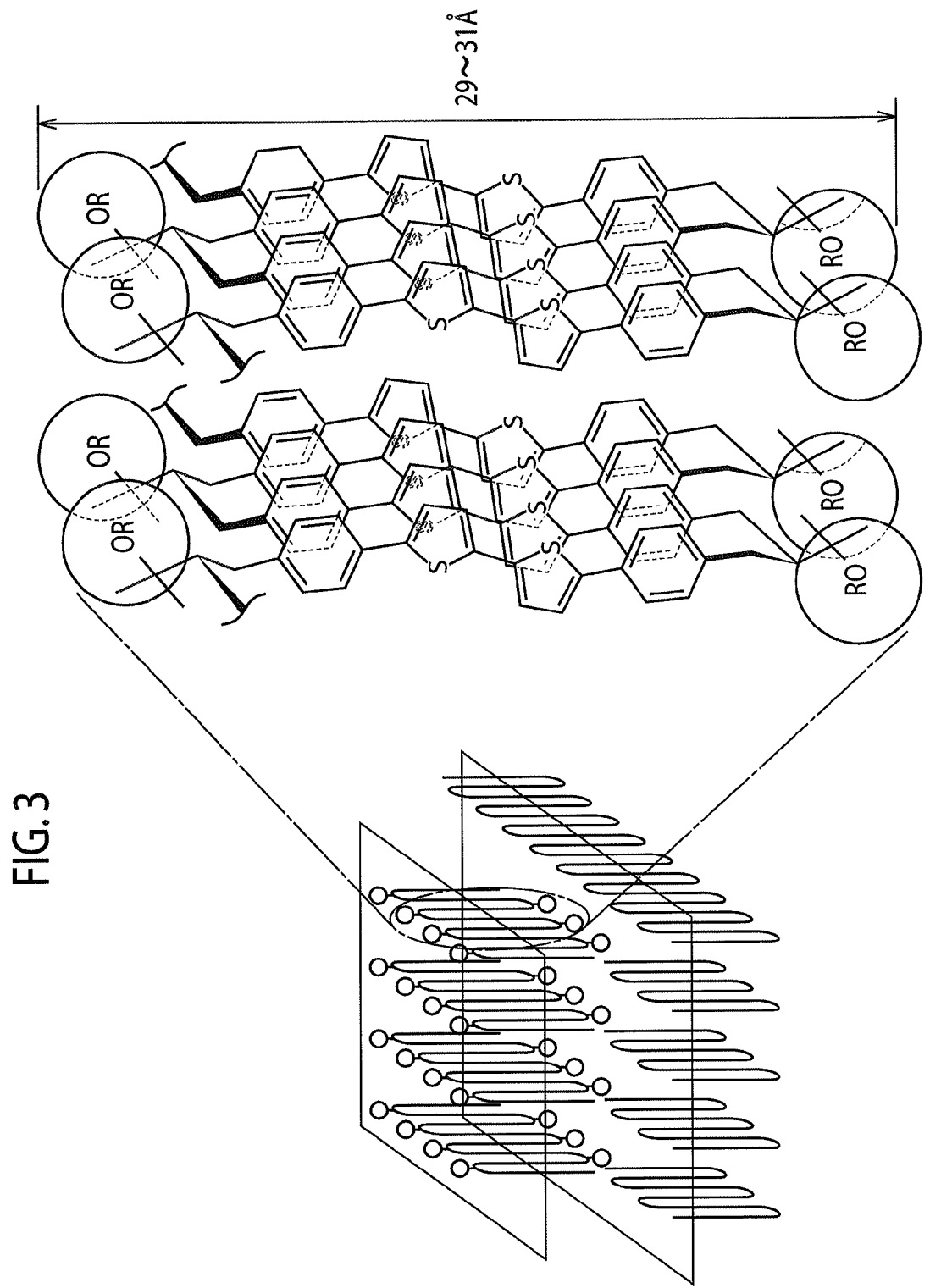
FIG. 3 illustrates an image of a polymer compound of the present invention shaped into a film-like form.

By forming the polymer compound of the present invention in a film-like form and then performing a heat treatment, a layer-like structure can be formed. In the present invention, a layer-like structure of the polymer compound describes a state where the polymer chain is folded to form layers. A specific example is the image shown in FIG. 3. The conditions of the heat treatment used for forming the layer-like structure include, for example, first dissolving the polymer compound in a solvent such as dichloromethane, subsequently applying a film of the solution to a substrate, and then heating the applied film at 40 to 300° C.

Forming a layer-like structure is preferable in terms of grouping together the conjugated structure portions to obtain a film having different optical properties, electrical properties or electrochemical properties from the monomer containing the π-conjugated groups.

The compound or polymer compound of the present invention can also be used as a material for inclusion within a composition used for forming a material used in an organic device such as a charge transport material. In particular, the polymer compound is soluble in organic solvents and exhibits excellent film-forming properties and workability. In those cases where the compound or polymer compound of the present invention is used as a charge transport material, the compound or polymer compound may be used alone, or may be used in a mixture with other components (including conventional charge transport materials, other polymers or monomers, and additives such as silane coupling agents).

Examples of conventional charge transport materials include arylamine derivatives, carbazole derivatives and thiophene derivatives. Examples of the other polymers or monomers include any of the polymers or monomers used in conventional charge transport materials, and specific examples include polyvinylcarbazole and derivatives thereof, polycarbazole and derivatives thereof, polysilane and derivatives thereof, polysiloxane derivatives having an aromatic amine in a side chain or the main chain, polyarylamine and derivatives thereof, polyaniline and derivatives thereof, polythiophene and derivatives thereof, polypyrrole and derivatives thereof, poly(p-phenylenevinylene) and derivatives thereof, and poly(2,5-thienylenevinylene) and derivatives thereof.

By utilizing their charge transport capabilities, the compound and polymer compound of the present invention can be used in field effect transistors (FET), thin film transistors (TFT), organic light emitting devices (organic EL), light emitting diodes (LED) and solar cells.

In those cases where the compound or polymer compound of the present invention is used in an organic device such as a field effect transistor (FET), thin film transistor (TFT), organic light emitting device (organic EL), light emitting diode (LED), solar cell, chemical sensor, biosensor, laser or electronic copier, the purity of the compound or polymer compound may have an effect on the performance of the organic device. Accordingly, it is preferable that the raw materials for the compound, reactive compound and polymer compound of the present invention are purified by distillation, sublimation purification, recrystallization, column chromatography or the like prior to use in the reaction. Further, the compound, reactive compound or polymer compound obtained following the reaction is preferably purified using conventional purification and separation operations such as acid washing, alkali washing, neutralization, water washing, organic solvent washing, re-precipitation, centrifugal separation, extraction, column chromatography or dialysis, as well as drying, heavy metal removal using metal scavengers, or other methods.

One embodiment of the compound of the present invention can provide a compound that adopts a π-stacked structure in which the π-conjugated groups are stacked upon each other. Further, one embodiment of the polymer compound of the present invention can provide a polymer compound that adopts a π-stacked structure in which the π-conjugated groups are stacked upon each other. Furthermore, one embodiment of the reactive compound of the present invention can provide a reactive compound that can be used as a raw material for the above compound and the above polymer compound, or can provide a method of efficiently producing the target compound or polymer compound using the reactive compound. Moreover, one embodiment of a composition or organic device of the present invention can provide a composition or organic device which exhibits unique properties as a result of containing the above compound or polymer compound having a π-stacked structure.

Moreover, in another embodiment of the present invention, the compound or polymer compound can adopt a π-stacked structure in which the π-conjugated groups are stacked upon each other, in solution and/or within a solid state. Further, the compound can exhibit optical properties different from the optical properties of the stand-alone form of the π-conjugated group portion contained within the compound, and the polymer compound can exhibit optical properties different from the optical properties of the monomer containing the π-conjugated groups. Furthermore, the compound can preferably exhibit electrical properties, electrochemical properties or the like that are different from those of the stand-alone form of the π-conjugated group portion contained within the compound, and the polymer compound can preferably exhibit electrical properties, electrochemical properties or the like that are different from those of the monomer containing the π-conjugated groups.

In another embodiment of the present invention, the compound or polymer compound exhibits efficient and selective excimer emission, and in particular, can produce an excimer emission in the blue to ultraviolet range, and therefore displays excellent industrial applicability. Furthermore, a composition or organic device containing the compound and/or polymer compound of the present invention can be used as a material having unique optical properties, which can be used as an electroluminescent material or laser emitting material that emits light from the ultraviolet region through to the visible region.

EXAMPLES

Synthesis of Compounds (π-Stacked Single Molecules)

Example 1-1

Synthesis of diethyl 2,2-dibenzylmalonate (1a-1)

Diethyl malonate (4.53 mL, 30.0 mmol) was added gradually at 0° C. to a mixed liquid containing sodium hydride (55 wt % in oil, 2.95 g, 67.5 mmol) and anhydrous N,N-dimethylformamide (60 mL). Following stirring of the resulting mixed liquid at this temperature for 30 minutes, benzyl chloride (7.25 mL, 63.0 mmol) was added. The resulting mixed liquid was stirred at room temperature for one hour, and a saturated aqueous solution of ammonium chloride was then added to halt the reaction. The organic layer was separated from the mixed liquid, and the water layer was extracted with ethyl acetate. The thus obtained organic layer was washed with a saturated saline solution and then dried using anhydrous magnesium sulfate, yielding the title compound (1a-1) in a yield of 95%.

Example 1-2

Synthesis of ethyl 2-benzyl-3-phenylpropanoate (1a-2)

[Chemical Formula 29]

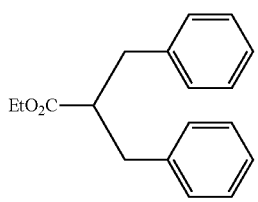

(1a-2)

Diethyl malonate (4.53 mL, 30.0 mmol) was added gradually at 0° C. to a mixed liquid containing sodium hydride (55 wt % in oil, 2.95 g, 67.5 mmol) and anhydrous N,N-dimethylformamide (60 mL). Following stirring of the resulting mixed liquid at this temperature for 30 minutes, benzyl chloride (7.25 mL, 63.0 mmol) was added.

The resulting mixed liquid was stirred at room temperature for one hour, and a saturated aqueous solution of ammonium chloride was then added to halt the reaction. The organic layer was separated from the mixed liquid, and the water layer was extracted with ethyl acetate. The thus obtained organic layer was washed with a saturated saline solution and then dried using anhydrous magnesium sulfate.

Following filtering of the organic layer, the filtrate was concentrated under reduced pressure, and to the resulting residue were added lithium chloride (5.09 g, 120 mmol), water (1.08 mL) and N,N-dimethylformamide (100 mL) to form a mixed liquid. This mixed liquid was then heated for 24 hours at 160° C. The mixed liquid was cooled to room temperature, and following the addition of water (100 mL), was extracted with ethyl acetate. The thus obtained organic layer was dried using anhydrous magnesium sulfate and filtered. The filtrate was concentrated under reduced pressure, and the resulting residue was purified by silica gel column chromatography (hexane:ethyl acetate=30:1), yielding the title compound (1a-2) (7.24 g, 27.0 mmol) as a colorless liquid in a yield of 90%.

The results of NMR and the like are shown below.

$^1$H NMR (500 MHz, CDCl$_3$) δ 7.27 (t, 4H, J=7.5 Hz, Ar), 7.21 to 7.15 (m, 6H, Ar), 3.95 (q, 2H, J=7.3 Hz, CO$_2$CH$_2$CH$_3$), 2.99 to 2.93 (m, 3H, CH$_2$Ar and CHCH$_2$Ar), 2.83 to 2.77 (m, 2H, CH$_2$Ar), 1.00 (t, 3H, J=7.3 Hz, CO$_2$CH$_2$CH$_3$).

$^{13}$C NMR (CDCl$_3$, 125 MHz) δ 174.9, 139.1, 128.9, 128.3, 126.3, 60.2, 49.6, 38.2, 14.0.

IR (neat) 3062, 3028, 2980, 2953, 2927, 1731, 1604, 1496, 1454, 1376, 1256, 1217, 1173, 1162, 1032, 744.4, 700.0 cm$^{-1}$.

Example 2

Synthesis of 3-benzyl-2-methyl-4-phenylbutan-2-ol (1b)

[Chemical Formula 30]

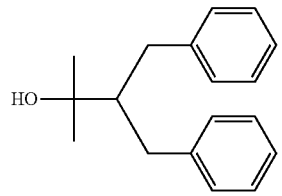

(1b)

A mixed liquid of ethyl 2-benzyl-3-phenylpropanoate (805 mg, 3.0 mmol) and tetrahydrofuran (3.0 mL) in a reaction container was deaerated, and the air inside the reaction container was replaced with argon. The mixed liquid was cooled to −40° C., an ether solution of methyllithium (6.1 mL, 1.1 M, 6.7 mmol) was added, and following stirring for 30 minutes, the mixture was stirred at room temperature for a further 16 hours. A saturated aqueous solution of ammonium chloride was added to the mixed liquid to halt the reaction, and the mixed liquid was then extracted with ethyl acetate. The thus obtained organic layer was washed with water, dried using anhydrous magnesium sulfate, and then filtered.

The filtrate was concentrated under reduced pressure, and the resulting residue was purified by silica gel column chromatography (hexane:ethyl acetate=30:1), yielding the title compound (1b) (670 mg, 2.6 mmol) as a colorless liquid in a yield of 88%.

The results of NMR and the like are shown below.

$^1$H NMR (500 MHz, CDCl$_3$) δ 7.20 (t, 4H, J=7.5 Hz, Ar), 7.12 (t, 2H, J=7.5 Hz, Ar), 7.05 (d, 4H, J=7.0 Hz, Ar), 2.88 (dd, 2H, J=5.8, 14.0 Hz, CH$_2$Ar), 2.50 (dd, 2H, J=7.5, 14.0 Hz, CH$_2$Ar), 2.21 to 2.16 (m, 1H, CHCH$_2$Ar), 1.26 (s, 6H, (CH$_3$)$_2$C).

$^{13}$C NMR (125 MHz, CDCl$_3$) δ 142.0, 129.0, 128.3, 125.7, 74.3, 53.9, 36.8, 27.6.

IR (neat) 3415, 3025, 2971, 2931, 1603, 1494, 1453, 1372, 1156, 1129, 747.3, 699.1 cm$^{-1}$.

HR-MS: m/z=calcd For C$_{18}$H$_{22}$NaO [M+Na]$^+$: 277.1568. found 277.1522.

Example 3

Synthesis of (2-(2-methoxypropan-2-yl)propan-1,3-diyl)dibenzene (1c)

[Chemical Formula 31]

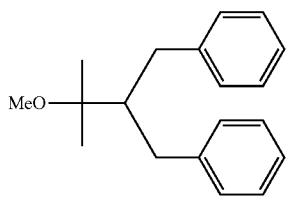

(1c)

3-benzyl-2-methyl-4-phenylbutan-2-ol (51 mg, 0.20 mmol) was added gradually at 0° C. to a mixed liquid containing sodium hydride (55 wt % in oil, 13 mg, 0.30 mmol) and anhydrous dimethylsulfoxide (1.0 mL). Following stirring of the resulting mixed liquid at this temperature for 30 minutes, dimethyl sulfate (37 mg, 0.30 mmol) was added.

The resulting mixed liquid was stirred at room temperature for 24 hours, and a saturated aqueous solution of ammonium chloride was then added to halt the reaction. The organic layer was separated from the mixed liquid, and the water layer was extracted with ethyl acetate. The thus obtained organic layer was washed with a saturated saline solution and then dried using anhydrous magnesium sulfate. Following filtering of the organic layer, the filtrate was concentrated under reduced pressure, and the resulting residue was purified by silica gel column chromatography (hexane:ethyl acetate=30:1), yielding the title compound (1c) (43 mg, 0.16 mmol) as a colorless liquid in a yield of 81%.

The results of NMR and the like are shown below.

$^1$H NMR (500 MHz, CDCl$_3$) δ 7.16 (t, 4H, J=7.3 Hz, Ar), 7.09 (t, 2H, J=7.0 Hz, Ar); 7.00 (d, 4H, J=7.0 Hz, Ar), 3.14 (s, 3H, OCH$_3$), 2.87 (dd, 2H, J=5.0, 14.0 Hz, CH$_2$Ar), 2.46 (dd, 2H, J=7.8, 14.3 Hz, CH$_2$Ar), 2.31 to 2.26 (m, 1H, CHCH$_2$Ar), 1.15 (s, 6H, (CH$_3$)$_2$C).

$^{13}$C NMR (125 MHz, CDCl$_3$) δ 142.3, 129.0, 128.0, 125.4, 77.7, 50.3, 48.8, 36.5, 23.2.

IR (neat) 3030, 2968, 2939, 2829, 1605, 1498, 1457, 1379, 1363, 1182, 1137, 1076, 744.4, 699.1 cm$^{-1}$.

HR-MS: m/z=calcd For C$_{19}$H$_{24}$NaO [M+Na]$^+$: 291.1725. found 291.1748.

Example 4

Synthesis of (3-benzyl-2-methyl-4-phenylbutan-2-yloxy)triethylsilane (1d)

[Chemical Formula 32]

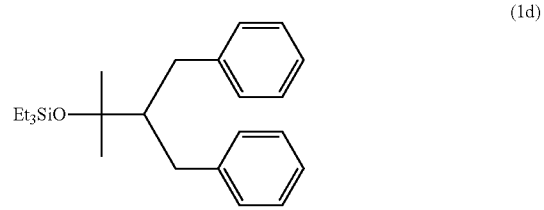

(1d)

A mixed liquid of 3-benzyl-2-methyl-4-phenylbutan-2-ol (1.53 g, 6.0 mmol) and pyridine (12 mL) in a reaction container was deaerated, and the air inside the reaction container was replaced with argon. Triethylsilyl chloride (1.3 mL, 7.5 mmol) was added to the mixed liquid, and stirred at 60° C. for 20 hours. Following cooling of the mixed liquid to room temperature, a saturated aqueous solution of ammonium chloride was added to halt the reaction. The organic layer was separated from the mixed liquid, and the water layer was extracted with hexane.

The thus obtained organic layer was washed with water, dried using anhydrous magnesium sulfate, and filtered. The filtrate was concentrated under reduced pressure, and the resulting residue was purified by silica gel column chromatography (hexane), yielding the title compound (1d) (2.10 g, 5.7 mmol) as a colorless liquid in a yield of 95%.

The results of NMR and the like are shown below.

$^1$H NMR (500 MHz, CDCl$_3$) δ 7.14 (t, 4H, J=7.5 Hz, Ar), 7.07 (t, 2H, J=7.5 Hz, Ar), 6.98 (d, 4H, J=7.0 Hz, Ar), 2.95 (dd, 2H, J=4.8, 14.3 Hz, CH$_2$Ar), 2.43 (dd, 2H, J=7.5, 14.0 Hz, CH$_2$Ar), 2.13 to 2.08 (m, 1H, CHCH$_2$Ar), 1.21 (s, 6H, (CH$_3$)$_2$C), 0.98 (t, J=8.0 Hz, 9H, (CH$_3$CH$_2$)$_3$Si), 0.61 (q, 6H, J=7.5 Hz, (CH$_3$CH$_2$)$_3$Si).

$^{13}$C NMR (125 MHz, CDCl$_3$) δ 142.8, 129.0, 128.0, 125.3, 76.3, 54.8, 36.7, 28.3, 7.2, 6.9.

IR (neat) 3025, 2954, 2874, 1603, 1495, 1454, 1383, 1142, 1039, 738.6, 698.1 cm$^{-1}$.

HR-MS: m/z=calcd For C$_{24}$H$_{36}$KOSi [M+K]$^+$: 407.2173. found 407.2178.

Example 5

Synthesis of 2-benzyl-3-ethyl-1-phenylpentan-3-ol (1e)

[Chemical Formula 33]

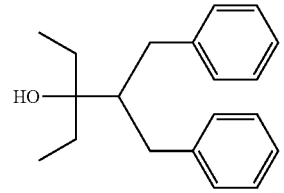

(1e)

A mixed liquid of ethyl 2-benzyl-3-phenylpropanoate (403 mg, 1.5 mmol) and tetrahydrofuran (2.0 mL) in a reaction container was deaerated, and the air inside the reaction container was replaced with argon. The mixed liquid was cooled to 0° C., and a tetrahydrofuran solution of ethylmagnesium bromide (3.5 mL, 1.2 M, 4.2 mmol) was added and stirred at 50° C. for 16 hours. A saturated aqueous solution of ammonium chloride was added to the mixed liquid to halt the reaction, and the mixed liquid was then extracted with ethyl acetate.

The thus obtained organic layer was washed with water, dried using anhydrous magnesium sulfate, and filtered. The filtrate was concentrated under reduced pressure, and the resulting residue was purified by silica gel column chromatography (hexane:ethyl acetate=30:1), yielding the title compound (1e) (305 mg, 1.1 mmol) as a colorless liquid in a yield of 72%.

The results of NMR and the like are shown below.

$^1$H NMR (500 MHz, CDCl$_3$) δ 7.18 (t, 4H, J=7.5 Hz, Ar), 7.10 (t, 2H, J=7.0 Hz, Ar), 7.02 (d, 4H, J=6.5 Hz, Ar), 2.90 (dd, 2H, J=5.0, 14.5 Hz, CH$_2$Ar), 2.48 (dd, 2H, J=7.5, 13.5 Hz, CH$_2$Ar), 2.33 to 2.28 (m, 1H, CHCH$_2$Ar), 1.69 to 1.55 (m, 4H, (CH$_2$CH$_3$)$_2$C), 0.87 (t, 6H, J=7.3 Hz, (CH$_2$CH$_3$)$_2$C).

$^{13}$C NMR (125 MHz, CDCl$_3$) δ 142.2, 129.0, 128.2, 125.6, 77.3, 49.1, 35.9, 28.7, 7.6.

IR (neat) 3444, 3025, 2965, 2935, 2879, 1495, 1454, 1385, 1258, 746.3, 699.1 cm$^{-1}$.

HR-MS: m/z=calcd For C$_{20}$H$_{26}$NaO [M+Na]$^+$: 305.1881. found 305.1852.

Example 6

Synthesis of (2-(3-methoxypentan-3-yl)propan-1,3-diyl)dibenzene (1f)

[Chemical Formula 34]

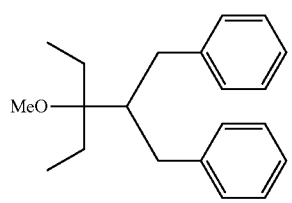

(1f)

2-benzyl-3-ethyl-2-phenylpentan-3-ol (50 mg, 0.18 mmol) was added gradually at 0° C. to a mixed liquid containing sodium hydride (60 wt % in oil, 11 mg, 0.28 mmol) and tetrahydrofuran (2.0 mL). Following stirring of the resulting mixed liquid at this temperature for 30 minutes, iodomethane (51 mg, 0.36 mmol) was added.

The resulting mixed liquid was stirred at 40° C. for 2 hours, and a saturated aqueous solution of ammonium chloride was then added to halt the reaction. The organic layer was separated from the mixed liquid, and the water layer was extracted with ethyl acetate. The thus obtained organic layer was washed with a saturated saline solution and then dried using anhydrous magnesium sulfate. Following filtering of the organic layer, the filtrate was concentrated under reduced pressure, and the resulting residue was purified by silica gel column chromatography (hexane:ethyl acetate=30:1), yielding the title compound (1f) (48 mg, 0.16 mmol) as a light yellow liquid in a yield of 90%.

The results of NMR and the like are shown below.

$^1$H NMR (500 MHz, CDCl$_3$) δ 7.13 (t, 4H, J=7.3 Hz, Ar), 7.06 (t, 2H, J=7.0 Hz, Ar), 6.95 (d, 4H, J=7.5 Hz, Ar), 3.17 (s, 3H, OCH$_3$), 3.00 (dd, 2H, J=4.3, 14.3 Hz, CH$_2$Ar), 2.47 (dd, 2H, J=7.8, 13.8 Hz, CH$_2$Ar), 2.34 to 2.30 (m, 1H, CHCH$_2$Ar), 1.69 to 1.56 (m, 4H, (CH$_2$CH$_3$)$_2$C), 0.89 (t, 6H, J=7.5 Hz, (CH$_3$CH$_2$)$_2$C).

$^{13}$C NMR (125 MHz, CDCl$_3$) δ 142.7, 129.0. 128.0, 125.3, 80.7, 49.2, 48.6, 36.8, 26.4, 8.6.

IR (neat) 3025, 2973, 2928, 2819, 1602, 1495, 1454, 1384, 1087, 749.2, 699.1 cm$^{-1}$.

HR-MS: m/z=calcd For C$_{21}$H$_{28}$KO [M+K]$^+$: 335.1777. found 335.1774.

Example 7

Synthesis of (2-(1-methoxyethyl)propan-1,3-diyl)dibenzene (1g)

[Chemical Formula 35]

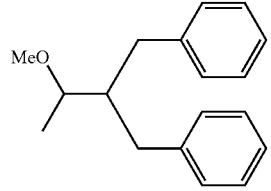

(1g)

2-benzyl-3-phenylpropan-1-ol (226 mg, 1.0 mmol) was added gradually at 0° C. to a mixed liquid containing pyridinium chlorochromate (323 mg, 1.5 mmol), celite (323 mg) and dichloromethane (4.0 mL).

Following stirring of the thus obtained mixed liquid at room temperature for 2 hours, hexane was added to halt the reaction, and the mixed liquid was filtered. The filtrate was concentrated under reduced pressure, and the resulting residue was purified by silica gel column chromatography (hexane:ethyl acetate=30:1), yielding a colorless liquid. Tetrahydrofuran (1.5 mL) was added to the obtained liquid, the resulting mixed liquid was cooled to −40° C., and an ether solution of methyllithium (2.1 mL, 1.1 M, 2.3 mmol) was added.

Following stirring of the mixed liquid at −40° C. for 30 minutes, the mixture was stirred at room temperature for 16 hours. A saturated aqueous solution of ammonium chloride was added to the mixed liquid to halt the reaction, and the mixed liquid was then extracted with ethyl acetate. The thus obtained organic layer was washed with water, dried using anhydrous magnesium sulfate, and then filtered. The filtrate was concentrated under reduced pressure, and the resulting residue was added gradually at 0° C. to a mixed liquid containing sodium hydride (60 wt % in oil, 72 mg, 1.8 mmol) and tetrahydrofuran (5.0 mL). Following stirring of the resulting mixed liquid at this temperature for 30 minutes, iodomethane (284 mg, 2.0 mmol) was added.

The resulting mixed liquid was stirred at 40° C. for 2 hours, and a saturated aqueous solution of ammonium chloride was then added to halt the reaction. The organic layer was separated from the mixed liquid, and the water layer was extracted with ethyl acetate. The thus obtained organic layer was washed with a saturated saline solution and then dried using anhydrous magnesium sulfate. Following filtering of the organic layer, the filtrate was concentrated under reduced pressure, and the resulting residue was purified by silica gel column chromatography (hexane:ethyl acetate=30:1), yielding the title compound (1g) (145 mg, 0.57 mmol) as a colorless liquid in a yield of 57%.

The results of NMR and the like are shown below.

$^1$H NMR (500 MHz, CDCl$_3$) δ 7.26 (t, 4H, J=7.5 Hz, Ar), 7.17 (t, 2H, J=7.5 Hz, Ar), 7.12 (d, 4H, J=7.5 Hz, Ar), 3.28 (s, 3H, OCH$_3$), 3.21 (dq, 1H, J=3.5, 6.3 Hz, CH$_3$O(CH$_3$)CHCH), 2.80 (dd, 1H, J=6.8, 13.8 Hz, CH$_2$Ar), 2.66 (dd, 1H, J=7.0, 14.0 Hz, CH$_2$Ar), 2.58 (dd, 1H, J=7.8, 13.8 Hz, CH$_2$Ar), 2.44 (dd, 1H, J=7.0, 13.5 Hz, CH$_2$Ar), 2.14 to 2.07 (m, 1H, CHCH$_2$Ar), 1.15 (d, 3H, J=6.5 Hz, CHCH$_3$).

$^{13}$C NMR (125 MHz, CDCl$_3$) δ 141.5, 141.2, 129.2, 129.0, 128.3, 128.2, 128.1, 125.7, 76.1, 56.2, 47.1, 35.6, 35.3, 15.2.

IR (neat) 3021, 2977, 2932, 2817, 1596, 1495, 1454, 981.6, 744.4, 700.0 cm$^{-1}$.

HR-MS: m/z=calcd For C$_{18}$H$_{22}$NaO [M+Na]$^+$: 277.1568. found 277.1563.

Example 8

Synthesis of 2-benzyl-3-phenylpropan-1-ol (1h)

[Chemical Formula 36]

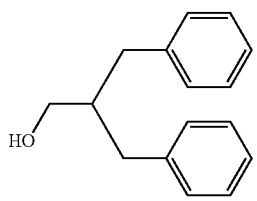

(1h)

Ethyl 2-benzyl-3-phenylpropanoate (537 mg, 2.0 mmol) was added gradually at 0° C. to a mixed liquid containing lithium aluminum hydride (76 mg, 2.0 mmol) and tetrahydrofuran (4.0 mL).

The resulting mixed liquid was stirred at room temperature for 2 hours, and water was then added to halt the reaction. The organic layer was separated from the mixed liquid, and the water layer was extracted with ethyl acetate. The thus obtained organic layer was washed with a saturated saline solution and then dried using anhydrous magnesium sulfate. Following filtering of the organic layer, the filtrate was concentrated under reduced pressure, and the resulting residue was purified by silica gel column chromatography (hexane:ethyl acetate=30:1), yielding the title compound (1h) (453 mg, 1.98 mmol) as a colorless liquid in a yield of 99%.

The results of NMR and the like are shown below.

$^1$H NMR (500 MHz, CDCl$_3$) δ 7.28 (t, 4H, J=7.5 Hz, Ar), 7.21 to 7.17 (m, 6H, Ar), 3.49 (t, 2H, J=4.8 Hz, CH$_2$OH), 2.74 to 2.63 (m, 4H, CH$_2$Ar), 2.17 to 2.09 (m, 1H, CHCH$_2$Ar), 1.20 (t, 1H, J=5.0 Hz, CH$_2$OH).

$^{13}$C NMR (CDCl$_3$, 125 MHz) δ 140.5, 129.1, 128.4, 126.0, 64.0, 44.5, 37.4.

IR (neat) 3359, 3083, 3061, 3025, 2922, 2856, 1602, 1495, 1453, 1023, 751.1, 735.7, 699.1 cm$^{-1}$.

HR-MS: m/z=calcd For C$_{16}$H$_{18}$NaO [M+Na]$^+$: 249.1255. found 249.1209.

Example 9

Synthesis of (2-(methoxymethyl)propan-1,3-diyl)dibenzene (1i)

[Chemical Formula 37]

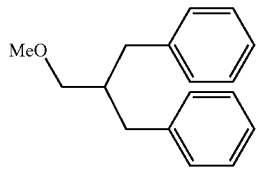

(1i)

2-benzyl-3-phenylpropan-1-ol (41 mg, 0.18 mmol) was added gradually at 0° C. to a mixed liquid containing sodium hydride (60 wt % in oil, 11 mg, 0.27 mmol) and tetrahydrofuran (2.0 mL). Following stirring of the resulting mixed liquid at this temperature for 30 minutes, iodomethane (50 mg, 0.36 mmol) was added.

The resulting mixed liquid was stirred at 40° C. for 2 hours, and a saturated aqueous solution of ammonium chloride was then added to halt the reaction. The organic layer was separated from the mixed liquid, and the water layer was extracted with ethyl acetate. The thus obtained organic layer was washed with a saturated saline solution and then dried using anhydrous magnesium sulfate. Following filtering of the organic layer, the filtrate was concentrated under reduced pressure, and the resulting residue was purified by silica gel column chromatography (hexane:ethyl acetate=30:1), yielding the title compound (1i) (38 mg, 0.16 mmol) as a colorless liquid in a yield of 88%.

The results of NMR and the like are shown below.

$^1$H NMR (500 MHz, CDCl$_3$) δ 7.28 (t, 4H, J=7.3 Hz, Ar), 7.19 (t, 2H, J=7.5 Hz, Ar), 7.16 (d, 4H, J=6.5 Hz, Ar), 3.29 (s, 3H, OCH$_3$), 3.15 (d, 2H, J=5.0 Hz, CH$_3$OCH$_2$), 2.70 (dd, 2H, J=8.3, 13.8 Hz, CH$_2$Ar), 2.62 (dd, 2H, J=6.8, 13.3 Hz, CH$_2$Ar), 2.19 to 2.12 (m, 1H, CHCH$_2$Ar).

$^{13}$C NMR (125 MHz, CDCl$_3$) δ 140.6, 129.2, 128.2, 125.8, 73.4, 58.7, 42.6, 37.5.

IR (neat) 3026, 2924, 1495, 1454, 1385, 1252, 1120, 750.2 cm$^{-1}$.

HR-MS: m/z=calcd For C$_{17}$H$_{21}$O [M+H]$^+$: 241.1592. found 241.1561.

Example 10

Synthesis of triethyl(2-methyl-3-(4-phenylethynyl)benzyl)-4-(4-(phenylethynyl)phenyl)butan-2-yloxy)silane (2a)

[Chemical Formula 38]

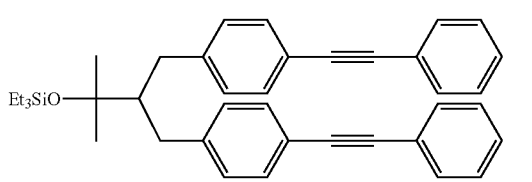

(2a)

A mixed liquid of (3-(4-bromobenzyl)-4-(4-bromophenyl)-2-methylbutan-2-yloxy)triethylsilane (526 mg, 1.0 mmol), bis(triphenylphosphine)palladium(11) dichloride (70 mg, 0.10 mmol), copper iodide (19 mg, 0.10 mmol), triphenylphosphine (53 mg, 0.20 mmol), triethylamine (1.4 mL) and tetrahydrofuran (3.3 mL) in a reaction container was deaerated, and the air inside the reaction container was replaced with argon.

Ethynylbenzene (306 mg, 3.0 mmol) was added to the obtained mixed liquid, and the resulting mixture was stirred at 80° C. for 12 hours. The mixed liquid was then cooled to room temperature, and a saturated aqueous solution of ammonium chloride was added to halt the reaction. The thus obtained organic layer was washed with water, dried using anhydrous sodium sulfate, and filtered. The filtrate was concentrated under reduced pressure, and the resulting residue was purified by silica gel column chromatography (hexane), yielding the title compound (2a) (68 mg, 0.12 mmol) as a light yellow viscous solid in a yield of 12%.

The results of NMR and the like are shown below.

$^1$H NMR (600 MHz, CDCl$_3$) δ 7.52 to 7.49 (m, 4H, Ar), 7.34 to 7.30 (m, 10H, Ar), 6.97 (d, 4H, J=7.2 Hz, Ar), 2.99 (dd, 2H, J=4.8, 14.4 Hz, CH$_2$Ar), 2.43 (dd, 2H, J=8.1, 14.1 Hz, CH$_2$Ar), 2.12 to 2.08 (m, 1H, CHCH$_2$Ar), 1.22 (s, 6H, (CH$_3$)$_2$C), 0.98 (t, 9H, J=7.8 Hz, (CH$_3$CH$_2$)$_3$Si), 0.62 (q, 6H, J=8.0 Hz, (CH$_3$CH$_2$)$_3$Si).

$^{13}$C NMR (CDCl$_3$, 150 MHz) δ 143.1, 131.5, 131.4, 129.0, 128.3, 128.0, 123.5, 120.2, 89.6, 88.7, 76.2, 54.8, 36.8, 28.3, 7.2, 6.9.

IR (neat) 2962, 2905, 1596, 1416, 1385, 1260, 1012, 798.4, 689.4 cm$^{-1}$.

HR-MS: m/z=calcd For C$_{40}$H$_{45}$OSi [M+H]$^+$: 569.3240. found 569.3218.

Example 11

Synthesis of triethyl(2-methyl-3-(4-styrylbenzyl)-4-(4-styrylphenyl)butan-2-yloxy)silane (2b)

[Chemical Formula 39]

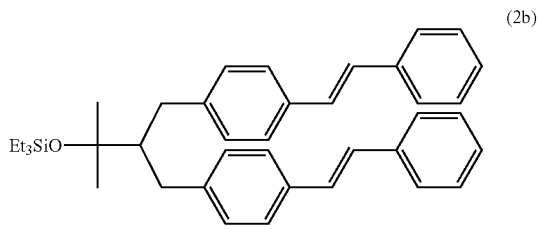

(2b)

A mixed liquid of (3-(4-bromobenzyl)-4-(4-bromophenyl)-2-methylbutan-2-yloxy)triethylsilane (526 mg, 1.0 mmol), (E)-4,4,5,5-tetramethyl-2-styryl-1,3,2-dioxaborolane (690 mg, 3.0 mmol), a 2 M aqueous solution of potassium carbonate (1.0 mL) and tetrahydrofuran (2.5 mL) in a reaction container was deaerated, and the air inside the reaction container was replaced with argon. A solution of tetrakistriphenylphosphinepalladium(0) (46 mg, 0.04 mmol) in tetrahydrofuran (2.5 mL) was then added to the mixed liquid.

The thus obtained mixed liquid was stirred at 80° C. for 15 hours, and following cooling to room temperature, a saturated aqueous solution of sodium hydrogen carbonate was added to halt the reaction. The thus obtained organic layer was washed with water, dried using anhydrous sodium sulfate, and filtered. The filtrate was concentrated under reduced pressure, and the resulting residue was purified by silica gel column chromatography (hexane), yielding the title compound (2b) (195 mg, 0.34 mmol) as a white solid in a yield of 34%.

The results of NMR and the like are shown below.

$^1$H NMR (600 MHz, CDCl$_3$) $^1$H NMR (600 MHz, CDCl$_3$) δ 7.46 (d, 4H, J=7.8 Hz, Ar), 7.32 (t, 4H, J=7.5 Hz, Ar), 7.29 (d, 4H, J=7.8 Hz, Ar), 7.23 (t, J=7.2 Hz, 2H, Ar), 7.06 to 7.01 (m, 4H, Ar and CH=CH), 6.99 to 6.96 (m, 4H, Ar and CH=CH), 2.99 (dd, 2H, J=4.5, 14.1 Hz, CH$_2$Ar), 2.42 (dd, 2H, J=8.1, 14.1 Hz, CH$_2$Ar), 2.15 to 2.11 (m, 1H, CHCH$_2$Ar), 1.24 (s, 6H, (CH$_3$)$_2$C), 0.99 (t, 9H, J=8.1 Hz, (CH$_3$CH$_2$)$_3$Si), 0.63 (q, 6H, J=8.0 Hz, (CH$_3$CH$_2$)$_3$Si).

$^{13}$C NMR (CDCl$_3$, 150 MHz) δ 142.4, 137.5, 134.5, 129.3, 128.7, 128.6, 127.6, 127.3, 126.4, 126.2, 76.3, 54.9, 36.6, 28.3, 7.3, 6.9.

IR (neat) 3024, 2961, 2874, 1597, 1513, 1454, 1416, 1383, 1261, 1016, 810.9 cm$^{-1}$.

HR-MS: m/z=calcd For C$_{40}$H$_{48}$NaOSi [M+Na]$^+$: 595.3372. found 595.3386.

Example 12

Synthesis of triethyl(2-methyl-3-(4-(4-methylstyryl)benzyl)-4-(4-(4-methylstyryl)phenyl)butan-2-yloxy)silane (2c)

[Chemical Formula 40]

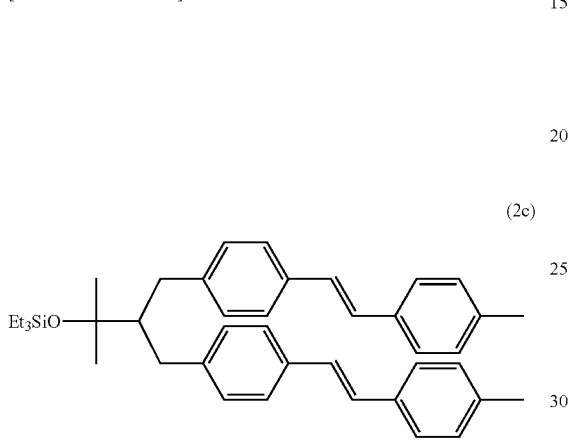

(2c)

A mixed liquid of (3-(4-bromobenzyl)-4-(4-bromophenyl)-2-methylbutan-2-yloxy)triethylsilane (526 mg, 1.0 mmol), (E)-4,4,5,5-tetramethyl-2-(4-methylstyryl)-1,3,2-dioxaborolane (733 mg, 3.0 mmol), a 2 M aqueous solution of potassium carbonate (1.0 mL) and tetrahydrofuran (2.5 mL) in a reaction container was deaerated, and the air inside the reaction container was replaced with argon. A solution of tetrakistriphenylphosphinepalladium(0) (46 mg, 0.04 mmol) in tetrahydrofuran (2.5 mL) was then added to the mixed liquid.

The thus obtained mixed liquid was stirred at 80° C. for 15 hours, and following cooling to room temperature, a saturated aqueous solution of sodium hydrogen carbonate was added to halt the reaction. The thus obtained organic layer was washed with water, dried using anhydrous sodium sulfate, and filtered. The filtrate was concentrated under reduced pressure, and the resulting residue was purified by silica gel column chromatography (hexane), yielding the title compound (2c) (270 mg, 0.45 mmol) as a white solid in a yield of 45%.

The results of NMR and the like are shown below.

$^1$H NMR (500 MHz, CDCl$_3$) δ 7.36 (d, 4H, J=7.5 Hz, Ar), 7.28 (d, 4H, J=8.0 Hz, Ar), 7.13 (d, 4H, J=7.5 Hz, Ar), 6.99 (s, 4H, CH=CH), 6.96 (d, 4H, J=7.5 Hz, Ar), 2.97 (dd, 2H, J=4.5, 14.0 Hz, CH$_2$Ar), 2.42 (dd, 2H, J=7.3, 13.8 Hz, CH$_2$Ar), 2.35 (s, 6H, ArCH$_3$), 2.11 (s br, 1H, CHCH$_2$Ar), 1.23 (s, 6H, (CH$_3$)$_2$C), 0.99 (t, 9H, J=7.5 Hz, (CH$_3$CH$_2$)$_3$Si), 0.63 (q, 6H, J=7.8 Hz, (CH$_3$CH$_2$)$_3$Si).

$^{13}$C NMR (CDCl$_3$, 150 MHz) δ 142.2, 137.1, 134.8, 134.7, 129.3, 128.4, 127.7, 127.5, 126.3, 126.1, 76.3, 54.9, 36.6, 28.3, 21.2, 7.2, 6.9.

IR (neat) 2961, 1606, 1516, 1456, 1416, 1384, 1261, 1016, 802.2 700.0 cm$^{-1}$.

HR-MS: m/z=calcd For C$_{42}$H$_{52}$NaOSi [M+Na]$^+$: 623.3685. found 623.3704.

Example 13

Synthesis of 4,4'-(1E,1'E)-2,2'-(4,4'-(2(2-(triethylsilyloxy)propan-2-yl)propan-1,3-diyl)bis(4,1-phenylene))bis(ethen-2,1-diyl)dipyridine (2d)

[Chemical Formula 41]

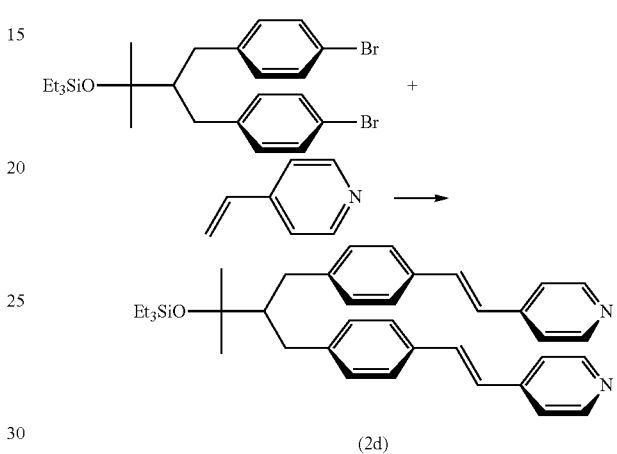

(2d)

A mixed liquid of (3-(4-bromobenzyl)-4-(4-bromophenyl)-2-methylbutan-2-yloxy)triethylsilane (526 mg, 1.0 mmol), 4-vinylpyridine (631 mg, 6.0 mmol), palladium(0) acetate (4.5 mg, 0.02 mmol), N,N-dimethyl-β-alanine (3.1 mg, 0.02 mmol), potassium carbonate (553 mg, 4.0 mmol) and N-methyl-2-pyrrolidone (4.0 mL) in a reaction container was deaerated, and the air inside the reaction container was replaced with argon.

The thus obtained mixed liquid was stirred at 130° C. for 2 days, and following cooling to room temperature, a saturated aqueous solution of sodium hydrogen carbonate was added to halt the reaction. The mixed liquid was then extracted with chloroform. The thus obtained organic layer was washed with water, dried using anhydrous sodium sulfate, and filtered. The filtrate was concentrated under reduced pressure, and the resulting residue was purified by silica gel column chromatography (acetone), yielding the title compound (2d) (201 mg, 0.35 mmol) as a yellow-brown viscous liquid in a yield of 35%.

The results of NMR and the like are shown below.

$^1$H NMR (600 MHz, CDCl$_3$) δ 8.53 (d, 4H, J=6.6 Hz, Ar), 7.31 to 7.29 (m, 8H, Ar), 7.22 (d, 2H, J=16.8 Hz, CH=CH), 6.99 (d, 4H, J=8.4 Hz, Ar), 6.90 (d, 2H, J=16.2 Hz, CH=CH), 3.02 (dd, 2H, J=4.8, 14.4 Hz, CH$_2$Ar), 2.43 (dd, 2H, J=8.1, 14.1 Hz, CH$_2$Ar), 2.16 to 2.12 (m, 1H, CHCH$_2$Ar), 1.25 (s, 6H, (CH$_3$)$_2$C), 1.00 (t, 91-1, J=8.4 Hz, (CH$_3$CH$_2$)$_3$Si), 0.64 (q, 6H, J=7.8 Hz, (CH$_3$CH$_2$)$_3$Si).

$^{13}$C NMR (CDCl$_3$, 150 MHz) δ 150.1, 144.8, 143.7, 133.3, 133.1, 129.5, 126.7, 124.9, 120.7, 76.2, 54.9, 45.5, 36.7, 28.2, 7.2, 6.9.

IR (neat) 3023, 2954, 2873, 1704, 1593, 1415, 1143, 1016, 822.5, 741.5, 725.1, 558.3 cm$^{-1}$.

HR-MS: m/z=calcd For $C_{38}H_{47}N_2OSi$ [M+H]$^+$: 575.3458. found 575.3457.

Example 14

Synthesis of triethyl(2-methyl-3-(3-(phenylethynyl)benzyl)-4-(3-(phenylethynyl)phenyl)butan-2-yloxy)silane (2e)

[Chemical Formula 42]

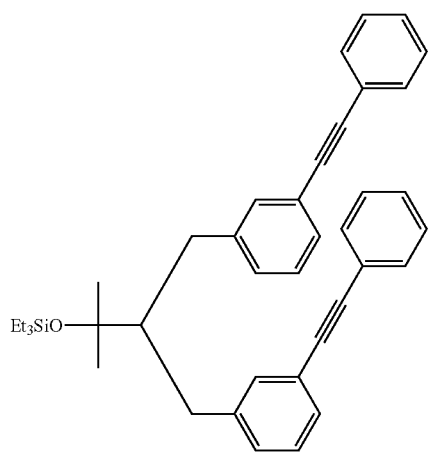

(2e)

A mixed liquid of (3-(3-bromobenzyl)-4-(3-bromophenyl)-2-methylbutan-2-ol (413 mg, 1.0 mmol), bis(triphenylphosphine)palladium(II) dichloride (70 mg, 0.10 mmol), copper iodide (19 mg, 0.10 mmol), triphenylphosphine (53 mg, 0.20 mmol), triethylamine (1.4 mL) and tetrahydrofuran (3.3 mL) in a reaction container was deaerated, and the air inside the reaction container was replaced with argon.

Ethynylbenzene (511 mg, 5.0 mmol) was added to the obtained mixed liquid, and the resulting mixture was stirred at 80° C. for 12 hours. The mixed liquid was then cooled to room temperature, and a saturated aqueous solution of ammonium chloride was added to halt the reaction. The thus obtained organic layer was washed with water, dried using anhydrous sodium sulfate, and filtered. The filtrate was concentrated under reduced pressure, and the resulting residue was purified by silica gel column chromatography (hexane:ethyl acetate=5:1), yielding a colorless liquid. Imidazole (136 mg, 2.0 mmol), triethylsilyl chloride (0.25 mL, 1.5 mmol) and N,N-dimethylformamide (5.0 mL) were then added to the liquid at 0° C.

Following stirring of the resulting mixed liquid at room temperature for 4 hours, a saturated aqueous solution of ammonium chloride was added to halt the reaction. The organic layer was separated from the mixed liquid, and the water layer was extracted with hexane. The resulting organic layer was washed with water, dried using anhydrous magnesium sulfate, and filtered. The filtrate was concentrated under reduced pressure, and the resulting residue was purified by silica gel column chromatography (hexane), yielding the title compound (2e) (409 mg, 0.72 mmol) as a yellow viscous solid in a yield of 72%.

The results of NMR and the like are shown below.

$^1$H NMR (600 MHz, CDCl$_3$) δ 7.52 to 7.50 (m, 4H, Ar), 7.31 to 7.30 (m, 6H, Ar), 7.25 (d, 2H, J=7.8 Hz, Ar), 7.16 (s, 2H, Ar), 7.10 (t, 2H, J=7.5 Hz, Ar), 6.92 (d, 2H, J=7.8 Hz, Ar), 3.01 (dd, 2H, J=4.2, 13.8 Hz, CH$_2$Ar), 2.41 (dd, 2H, J=8.4, 13.8 Hz, CH$_2$Ar), 2.14 to 2.10 (m, 1H, CHCH$_2$Ar), 1.27 (s, 6H, (CH$_3$)$_2$C), 1.00 (t, 9H, J=7.8 Hz, (CH$_3$CH$_2$)$_3$Si), 0.64 (q, 6H, J=7.8 Hz, (CH$_3$CH$_2$)$_3$Si).

$^{13}$C NMR (CDCl$_3$, 150 MHz) δ 142.6, 132.3, 131.6, 129.1, 128.7, 128.3, 128.0 (128.03, 128.00), 123.5, 122.8, 89.8, 88.8, 66.0, 54.7, 36.7, 28.2, 7.2, 6.9.

IR (neat) 3056, 2955, 2874, 1730, 1602, 1493, 1456, 1443, 1384, 1365, 1262, 1143, 1017, 783.9, 754.0, 689.4 cm$^{-1}$.

Example 15

Synthesis of triethyl(2-methyl-3-(3-styrylbenzyl)-4-(3-styrylphenyl)butan-2-yloxy)silane (2f)

[Chemical Formula 43]

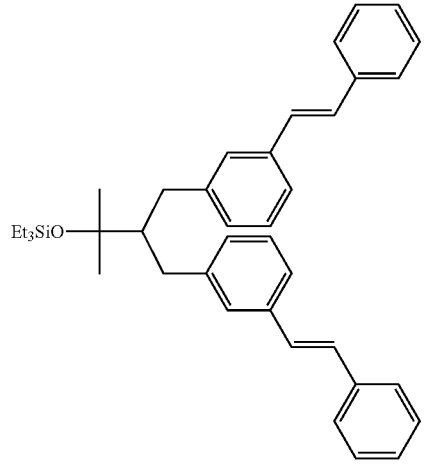

(2f)

A mixed liquid of (3-(3-bromobenzyl)-4-(3-bromophenyl)-2-methylbutan-2-ol (410 mg, 1.0 mmol), (E)-4,4,5,5-tetramethyl-2-styryl-1,3,2-dioxaborolane (690 mg, 3.0 mmol), a 2 M aqueous solution of potassium carbonate (1.0 mL) and tetrahydrofuran (2.5 mL) in a reaction container was deaerated, and the air inside the reaction container was replaced with argon. A solution of tetrakistriphenylphosphinepalladium(0) (46 mg, 0.04 mmol) in tetrahydrofuran (2.5 mL) was then added to the mixed liquid.

The thus obtained mixed liquid was stirred at 80° C. for 15 hours, and following cooling to room temperature, a saturated aqueous solution of sodium hydrogen carbonate was added to halt the reaction. The thus obtained organic layer was washed with water, dried using anhydrous sodium sulfate, and filtered. The filtrate was concentrated under reduced pressure, and the resulting residue was purified by silica gel column chromatography (hexane:ethyl acetate=5:1), yielding a colorless liquid. Imidazole (136 mg, 2.0 mmol), triethylsilyl chloride (0.25 mL, 1.5 mmol) and N,N-dimethylformamide (5.0 mL) were then added to the liquid at 0° C.

Following stirring of the resulting mixed liquid at room temperature for 4 hours, a saturated aqueous solution of ammonium chloride was added to halt the reaction. The organic layer was separated from the mixed liquid, and the water layer was extracted with hexane. The resulting organic layer was washed with water, dried using anhydrous magnesium sulfate, and filtered. The filtrate was concentrated under reduced pressure, and the resulting residue was purified by silica gel column chromatography (hexane), yielding the title compound (20 (223 mg, 0.39 mmol) as a colorless liquid in a yield of 39%.

The results of NMR and the like are shown below.

$^1$H NMR (600 MHz, CDCl$_3$) δ 7.44 (d, 4H, J=7.8 Hz, Ar), 7.30 (t, 4H, J=8.1 Hz, Ar), 7.23 (t, 2H, J=7.2 Hz, Ar), 7.19 (d, 2H, J=7.8 Hz, Ar), 7.11 (t, 2H, J=7.8 Hz, Ar), 7.06 (s, 2H, Ar), 6.97 (s, 2H, CH=CH), 6.96 (s, 2H, CH=CH), 6.91 (d, 2H, J=7.8 Hz, Ar), 3.04 (dd, 2H, J=4.5, 14.1 Hz, CH$_2$Ar), 2.37 (dd, 2H, J=8.1, 13.5 Hz, CH$_2$Ar), 2.18 to 2.14 (m, 1H, CHCH$_2$Ar), 1.30 (s, 6H, (CH$_3$)$_2$C), 1.01 (t, 9H, J=8.1 Hz, (CH$_3$CH$_2$)$_3$Si), 0.65 (q, 6H, J=7.8 Hz, (CH$_3$CH$_2$)$_3$Si).

$^{13}$C NMR (CDCl$_3$, 150 MHz) δ 143.0, 137.5, 136.9, 128.9, 128.6, 128.5, 128.3, 128.2, 128.2, 127.4, 127.3, 126.5, 123.8, 65.1, 55.1, 36.9, 28.2, 7.3, 6.9.

IR (neat) 3025, 2956, 2873, 1601, 1496, 1449, 1416, 1383, 1260, 1017, 800.3, 744.4, 725.1, 694.3 cm$^{-1}$.

Synthesis of Reactive Compounds (Monomers for Polymer Synthesis)

Example 16

Synthesis of ethyl 2-(4-bromobenzyl)-3-(4-bromophenyl)propanoate (4a)

[Chemical Formula 44]

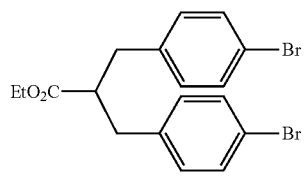

(4a)

Diethyl malonate (4.53 mL, 30.0 mmol) was added gradually at 0° C. to a mixed liquid containing sodium hydride (55 wt % in oil, 2.95 g, 67.5 mmol) and anhydrous dimethylformamide (60 mL). Following stirring of the resulting mixed liquid at this temperature for 30 minutes, 4-bromobenzyl bromide (15.7 g, 63.0 mmol) was added. The resulting mixed liquid was stirred at room temperature for 2 hours, and a saturated aqueous solution of ammonium chloride was then added to halt the reaction. The organic layer was separated from the mixed liquid, and the water layer was extracted with ethyl acetate. The thus obtained organic layer was washed with a saturated saline solution and then dried using anhydrous magnesium sulfate. The organic layer was then filtered, the filtrate was concentrated under reduced pressure, and to the resulting residue were added lithium chloride (5.09 g, 120 mmol), water (1.08 mL) and N,N-dimethylformamide (100 mL), thus forming a mixed liquid. The mixed liquid was heated for 7 hours at 160° C. The mixed liquid was then cooled to room temperature, water (100 mL) was added, and an extraction was performed with ethyl acetate.

The thus obtained organic layer was dried using anhydrous magnesium sulfate, and then filtered. The filtrate was concentrated under reduced pressure, and the resulting residue was purified by silica gel column chromatography (hexane:ethyl acetate=30:1), yielding the title compound (4a) (11.5 g, 27.0 mmol) as a light yellow liquid in a yield of 90%.

The results of NMR and the like are shown below.

$^1$H NMR (600 MHz, CDCl$_3$) δ 7.39 (d, 4H, J=8.4 Hz, Ar), 7.02 (d, 4H, J=7.8 Hz, Ar), 3.96 (q, 2H, J=7.4 Hz, CO$_2$CH$_2$CH$_3$), 2.92 to 2.85 (m, 3H, CHCH$_2$Ar and CHCH$_2$Ar), 2.73 (dd, 2H, J=4.8, 12.6 Hz, CH$_2$Ar), 1.03 (t, 3H, J=7.2 Hz, CO$_2$CH$_2$CH$_3$).

$^{13}$C NMR (150 MHz, CDCl$_3$) δ 174.3, 137.8, 131.5, 130.6, 120.4, 60.5, 49.2, 37.6, 14.0.

IR (neat) 2962, 1731, 1592, 1488, 1445, 1405, 1375, 1259, 1214, 1160, 1103, 1072, 1012, 806.1 cm$^{-1}$.

HR-MS: m/z=calcd For C$_{18}$H$_{18}$Br$_2$NaO$_2$ [M+Na]$^+$: 446.9571. found 446.9586.

Example 17

Synthesis of (3-(4-bromobenzyl)-4-(4-bromophenyl)-2-methylbutan-2-yloxy)triethylsilane (4b)

[Chemical Formula 45]

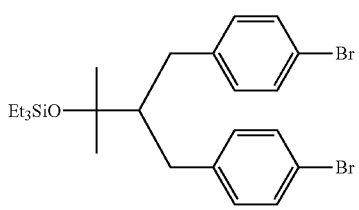

(4b)

A mixed liquid of anhydrous cerium(III) chloride (4.44 g, 18.0 mmol) and tetrahydrofuran (48 mL) was stirred at room temperature for 12 hours. This mixed liquid was cooled to −78° C., an ether solution of methyllithium (11.3 mL, 1.6 M, 18.0 mmol) was added, and the mixture was stirred for one hour.

To the resulting mixed liquid at −78° C. was added a solution of ethyl 2-(4-bromobenzyl)-3-(4-bromophenyl)propanoate (2.56 g, 6.00 mmol) in tetrahydrofuran (6 mL), and the resulting mixture was stirred for 2 hours. Following addition of a 0.1 M aqueous solution of acetic acid (10 mL) to the mixed liquid to halt the reaction, the mixture was extracted with ethyl acetate. The thus obtained organic layer was washed with water, dried using anhydrous sodium sulfate, and then filtered. The filtrate was concentrated under reduced pressure, and pyridine (12 mL) and triethylsilyl chloride (1.3 mL, 7.5 mmol) were added to the resulting residue at room temperature to form a mixed liquid.

This mixed liquid was stirred at 60° C. for 20 hours. The mixed liquid was then cooled to room temperature, and a saturated aqueous solution of ammonium chloride was added to halt the reaction. The organic layer was separated from the mixed liquid, and the water layer was extracted with hexane. The thus obtained organic layer was washed with water, dried using anhydrous magnesium sulfate, and filtered. The filtrate was concentrated under reduced pressure, and the resulting residue was purified by silica gel column chromatography (hexane), yielding the title compound (4b) (3.00 g, 5.7 mmol) as a colorless liquid in a yield of 95%.

The results of NMR and the like are shown below.

$^1$H NMR (600 MHz, CDCl$_3$) δ 7.25 (d, 4H, J=8.4 Hz, Ar), 6.81 (d, 4H, J=8.4 Hz, Ar), 2.92 (dd, 2H, J=4.8, 14.4 Hz, CH$_2$Ar), 2.30 (dd, 2H, J=8.1, 14.1 Hz, CH$_2$Ar), 2.00 (tt, 1H, J=4.3, 8.4 Hz, CHCH$_2$Ar), 1.21 (s, 6H, (CH$_3$)$_2$C), 0.97 (t, 9H, J=7.8 Hz, (CH$_3$CH$_2$)$_3$Si), 0.61 (q, 6H, J=8.0 Hz, (CH$_3$CH$_2$)$_3$Si).

$^{13}$C NMR (150 MHz, CDCl$_3$) δ 141.4, 131.1, 130.6, 119.1, 76.1, 54.9, 36.2, 28.2, 7.2, 6.9.

IR (neat) 2954, 2874, 1591, 1488, 1459, 1404, 1383, 1365, 1236, 1178, 1143, 1102, 1072, 1012, 798.4, 724.1 cm$^{-1}$.

HR MS: m/z=calcd For C$_{24}$H$_{34}$Br$_2$KOSi [M+K]$^+$: 563.0383. found 563.0352.

Example 18

Synthesis of diethyl 2,2-bis(3-bromobenzyl)malonate (4c)

[Chemical Formula 46]

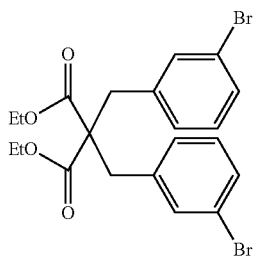

(4c)

Diethyl malonate (4.53 mL, 30.0 mmol) was added gradually at 0° C. to a mixed liquid containing sodium hydride (55 wt % in oil, 2.95 g, 67.5 mmol) and anhydrous dimethylsulfoxide (60 mL). Following stirring of the resulting mixed liquid at this temperature for 30 minutes, 3-bromobenzyl bromide (15.7 g, 63.0 mmol) was added. The resulting mixed liquid was stirred at room temperature for 2 hours, and a saturated aqueous solution of ammonium chloride was then added to halt the reaction. The organic layer was separated from the mixed liquid, and the water layer was extracted with ethyl acetate. The thus obtained organic layer was washed with a saturated saline solution and then dried using anhydrous magnesium sulfate. The organic layer was then filtered, the filtrate was concentrated under reduced pressure, and the resulting residue was purified by silica gel column chromatography (hexane:ethyl acetate=70:1), yielding the title compound (4c) (12.7 g, 25.5 mmol) as a white solid in a yield of 85%.

The results of NMR and the like are shown below.

$^1$H NMR (600 MHz, CDCl$_3$) δ 7.38 (d, 2H, J=7.2 Hz, Ar), 7.30 (s, 2H, Ar), 7.15 (t, 2H, J=7.8 Hz, Ar), 7.10 (d, 2H, J=7.8 Hz, Ar), 4.13 (q, 4H, J=7.0 Hz, CH$_3$CH$_2$), 3.16 (s, 4H, CH$_2$Ar), 1.18 (t, 6H, J=7.2 Hz, CH$_3$CH$_2$).

$^{13}$C NMR (CDCl$_3$, 150 MHz) δ 170.4, 138.4, 133.2, 130.1, 129.8, 128.7, 122.3, 61.5, 60.0, 39.2, 13.9.

IR (neat) 3063, 2980, 2934, 2872, 1730, 1594, 1568, 1474, 1261, 1196, 1180, 1073, 1043, 785.9, 694.3 cm$^{-1}$.

Example 19

Synthesis of (3-(3-bromobenzyl)-4-(3-bromophenyl)-2-methylbutan-2-ol (4d)

[Chemical Formula 47]

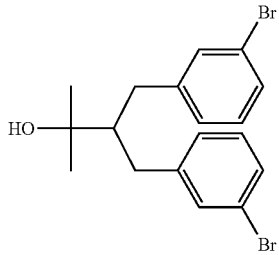

(4d)

A mixed liquid of diethyl 1,2-bis(3-bromobenzyl)malonate (3.0 g 6.0 mmol), lithium chloride (1.0 g, 24 mmol), water (0.22 mL) and N,N-dimethylformamide (20 mL) in a reaction container was deaerated, and the air inside the reaction container was replaced with argon.

The thus obtained mixed liquid was heated for 7 hours at 160° C. The mixed liquid was then cooled to room temperature, water (20 mL) was added, and the mixture was extracted with ethyl acetate. The thus obtained organic layer was dried using anhydrous magnesium sulfate, and then filtered. The filtrate was concentrated under reduced pressure, and the resulting residue was purified by silica gel column chromatography (hexane:ethyl acetate=70:1), yielding a light yellow liquid.

Meanwhile, a mixed liquid of anhydrous cerium(III) chloride (4.44 g, 18.0 mmol) and tetrahydrofuran (48 mL) was stirred at room temperature for 12 hours, and following subsequent cooling to −78° C., an ether solution of methyllithium (11.3 mL, 1.6 M, 18.0 mmol) was added, and the mixture was stirred for one hour. To the resulting mixed liquid at −78° C. was added a solution of the above-prepared light yellow liquid in tetrahydrofuran (6.0 mL), and the resulting mixture was stirred for 2 hours. Following addition of a 0.1 M aqueous solution of acetic acid (10 mL) to the mixed liquid to halt the reaction, the mixture was extracted with ethyl acetate. The thus obtained organic layer was washed with water, dried using anhydrous sodium sulfate, and then filtered. The filtrate was concentrated under reduced pressure, and the residue was purified by silica gel column chromatography (hexane:ethyl acetate=5:1), yielding the title compound (4d) (1.33 g, 3.24 mmol) as a colorless liquid in a yield of 54%.

The results of NMR and the like are shown below.

$^1$H NMR (600 MHz, CDCl$_3$) δ 7.22 (d, 2H, J=7.8 Hz, Ar), 7.10 (s, 2H, Ar), 7.03 (t, 2H, J=7.5 Hz, Ar), 6.92 (d, 2H, J=7.2 Hz, Ar), 2.94 (dd, 2H, J=4.2, 14.4 Hz, CH$_2$Ar), 2.37 (dd, 2H, J=8.4, 13.8 Hz, CH$_2$Ar), 2.12 to 2.08 (m, 1H, CHCH$_2$Ar), 1.28 (s, 6H, (CH$_3$)$_2$C).

$^{13}$C NMR (CDCl$_3$, 150 MHz) δ 144.0, 132.0, 129.7, 128.9, 127.5, 122.3, 73.7, 53.6, 36.6, 27.6.

IR (neat) 3427, 3059, 2970, 2932, 1593, 1567, 1473, 1424, 1384, 1070, 996.1, 776.2, 691.4 cm$^{-1}$.

HR-MS: m/z=calcd For $C_{26}H_{36}KO_3Si$ [M+K]$^+$: 463.2071. found 463.2087.

Example 20

Synthesis of 4,4'-(2-(2-(triethylsilyloxy)propan-2-yl)propan-1,3-diyl)dibenzaldehyde (4e)

[Chemical Formula 48]

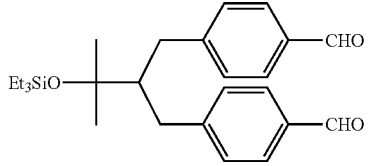

(4e)

A hexane solution of π-butyllithium (4.4 mL, 1.57 M, 6.9 mmol) was added gradually at −40° C. to a mixed liquid containing (3-(4-bromobenzyl)-4-(4-bromophenyl)-2-methylbutan-2-yloxy)triethylsilane (1.58 g, 3.0 mmol) and diethyl ether (10 mL). The mixed liquid was stirred at this temperature for one hour, and was then stirred at 0° C. for 2 hours.

Anhydrous dimethylformamide (0.7 mL, 9.0 mmol) was added gradually at 0° C. to the obtained mixed liquid, and the resulting mixture was stirred for 12 hours. A saturated aqueous solution of ammonium chloride was added to the mixed liquid to halt the reaction, and the mixed liquid was then extracted with ethyl acetate. The thus obtained organic layer was washed with water, dried using anhydrous sodium sulfate, and then filtered. The filtrate was concentrated under reduced pressure, and the resulting residue was purified by silica gel column chromatography (hexane:ethyl acetate=10:1), yielding the title compound (4e) (1.17 g, 2.8 mmol) as a light yellow viscous liquid in a yield of 92%.

The results of NMR and the like are shown below.

$^1$H NMR (600 MHz, CDCl$_3$) δ 9.89 (s, 2H, CHO), 7.62 (d, 4H, J=7.8 Hz, Ar), 7.11 (d, 4H, J=7.8 Hz, Ar), 3.11 (dd, 2H, J=4.5, 14.1 Hz, CH$_2$Ar), 2.46 (dd, 2H, J=8.4, 14.4 Hz, CH$_2$Ar), 2.22 to 2.17 (m, 1H, CHCH$_2$Ar), 1.27 (s, 6H, (CH$_3$)$_2$C), 0.98 (t, 9H, J=7.8 Hz, (CH$_3$CH$_2$)$_3$Si), 0.62 (q, 6H, J=7.6 Hz, (CH$_3$CH$_2$)$_3$Si).

$^{13}$C NMR (CDCl$_3$, 150 MHz) δ 191.8, 149.9, 134.2, 129.6, 129.5, 75.9, 54.6, 37.3, 28.0, 7.2, 6.8.

IR (neat) 2954, 2875, 2823, 2731, 1702, 1606, 1575, 1459, 1417, 1385, 1366, 1306, 1213, 1169, 1143, 1107, 1041, 1016, 822.5, 779.1, 742.5 cm$^{-1}$.

Example 21

Synthesis of triethyl(3-(4-ethynylbenzyl)-4-(4-ethynylphenyl)-2-methylbutan-2-yloxy)silane (4f)

[Chemical Formula 49]

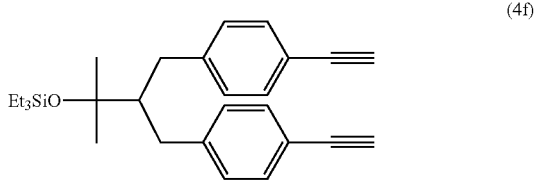

(4f)

A mixed liquid of (3-(4-bromobenzyl)-4-(4-bromophenyl)-2-methylbutan-2-yloxy)triethylsilane (1.58 g, 3.0 mmol), dichlorobis(triphenylphosphine)palladium(II) (168 mg, 0.24 mmol), copper iodide (46 mg, 0.24 mmol), triphenylphosphine (126 mg, 0.48 mmol), tetrahydrofuran (14 mL) and triethylamine (6.0 mL) in a reaction container was deaerated, and the air inside the reaction container was replaced with argon. To this mixed liquid was added trimethylsilylacetylene (884 mg, 9.0 mmol).

Following stirring of the thus obtained mixed liquid at 80° C. for 15 hours, the temperature was cooled to room temperature, and a saturated aqueous solution of ammonium chloride was added to halt the reaction. The mixed liquid was extracted with hexane, and the resulting organic layer was washed with water, dried using anhydrous magnesium sulfate, and filtered. The filtrate was concentrated under reduced pressure, and the resulting residue was purified by silica gel column chromatography (hexane). To the thus obtained brown liquid were added potassium carbonate (830 mg, 6.0 mmol), methanol (6.0 mL) and tetrahydrofuran (3.0 mL), and the mixture was stirred for 2 hours at room temperature to obtain a mixed liquid. A saturated aqueous solution of sodium hydrogen carbonate was added to the mixed liquid, and the mixture was then extracted with hexane. The thus obtained organic layer was dried using anhydrous magnesium sulfate, and then filtered. The filtrate was concentrated under reduced pressure, and the resulting residue was purified by silica gel column chromatography (hexane), yielding the title compound (40 (1.03 g, 2.5 mmol) as a brown liquid in a yield of 82%.

The results of NMR and the like are shown below.

$^1$H NMR (600 MHz, CDCl$_3$) δ 7.28 (d, 4H, J=8.4 Hz, Ar), 6.92 (d, 4H, J=7.8 Hz, Ar), 3.01 (s, 2H, ArCCH), 2.96 (dd, 2H, J=4.8, 14.4 Hz, CH$_2$Ar), 2.39 (dd, 2H, J=7.8, 13.8 Hz, CH$_2$Ar), 2.08 to 2.04 (m, 1H, CHCH$_2$Ar), 1.20 (s, 6H, (CH$_3$)$_2$C), 0.97 (t, 9H, J=7.8 Hz, (CH$_3$CH$_2$)$_3$Si), 0.61 (q, 6H, J=7.8 Hz, (CH$_3$CH$_2$)$_3$Si).

$^{13}$C NMR (150 MHz, CDCl$_3$) δ 143.6, 131.9, 128.9, 119.0, 83.8, 76.4, 76.1, 54.7, 36.7, 28.2, 7.2, 6.8.

IR (neat) 3297, 2955, 2874, 1731, 1606, 1505, 1462, 1413, 1384, 1366, 1237, 1177, 1144, 1013, 743.4 cm$^{-1}$. HR-MS: m/z=calcd For $C_{28}H_{36}NaOSi$ [M+Na]$^+$: 439.2433. found 439.2414.

Example 22

Synthesis of triethyl(2-methyl-3-(4-((E)-2-(4,4,5,5-tetramethyl-1,3,2-dioxaborolan-2-yl)vinyl)benzyl)-4-(4-((E)-2-(4,4,5,5-tetramethyl-1,3,2-dioxaborolan-2-yl)vinyl)phenyl)butan-2-yloxy)silane (4g)

[Chemical Formula 50]

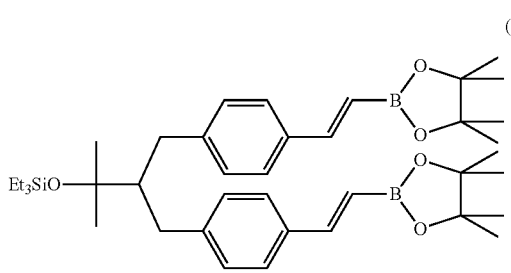

(4g)

A mixed liquid containing 2,5-dimethyl-2,4-hexadiene (1.14 mL, 8.0 mmol), a tetrahydrofuran solution of borane (4.4 mL, 0.9 M, 4.0 mmol) and tetrahydrofuran (4.0 mL) was prepared at 0° C., and the mixed liquid was stirred at this temperature for 3 hours.

To the thus obtained mixed liquid was added a solution of triethyl(3-(4-ethnylbenzyl)-4-(4-ethynylphenyl)-2-methylbutan-2-yloxy)silane (420 mg, 1.0 mmol) in tetrahydrofuran (2.5 mL), and the resulting mixture was stirred at 0° C. for 2 hours. Water (0.52 mL) was then added to the mixed liquid at room temperature, and following stirring for one hour, an aqueous solution of formaldehyde (0.75 mL, 37 wt %, 10 mmol) was added and stirred for 30 minutes. To the resulting mixed liquid was added a solution of 2,2-dimethyl-1,3-propanediol (230 mg, 2.2 mmol) in tetrahydrofuran (1.0 mL), and the resulting mixture was stirred for 24 hours. Water was added to the mixed liquid to halt the reaction, and an extraction was then performed with ethyl acetate.

The thus obtained organic layer was washed with water, dried using anhydrous magnesium sulfate, and filtered. Following filtering of the organic layer, the filtrate was concentrated under reduced pressure, and the resulting residue was purified twice by silica gel column chromatography (hexane:ethyl acetate=60:1), yielding the title compound (4g) (251 mg, 0.39 mmol) as a colorless viscous solid in a yield of 39%.

The results of NMR and the like are shown below.

$^1$H NMR (500 MHz, CDCl$_3$) δ 7.29 to 7.24 (m, 6H, Ar and CH=CH), 6.95 (d, 4H, J=8.0 Hz, Ar), 6.00 (d, 2H, J=17.0 Hz, CH=CH), 3.69 (s, 8H, OCH$_2$), 2.92 (dd, 2H, J=5.0, 14.0 Hz, CH$_2$Ar), 2.41 (dd, 2H, J=7.5, 14.0 Hz, CH$_2$Ar), 2.09 to 2.07 (m, 1H, CHCH$_2$Ar), 1.18 (s, 6H, Et$_3$SiOC(CH$_3$)$_2$C), 1.00 (s, 12H, (CH$_3$)$_2$C), 0.96 (t, 9H, J=7.8 Hz, (CH$_3$CH$_2$)$_3$Si), 0.59 (q, 6H, J=7.8 Hz, (CH$_3$CH$_2$)$_3$Si).

IR (neat) 3418, 2980, 2932, 2873, 1731, 1622, 1367, 1255, 1186, 754.0 cm$^{-1}$.

Synthesis of Polymer Compounds

Example 23

Synthesis of poly-[CH$_2$—CH(C(CH$_3$)$_2$OSi(CH$_2$CH$_3$)$_3$)—CH$_2$-1,4-(phenylene)-2,5-(thiophenylene)-2,5-(thiophenylene)-1,4-(phenylene)] (3a) (Pd-catalyst, Suzuki-Miyaura coupling)

[Chemical Formula 51]

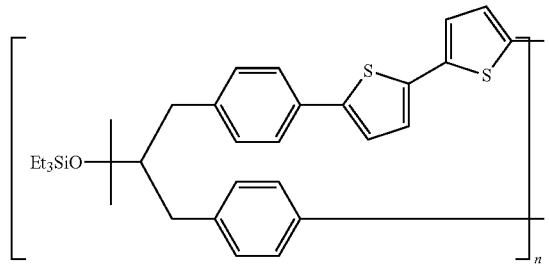

(3a)

A mixed liquid of the (3-(4-bromobenzyl)-4-(4-bromophenyl)-2-methylbutan-2-yloxy)triethylsilane (4b) (2.11 g, 4.0 mmol) obtained in the example 17, 5,5'-bis(4,4,5,5-tetramethyl-1,3,2-dioxaborolan-2-yl)-2,2'-bithiophene (1.67 g, 4.0 mmol), tri-n-octylmethylammonium chloride (330 mg, 0.82 mmol), a 2 M aqueous solution of sodium carbonate (8.0 mL) and tetrahydrofuran (22 mL) in a reaction container was deaerated, and the air inside the reaction container was replaced with argon. A solution containing tetrakistriphenylphosphinepalladium(0) (185 mg, 0.16 mmol) in tetrahydrofuran (5 mL) was added to the mixed liquid.

Following stirring of the resulting mixed liquid at 80° C. for 3 days, the temperature was cooled to room temperature, and a saturated aqueous solution of sodium hydrogen carbonate was added to halt the reaction. The mixed liquid was extracted with chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into ethyl acetate, the polymer compound precipitated as a solid. This solid was collected by filtration, washed with ethyl acetate, and then dried under reduced pressure, yielding the title polymer compound (3a) (1.68 g) as a dark brown solid in a yield of 79%.

The results of NMR and the like are shown below.

GPC (solvent: THF, standard: poly-styrene: $M_n$=7.03×10$^3$, $M_w$=1.01×10$^4$, $M_w/M_n$=1.44.

Based on this result, it can be determined that n=13 in the formula 3a. Similarly, for other polymer compounds obtained in the examples, the value of n can be calculated by dividing the Mn value determined by GPC by the molecular weight of the repeating unit.

$^1$H NMR (CDCl$_3$, 600 MHz) δ 7.42 to 6.70 (br m, overlap with CHCl$_3$ peak, 12H in one unit, Ar), 3.08 to 2.89 (br, 2H in one unit, CH$_2$Ar), 2.43 to 2.24 (br, 2H in one unit, CH$_2$Ar), 2.19 to 2.08 (br, 1H in one unit, CHCH$_2$Ar), 1.36 to 1.13 (br, 6H in one unit, (CH$_3$)$_2$C), 1.07 to 0.86 (br, 9H in one unit, (CH$_3$CH$_2$)$_3$Si), 0.73 to 0.47 (br, 6H in one unit, (CH$_3$C$_{1-12}$)$_3$Si).

$^{13}$C NMR (CDCl$_3$, 150 MHz) δ 142.9, 141.9, 136.2, 135.7, 131.2, 129.4, 127.7, 125.5, 125.1, 124.2, 123.2, 76.1, 54.9, 36.7, 34.2, 30.3, 29.4, 28.1, 7.3, 6.9.

IR (film) 2954, 2875, 1497, 1445, 1415, 1382, 1364, 1215, 1177, 1144, 1112, 1040, 790.7, 740.5 cm$^{-1}$.

Example 24

Synthesis of poly-[CH$_2$—CH(C(CH$_3$)$_2$OSi(CH$_2$CH$_3$)$_3$)—CH$_2$-1,4-(phenylene)-(E)-1,2-(ethenylene)-1,4-(phenylene)-(E)-1,2-(ethenylene)-1,4-(phenylene)] (3b) (Pd-catalyst, Suzuki-Miyaura coupling)

[Chemical Formula 52]

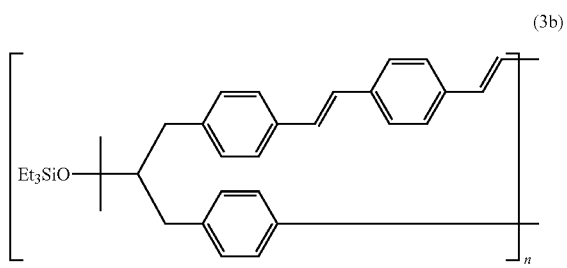

(3b)

(Synthesis by Suzuki-Miyaura coupling reaction): A mixed liquid of the (3-(4-bromobenzyl)-4-(4-bromophenyl)-2-methylbutan-2-yloxy)triethylsilane (4b) (790 mg, 1.50 mmol) obtained in the example 17, 1,4-bis((E)-2-(4,4,5,5-tetramethyl-1,3,2-dioxaborolan-2-yl)vinyl)benzene (537 mg, 1.50 mmol), tetra-n-butylammonium bromide (484 mg, 1.50 mmol), a 2 M aqueous solution of potassium carbonate (3.0 mL) and tetrahydrofuran (8 mL) in a reaction container was deaerated, and the air inside the reaction container was replaced with argon. A solution containing tetrakistriphenylphosphinepalladium(0) (69 mg, 0.060 mmol) in tetrahydrofuran (2 mL) was added to the mixed liquid.

Following stirring of the resulting mixed liquid at 80° C. for 3 days, the temperature was cooled to room temperature, and a saturated aqueous solution of sodium hydrogen carbonate was added to halt the reaction. The mixed liquid was extracted with chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into methanol, the polymer compound precipitated as a solid. This solid was collected by filtration, washed with diethyl ether, and then dried under reduced pressure, yielding the title polymer compound (3b) (371 mg) as a yellow-brown solid in a yield of 50%.

The results of NMR and the like are shown below.

GPC (solvent: THF, standard: poly-styrene: M$_n$=7.14×10$^3$, M$_w$=1.20×10$^4$, M$_w$/M$_n$=1.68.

$^1$H NMR (CDCl$_3$, 600 MHz) δ 7.44 to 6.81 (br m, overlap with CHCl$_3$ peak, 16H, Ar and CH=CH), 3.13 to 2.77 (br, 2H, CH$_2$Ar), 2.48 to 2.23 (br, 2H, CH$_2$Ar), 2.16 to 2.00 (br, 1H, CH$_2$Ar), 1.35 to 1.04 (br, 6H, (CH$_3$)$_2$C), 1.04 to 0.83 (br, 9H, (CH$_3$CH$_2$)$_3$Si), 0.71 to 0.48 (br, 6H, (CH$_3$CH$_2$)$_3$Si).

$^{13}$C NMR (CDCl$_3$, 150 MHz) δ 142.3, 136.6, 134.5, 129.3, 128.7, 128.4, 127.3, 126.7, 126.5, 126.2, 76.2, 54.9, 36.6, 28.3, 7.3, 6.9.

IR (film) 3021, 2954, 2875, 1600, 1516, 1459, 1419, 1383, 1364, 1212, 1177, 1144, 1110, 1040, 960.4, 825.4, 724.1, 549.6 cm$^{-1}$.

Example 25

Synthesis of poly-[CH$_2$—CH(C(CH$_3$)$_2$OSi(CH$_2$CH$_3$)$_3$)—CH$_2$-1,4-(phenylene)-(E)-1,2-(ethenylene)-1,4-(phenylene)-(E)-1,2-(ethenylene)-1,4-(phenylene)] (3c) (Pd-catalyst, synthesis by Mizoroki-Heck reaction)

[Chemical Formula 53]

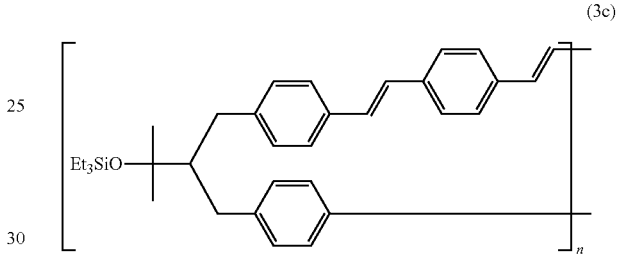

(3c)

A mixed liquid of the (3-(4-bromobenzyl)-4-(4-bromophenyl)-2-methylbutan-2-yloxy)triethylsilane (4b) (263 mg, 0.50 mmol) obtained in the example 17, 1,4-divinylbenzene (65 mg, 0.50 mmol), palladium(II) acetate (4.5 mg, 0.020 mmol), tri-ortho-tolylphosphine (36.5 mg, 0.12 mmol), anhydrous dimethylformamide (3.9 mL) and tributylamine (1.5 mL) in a reaction container was deaerated, and the air inside the reaction container was replaced with argon.

Following stirring of the thus obtained mixed liquid at 110° C. for 2 days, the temperature was cooled to room temperature, and a saturated aqueous solution of sodium hydrogen carbonate was added to halt the reaction. The mixed liquid was extracted using chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into methanol, the polymer compound precipitated as a solid. This solid was collected by filtration, washed with hexane, and then dried under reduced pressure, yielding the title polymer compound (3c) (162 mg, 0.33 mmol) as a yellow-brown solid in a yield of 66%.

The results of NMR and the like are shown below.

GPC (solvent: THF, standard: poly-styrene: M$_n$=3.04×10$^3$, M$_w$=5.28×10$^3$, M$_w$/M$_n$=1.74.

$^1$H NMR (CDCl$_3$, 600 MHz) δ 7.44 to 6.81 (br m, overlap with CHCl$_3$ peak, 16H, Ar and CH=CH), 3.13 to 2.77 (br, 2H, CH$_2$Ar), 2.48 to 2.23 (br, 2H, CH$_2$Ar), 2.16 to 2.00 (br, 1H, CH$_2$Ar), 1.35 to 1.04 (br, 6H, (CH$_3$)$_2$C), 1.04 to 0.83 (br, 9H, (CH$_3$CH$_2$)$_3$Si), 0.71 to 0.48 (br, 6H, (CH$_3$CH$_2$)$_3$Si).

$^{13}$C NMR (CDCl$_3$, 150 MHz) δ 142.3, 136.6, 134.5, 129.3, 128.7, 128.4, 127.3, 126.7, 126.5, 126.2, 76.2, 54.9, 36.6, 28.3, 7.3, 6.9.

IR (film) 3021, 2954, 2875, 1600, 1516, 1459, 1419, 1383, 1364, 1212, 1177, 1144, 1110, 1040, 960.4, 825.4, 724.1, 549.6 cm$^{-1}$.

Example 26

Synthesis of poly-[CH$_2$—CH(C(CH$_3$)$_2$OSi(CH$_2$CH$_3$)$_3$)—CH$_2$-1,4-(phenylene)-1,4-(phenylene)-1,4-(phenylene)] (3d) (Pd-catalyst, Suzuki-Miyaura coupling)

[Chemical Formula 54]

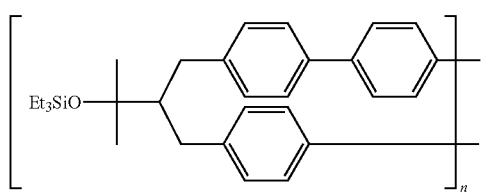

(3d)

A mixed liquid of the (3-(4-bromobenzyl)-4-(4-bromophenyl)-2-methylbutan-2-yloxy)triethylsilane (4b) (2.11 g, 4.0 mmol) obtained in the example 17, 1,4-bis(4,4,5,5-tetramethyl-1,3,2-dioxaborolan-2-yl)benzene (1.32 g, 4.0 mmol), tri-n-octylmethylammonium chloride (330 mg, 0.82 mmol), a 2 M aqueous solution of sodium carbonate (8.0 mL) and tetrahydrofuran (22 mL) in a reaction container was deaerated, and the air inside the reaction container was replaced with argon. A solution containing tetrakistriphenylphosphinepalladium(0) (185 mg, 0.16 mmol) in tetrahydrofuran (5.0 mL) was added to the mixed liquid.

Following stirring of the resulting mixed liquid at 80° C. for 3 days, the temperature was cooled to room temperature, and a saturated aqueous solution of sodium hydrogen carbonate was added to halt the reaction. The mixed liquid was extracted using chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into methanol, the polymer compound precipitated as a solid. This solid was collected by filtration and dried under reduced pressure, yielding the title polymer compound (3d) (1.01 g, 2.3 mmol) as a white solid in a yield of 57%.

The results of NMR and the like are shown below.

GPC (solvent: THF, standard: poly-styrene: $M_n$=2.50×10$^3$, $M_w$=4.29×10$^3$, $M_w/M_n$=1.72.

$^1$H NMR (CDCl$_3$, 600 MHz) δ 7.72 to 6.65 (br m, overlap with CHCl$_3$ peak, 12H, Ar), 3.16 to 2.87 (br, 2H, CH$_2$Ar), 2.54 to 1.98 (br, 3H, CH$_2$Ar and CHCH$_2$Ar), 1.40 to 1.06 (br, 6H, (CH$_3$)$_2$C), 1.06 to 0.79 (br, 9H, (CH$_3$CH$_2$)$_3$Si), 0.71 to 0.47 (br, 6H, (CH$_3$CH$_2$)$_3$Si).

$^{13}$C NMR (CDCl$_3$, 150 MHz) δ 141.8, 139.6, 137.7, 130.9, 130.7, 129.4, 128.7, 127.1, 126.5, 76.3, 54.9, 36.5, 28.3, 7.3, 6.9.

IR (film) 2958, 2873, 1491, 1384, 1260, 1018, 802.2, 741.5 cm$^{-1}$.

Example 27

Synthesis of poly-[CH$_2$—CH(C(CH$_3$)$_2$OSi(CH$_2$CH$_3$)$_3$)—CH$_2$-1,4-(phenylene)-(E)-1,2-(ethenylene)-2,7-(9H-fluorenylene)-(E)-1,2-(ethenylene)-1,4-(phenylene)] (3e) (Pd-catalyst, Suzuki-Miyaura coupling)

[Chemical Formula 55]

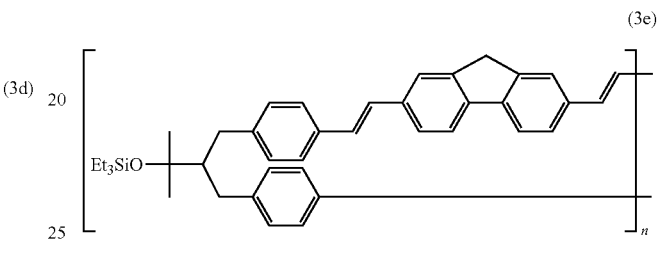

(3e)

A mixed liquid of the (3-(4-bromobenzyl)-4-(4-bromophenyl)-2-methylbutan-2-yloxy)triethylsilane (4b) (790 mg, 1.50 mmol) obtained in the example 17, 2,7-bis(4,4,5,5-tetramethyl-1,3,2-dioxaborolan-2-yl)-9H-fluorene (627 mg, 1.50 mmol), tetra-n-butylammonium bromide (484 mg, 1.50 mmol), a 2 M aqueous solution of potassium carbonate (3.0 mL) and tetrahydrofuran (8 mL) in a reaction container was deaerated, and the air inside the reaction container was replaced with argon. A solution containing tetrakistriphenylphosphinepalladium(0) (69 mg, 0.060 mmol) in tetrahydrofuran (2.0 mL) was added to the mixed liquid.

Following stirring of the resulting mixed liquid at 80° C. for 3 days, the temperature was cooled to room temperature, and a saturated aqueous solution of sodium hydrogen carbonate was added to halt the reaction. The mixed liquid was extracted using chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into methanol, the polymer compound precipitated as a solid. This solid was collected by filtration, washed with diethyl ether, and then dried under reduced pressure, yielding the title polymer compound (3e) (437 mg, 0.75 mmol) as a red-brown solid in a yield of 50%.

The results of NMR and the like are shown below.

GPC (solvent: THF, standard: poly-styrene: $M_n$=4.21×10$^3$, $M_w$=7.69×10$^3$, $M_w/M_n$=1.83.

$^1$H NMR (CDCl$_3$, 600 MHz) δ 7.81 to 6.43 (br m, overlap with CHCl$_3$ peak, 18H, Ar and CH=CH), 3.95 to 3.30 (br, 2H, ArCH$_2$Ar), 3.17 to 2.69 (br, 2H, CH$_2$Ar), 2.51 to 2.00 (br, 3H, CH$_2$Ar and CHCH$_2$Ar), 1.42 to 1.09 (br, 6H, (CH$_3$)$_2$C), 1.07 to 0.78 (br, 9H, (CH$_3$CH$_2$)$_3$Si), 0.73 to 0.45 (br, 61-1, (CH$_3$CH$_2$)$_3$Si).

$^{13}$C NMR (CDCl$_3$, 150 MHz) δ 144.0, 141.0, 131.0, 130.7, 129.3, 128.0, 127.9, 126.3, 126.2, 126.1, 125.6, 122.7, 120.0, 119.9, 76.2, 54.9, 39.0, 36.7, 28.2, 7.3, 6.9.

IR (film) 2957, 2874, 1602, 1384, 1261, 1018, 962.3, 802.2, 723.2 cm$^{-1}$.

Example 28

Synthesis of poly-[CH$_2$—CH(C(CH$_3$)$_2$OSi(CH$_2$CH$_3$)$_3$)—CH$_2$-1,4-(phenylene)-(ethynylene)-1,4-(phenylene)-(ethynylene)-1,4-(phenylene)] (3f) (Pd-catalyst, Sonogashira coupling)

[Chemical Formula 56]

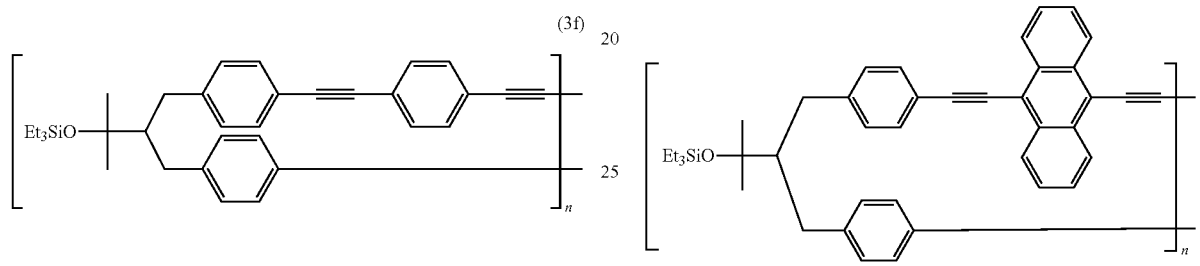

(3f)

A mixed liquid of the triethyl(3-(4-ethynylbenzyl)-4-(4-ethynylphenyl)-2-methylbutan-2-yloxy)silane (40 (208.3 mg, 0.50 mmol) obtained in the example 21, 1,4-diiodobenzene (165.0 mg, 0.50 mmol), tetrakistriphenylphosphine-palladium(0) (57.8 mg, 0.050 mmol), copper iodide (9.5 mg, 0.050 mmol), tetrahydrofuran (5.0 mL) and triethylamine (2.5 mL) in a reaction container was deaerated, and the air inside the reaction container was replaced with argon.

Following stirring of the resulting mixed liquid at 80° C. for 3 days, the temperature was cooled to room temperature, and a saturated aqueous solution of sodium hydrogen carbonate was added to halt the reaction. The mixed liquid was extracted using chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into methanol, the polymer compound precipitated as a solid. This solid was collected by filtration, washed with hexane, and then dried under reduced pressure, yielding the title polymer compound (30 (230.7 mg, 0.47 mmol) as a yellow-brown solid in a yield of 94%.

The results of NMR and the like are shown below.

GPC (solvent: THF, standard: poly-styrene: $M_n$=4.44×10$^3$, $M_w$=8.11×10$^3$, $M_w/M_n$=1.83.

$^1$H NMR (CDCl$_3$, 600 MHz) δ 7.55 to 7.16 (br m, overlap with CHCl$_3$ peak, 8H, Ar), δ 7.04 to 6.87 (br m, 4H, Ar), 3.04 to 2.92 (br, 2H, CH$_2$Ar), 2.46 to 2.35 (br, 2H, CH$_2$Ar), 2.14 to 2.03 (br, 1H, CHCH$_2$Ar), 1.32 to 1.15 (br, 6H, (CH$_3$)$_2$C), 1.04 to 0.87 (br, 9H, (CH$_3$CH$_2$)$_3$Si), 0.73 to 0.47 (br, 6H, (CH$_3$CH$_2$)$_3$Si).

$^{13}$C NMR (CDCl$_3$, 150 MHz) δ 143.3, 137.4, 133.0, 131.4, 129.0, 123.0, 120.0, 91.4, 88.6, 76.1, 54.7, 36.8, 28.3, 7.2, 6.8.

IR (film) 2954, 2874, 1606, 1519, 1457, 1435, 1412, 1384, 1365, 1178, 1143, 1107, 1039, 1016, 835.0, 740.5 cm$^{-1}$.

Example 29

Synthesis of poly-[CH$_2$—CH(C(CH$_3$)$_2$OSi(CH$_2$CH$_3$)$_3$)—CH$_2$-1,4-(phenylene)-(ethynylene)-9,10-(anthranylene)-(ethynylene)-1,4-(phenylene)] (3g) (Pd-catalyst, Sonogashira coupling)

[Chemical Formula 57]

(3g)

A mixed liquid of the triethyl(3-(4-ethynylbenzyl)-4-(4-ethynylphenyl)-2-methylbutan-2-yloxy)silane (4f) (208.3 mg, 0.50 mmol) obtained in the example 21, 9,10-dibromoanthracene (167 mg, 0.50 mmol), tetrakistriphenylphosphine-palladium(0) (57.8 mg, 0.050 mmol), copper iodide (9.5 mg, 0.050 mmol), tetrahydrofuran (5.0 mL) and triethylamine (2.5 mL) in a reaction container was deaerated, and the air inside the reaction container was replaced with argon.

Following stirring of the resulting mixed liquid at 80° C. for 3 days, the temperature was cooled to room temperature, and a saturated aqueous solution of sodium hydrogen carbonate was added to halt the reaction. The mixed liquid was extracted using chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into methanol, the polymer compound precipitated as a solid. This solid was collected by filtration, washed with hexane, and then dried under reduced pressure, yielding the title polymer compound (3g) (148 mg, 0.25 mmol) as a red-brown solid in a yield of 50%.

The results of NMR and the like are shown below.

GPC (solvent: THF, standard: poly-styrene: $M_n$=5.20×10$^3$, $M_w$=8.27×10$^3$, $M_w/M_n$=1.59.

$^1$H NMR (CDCl$_3$, 600 MHz) δ 8.84 to 8.30 (br m, 4H, Ar), 7.67 to 7.25 (br m, overlap with CHCl$_3$ peak, 8H, Ar), 7.25 to 6.75 (br m, 4H, Ar), 3.26 to 2.82 (br, 2H, CH$_2$Ar), 2.60 to 2.29 (br, 2H, CH$_2$Ar), 2.29 to 2.00 (br, 1H, CHCH$_2$Ar), 1.36 to 1.10 (br, 6H, (CH$_3$)$_2$C), 1.10 to 0.75 (br, 9H, (CH$_3$CH$_2$)$_3$Si), 0.75 to 0.30 (br, 6H, (CH$_3$CH$_2$)$_3$Si).

$^{13}$C NMR (CDCl$_3$, 150 MHz) δ 134.0, 132.7, 132.2, 131.8, 131.7, 131.5, 131.4, 131.3, 129.2, 127.9, 127.1, 126.4, 120.6, 120.3, 118.3, 102.6, 86.2, 76.1, 54.9, 37.0, 28.3, 7.3, 7.2, 6.9.

IR (film) 2954, 2873, 1606, 1509, 1462, 1455, 1434, 1414, 1384, 1365, 1016, 762.7 cm$^{-1}$.

Example 30

Synthesis of poly-[CH$_2$—CH(C(CH$_3$)$_2$OSi(CH$_2$CH$_3$)$_3$)—CH$_2$-1,4-(2,5-bis(dodecyloxy)phenylene)-(ethynylene)-1,4-(phenylene)-(ethynylene)-1,4-(phenylene)] (3h) (Pd-catalyst, Sonogashira coupling)

[Chemical Formula 58]

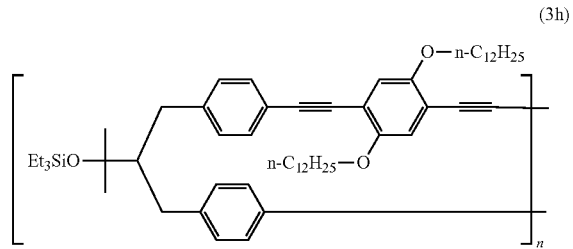

(3h)

A mixed liquid of the triethyl(3-(4-ethynylbenzyl)-4-(4-ethynylphenyl)-2-methylbutan-2-yloxy)silane (4f) (208.3 mg, 0.50 mmol) obtained in the example 21, 1,4-bis(dodecyloxy)-2,5-diodobenzene (349.1 mg, 0.50 mmol), tetrakistriphenylphosphinepalladium(0) (57.8 mg, 0.050 mmol), copper iodide (9.5 mg, 0.050 mmol), tetrahydrofuran (5.0 mL) and triethylamine (2.5 mL) in a reaction container was deaerated, and the air inside the reaction container was replaced with argon.

Following stirring of the resulting mixed liquid at 80° C. for 3 days, the temperature was cooled to room temperature, and a saturated aqueous solution of sodium hydrogen carbonate was added to halt the reaction. The mixed liquid was extracted using chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into methanol, the polymer compound precipitated as a solid. This solid was collected by filtration and dried under reduced pressure, yielding the title polymer compound (3h) (413 mg, 0.48 mmol) as a red viscous solid in a yield of 95%.

The results of NMR and the like are shown below.

GPC (solvent: THF, standard: poly-styrene: $M_n$=4.24×10$^3$, $M_w$=7.35×10$^3$, $M_w/M_n$=1.73.

$^1$H NMR (CDCl$_3$, 600 MHz) δ 7.41 to 7.22 (br m, overlap with CHCl$_3$ peak, 6H, Ar), δ 7.05 to 6.91 (br m, 4H, Ar), 4.02 to 3.91 (br, 4H, OCH$_2$), 2.99 to 2.88 (br, 2H, CH$_2$Ar), 2.48 to 2.36 (br, 2H, CH$_2$Ar), 2.12 to 2.06 (br, 1H, CHCH$_2$Ar), 1.85 to 1.76 (br, 4H, OCH$_2$CH$_2$), 1.58 to 1.10 (br, 42H, (CH$_3$)$_2$C and (CH$_2$)$_9$CH$_3$), 1.03 to 0.92 (br, 9H, (CH$_3$CH$_2$)$_3$Si), 0.92 to 0.83 (br, 6H, CH$_2$CH$_3$), 0.65 to 0.56 (br, 6H, (CH$_3$CH$_2$)$_3$Si).

$^{13}$C NMR (CDCl$_3$, 150 MHz) δ 153.6, 151.8, 143.2, 134.9, 131.4, 129.8, 129.0, 127.5, 120.6, 118.9, 116.9, 114.0, 95.0, 85.5, 76.2, 70.1, 70.0, 69.6, 54.7, 36.8, 36.7, 31.9, 29.7, 29.6, 29.4, 28.4, 26.1, 26.0, 22.7, 14.1, 7.2, 6.9.

IR (film) 2924, 2853, 1516, 1489, 1464, 1415, 1384, 1215, 1016, 742.5, 721.3 cm$^{-1}$.

Example 31

Synthesis of poly-[CH$_2$—CH(C(CH$_3$)$_2$OSi(CH$_2$CH$_3$)$_3$)—CH$_2$-1,4-(phenylene)-(ethynylene)-2,5-(thiophenylene)-2,5-(thiophenylene)-(ethynylene)-1,4-(phenylene)] (3i) (Pd-catalyst, Sonogashira coupling)

[Chemical Formula 59]

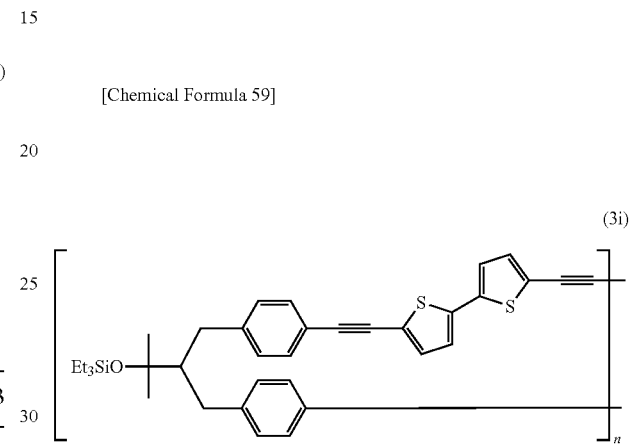

(3i)

A mixed liquid of the triethyl(3-(4-ethynylbenzyl)-4-(4-ethynylphenyl)-2-methylbutan-2-yloxy)silane (40 (208.3 mg, 0.50 mmol) obtained in the example 21, 5,5'-dibromo-2,2'-bithiophene (161 mg, 0.50 mmol), tetrakistriphenylphosphinepalladium(0) (57.8 mg, 0.050 mmol), copper iodide (9.5 mg, 0.050 mmol), tetrahydrofuran (5.0 mL) and triethylamine (2.5 mL) in a reaction container was deaerated, and the air inside the reaction container was replaced with argon.

Following stirring of the resulting mixed liquid at 80° C. for 3 days, the temperature was cooled to room temperature, and a saturated aqueous solution of sodium hydrogen carbonate was added to halt the reaction. The mixed liquid was extracted using chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into methanol, the polymer compound precipitated as a solid. This solid was collected by filtration, washed with hexane, and then dried under reduced pressure, yielding the title polymer compound (3i) (260 mg, 0.45 mmol) as a red-brown solid in a yield of 90%.

The results of NMR and the like are shown below.

GPC (solvent: THF, standard: poly-styrene: $M_n$=6.32×10$^3$, $M_w$=1.18×10$^4$, $M_w/M_n$=1.87.

$^1$H NMR (CDCl$_3$, 600 MHz) δ 7.49 to 6.81 (br m, overlap with CHCl$_3$ peak, 12H, Ar), 3.07 to 2.86 (br, 2H, CH$_2$Ar), 2.49 to 2.27 (br, 2H, CH$_2$Ar), 2.15 to 2.01 (br, 1H, CHCH$_2$Ar), 1.41 to 1.10 (br, 6H, (CH$_3$)$_2$C), 1.06 to 0.84 (br, 9H, (CH$_3$CH$_2$)$_3$Si), 0.72 to 0.49 (br, 6H, (CH$_3$CH$_2$)$_3$Si).

$^{13}$C NMR (CDCl$_3$, 150 MHz) δ 143.4, 137.9, 132.5, 131.2, 129.1, 127.9, 123.9, 119.7, 94.8, 82.0, 76.1, 54.8, 54.7, 36.9, 28.3, 7.2, 6.9.

IR (film) 2954, 2873, 1731, 1519, 1455, 1384, 1366, 1251, 1186, 1015, 794.5, 741.5 cm$^{-1}$.

Example 32

Synthesis of poly-[$CH_2$—CH(C($CH_3$)$_2$OSi ($CH_2CH_3$)$_3$)—$CH_2$-1,4-(phenylene)-(E)-1,2-(ethenylene)-1,4-(phenylene)] (3j) (McMurry coupling)

[Chemical Formula 60]

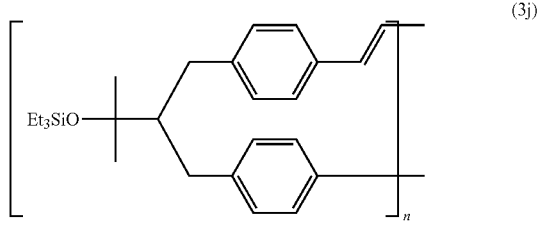

(3j)

A mixed liquid of the 4,4'-(2-(2-(triethylsilyloxy)propan-2-yl)propan-1,3-diyl)dibenzaldehyde (4e) (212.3 mg, 0.50 mmol) obtain in the example 20, magnesium powder (24.3 mg, 2.0 mmol) and tetrahydrofuran (2.5 mL) in a reaction container was deaerated, and the air inside the reaction container was replaced with argon. To this mixed liquid were added triethylamine (0.36 mL, 2.6 mmol), triisopropyl orthotitanate(IV) (0.38 mL, 1.3 mmol) and trimethylsilyl chloride (0.16 mL, 1.3 mmol).

Following stirring of the resulting mixed liquid at 50° C. for 2 days, the temperature was cooled to room temperature, and a saturated aqueous solution of sodium hydrogen carbonate was added to halt the reaction. The mixed liquid was extracted using chloroform, and the thus obtained organic layer was washed with water, dried using anhydrous sodium sulfate, and filtered. The filtrate was concentrated under reduced pressure, and the residue was purified by silica gel column chromatography (ethyl acetate), yielding the title polymer compound (3j) (68.6 mg, 0.18 mmol) as a light yellow viscous liquid in a yield of 35%.

The results of NMR and the like are shown below.

GPC (solvent: THF, standard: poly-styrene: $M_n$=1.15×10$^3$, $M_w$=2.14×10$^3$, $M_w/M_n$=1.86.

$^1$H NMR (CDCl$_3$, 600 MHz) δ 7.31 to 6.86 (br m, overlap with CHCl$_3$ peak, 10H, Ar and CH=CH), 2.98 to 2.72 (br, 2H, CH$_2$Ar), 2.48 to 2.33 (br, 2H, CH$_2$Ar), 2.12 to 2.01 (br, 1H, CHCH$_2$Ar), 1.27 to 0.86 (br m, 15H, (CH$_3$)$_2$C and (CH$_3$CH$_2$)$_3$Si), 0.67 to 0.54 (br m, 6H, (CH$_3$CH$_2$)$_3$Si).

Confirmation of Stacked Structures

Example 33

The ratio of stacked structures within each of the compounds (1a-1) and (1b) to (1 h) obtained in the examples 1-1 and examples 2 to 8 respectively, and within toluene as a comparative example, was calculated from MM2 (Molecular Mechanics Program 2) calculations and the respective emission spectrum.

In the examples, the absorption spectra were measured using a spectrophotometer (Shimadzu UV-2450, manufactured by Shimadzu Corporation). The excitation and emission spectra were measured using a spectrofluorophotometer (Shimadzu RF-5300PC, manufactured by Shimadzu Corporation).

The emission ratio is calculated by preparing a 10$^{-4}$ M dichloromethane solution of each of the compounds, exciting the compound with light having a wavelength of 259 to 263 nm, and then calculating the ratio between the emission at 289 nm attributable to the benzene rings, and the emission at 333 nm attributable to the benzene ring excimer.

As illustrated in Table 1, the compounds (1a-1) and (1b) to (1h) obtained in the examples 1-1 and 2 to 8 each formed a stacked structure of the benzene rings, and an excimer emission was obtained. Particularly in the case of the compounds (1b) to (1h) obtained in the examples 2 to 8, where one of R1 and R2 was a hydrogen atom, the stacked structure of the benzene rings was formed preferentially, and the excimer emission was predominantly obtained.

As shown in Table 1, the compounds of the present invention formed a stacked structure of the benzene rings, and in a $^1$H-NMR analysis conducted in a deutertaed chloroform solution at room temperature, the chemical shift of the ortho-position proton of the benzene rings exhibited a high magnetic field shift compared with the reference toluene compound (7.18 ppm).

In the table, for the ratio "O:H—O:C" which is used as the standard for determining the stacked structure ratio, the "O" state, the "H—O" state and the "C" state refer to the structural states shown below.

[Chemical Formula 61]

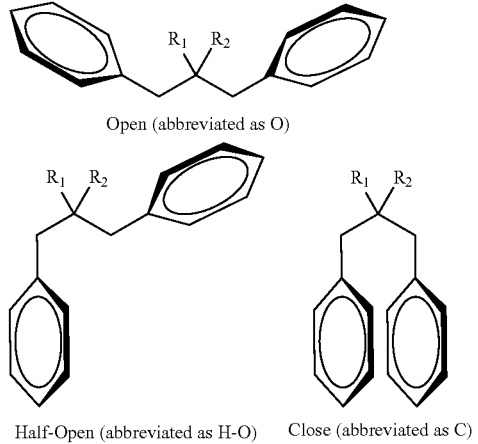

Open (abbreviated as O)

Half-Open (abbreviated as H-O)   Close (abbreviated as C)

TABLE 1

| | R1 | R2 | O:H-O:C ratio | Emission ratio between benzene rings and benzene ring excimer | $^1$H-NMR chemical shift of ortho-position proton in benzene ring (ppm) |
|---|---|---|---|---|---|
| Example 1-1 (1a-1) | COOEt | COOEt | 48:51:1 | 72:28 | 7.17 |
| Example 2 (1b) | H | CMe$_2$(OH) | 2:16:82 | 13:87 | 7.05 |

TABLE 1-continued

| | R1 | R2 | O:H-O:C ratio | Emission ratio between benzene rings and benzene ring excimer | $^1$H-NMR chemical shift of ortho-position proton in benzene ring (ppm) |
|---|---|---|---|---|---|
| Example 3 (1c) | H | CMe$_2$(OMe) | 1:8:91 | 11:89 | 7.00 |
| Example 4 (1d) | H | CMe$_2$(TESO) | 1:9:90 | 7:93 | 6.98 |
| Example 5 (1e) | H | CEt$_2$(OH) | 1:17:82 | 14:86 | 7.02 |
| Example 6 (1f) | H | CEt$_2$(OMe) | 0:1:99 | 14:86 | 6.95 |
| Example 7 (1g) | H | CHMe(OMe) | 6:30:64 | 35:65 | 7.12 |
| Example 8 (1h) | H | CH$_2$(OMe) | 30:19:51 | 48:52 | 7.16 |
| Toluene | — | — | — | No excimer emission | 7.18 |

Confirmation of Absorption Spectra and Emission Spectra

Example 34

The absorption and emission spectra were compared for the poly-[CH$_2$—CH(C(CH$_3$)$_2$OSi(CH$_2$CH$_3$)$_3$)—CH$_2$-1,4-(phenylene)-2,5-(thiophenylene)-2,5-(thiophenylene)-1,4-(phenylene)] (3a) synthesized in the example 23, the poly-[CH$_2$—CH(C(CH$_3$)$_2$OSi(CH$_2$CH$_3$)$_3$)—CH$_2$-1,4-(phenylene)-(E)-1,2-(ethenylene)-1,4-(phenylene)-(E)-1,2-(ethenylene)-1,4-(phenylene)] (3b) synthesized in the example 24, and diMe-P2T and BStB, which lack a trimethylene region having a substituent at position-2. The structures of the compounds are shown below.

[Chemical Formula 62]

3a

3b diMe-P2T

-continued

BStB

FIG. 1 illustrates the UV absorption spectra and the emission spectra for the polymer 3a, the oligomer (pentamer or hexamer) 3a', and the polymer 3b. As is evident from the absorption spectra and the emission spectra shown in FIG. 1, when a derivative having a substituent at position-2 of a trimethylene group is used as a linking portion, an absorption blue shift and an emission red shift are observed compared with diMe-P2T and BStB, indicating that the compound is preferentially adopting a stacked structure in which the π-conjugated groups are stacked upon each other.

In FIG. 1, (a) is a diagram illustrating absorption spectra. The concentration of diMe-P2T was 10$^{-6}$ M (CH$_2$Cl$_2$ solution), and the concentration of 3a was 10$^{-5}$ M (CH$_2$Cl$_2$ solution).

(b) is a diagram illustrating fluorescence spectra. The fluorescence spectra were obtained by exciting the diMe-P2T (within CH$_2$Cl$_2$) at 375 nm, 3a (within CH$_2$Cl$_2$) at 367 nm, 3a (within CH$_3$CN) at 336 nm, and a 3a film at 344 nm.

(c) is a diagram illustrating excitation spectra and fluorescence spectra. The fluorescence spectra were obtained by performing excitation within CH$_3$CN at 10$^{-6}$M, at 374 nm for diMe-P2T, at 336 nm for 3a, and at 364 nm for 3a'.

(d) is a diagram illustrating excitation spectra and fluorescence spectra. The concentration of BStB was 10$^{-7}$ M (CH$_2$Cl$_2$ solution). The fluorescence spectra were obtained by exciting the BStB at 364 nm and 3b' at 326 nm.

The oligomer of 3a' is a pentamer and/or hexamer obtained by performing the polymerization reaction of the example 23 without the addition of the tri-n-octylmethylammonium chloride. The 3a film was prepared from a 10$^{-3}$ M CH$_2$Cl$_2$ solution of 3a using a spin coating method.

AFM (Atomic Force Microscope) and XRD (X-ray Diffraction) Analyses

Example 35

The poly-[CH$_2$—CH(C(CH$_3$)$_2$OSi(CH$_2$CH$_3$)$_3$)—CH$_2$-1,4-(phenylene)-2,5-(thiophenylene)-2,5-(thiophenylene)-1,4-(phenylene)] (3a) synthesized in the example 23 was dissolved in CH$_2$Cl$_2$ to form a 0.1 mass % solution, and a thin film was prepared by dripping and spin coating the solution onto a silicon substrate. This thin film was heated at 210° C.

for one minute, heated at 160° C. for a further 2 minutes, and then cooled to room temperature to obtain a film of the polymer compound 3a.

The thus obtained film of the polymer compound 3a was observed using an AFM (Digital Instruments Nanoscope V) in tapping mode. Further, following annealing on the silicon substrate, the film was removed from the substrate and the remaining powder was subjected to XRD analysis (Rigaku RINT-Ultima III diffractometer).

[Chemical Formula 63]

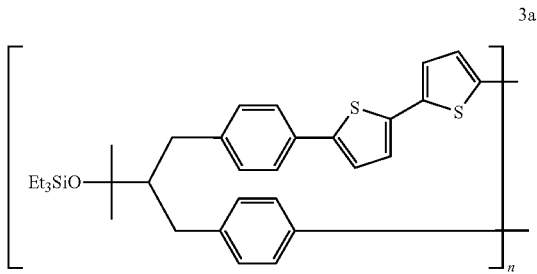

(3a)

Figure 2:
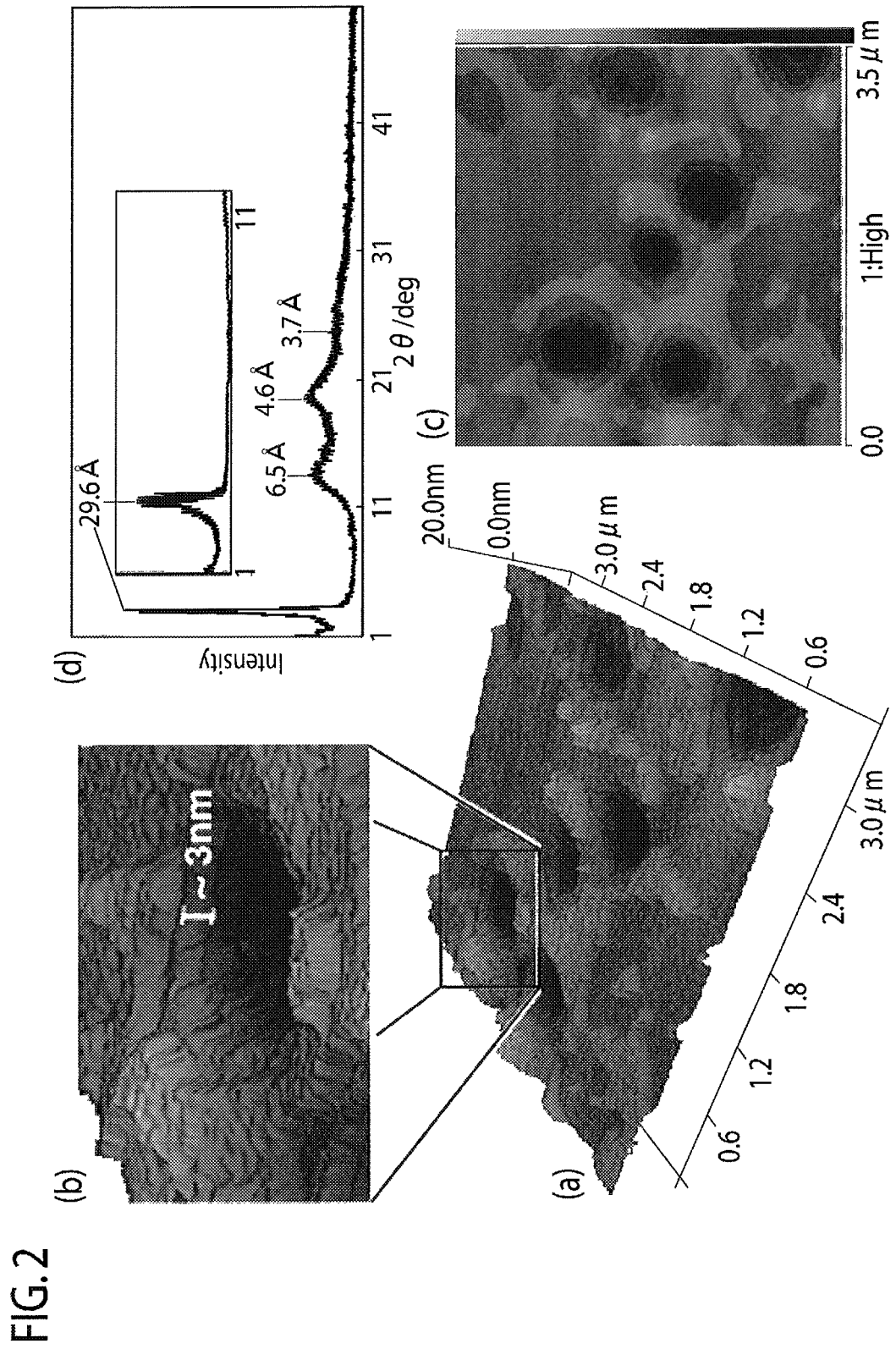
FIG. 2 illustrates AFM (atomic force microscope) images (a), (b) and (c), and an XRD (X-ray diffraction) spectrum (d) of a heat-treated polymer compound obtained in an example 35.

FIG. 2 illustrates the obtained AFM images (a), (b) and (c) and the XRD spectrum (d) of the 3a film. As is evident from FIG. 2(b), by heat-treating the film of the polymer compound, a layered structure was formed. In the AFM images, it is thought that those portions shown as dark colors are depressions formed as a result of aggregation of the polymer compound 3a.

Synthesis of Reactive Compounds and Polymer Compounds

Example 36

Synthesis of ethyl 2-(4-bromobenzyl)-3-(4-iodophenyl)propanoate (4h)

[Chemical Formula 64]

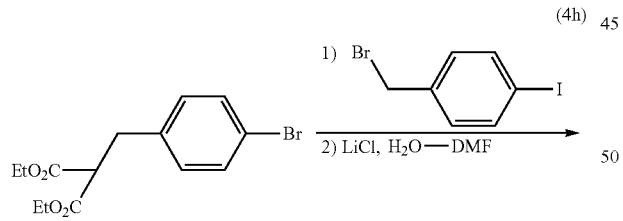

(4h)

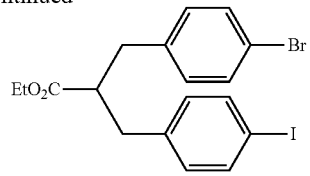

A mixed liquid containing diethyl 4-bromobenzylmalonate (9.88 g, 30.0 mmol) and anhydrous N,N-dimethylformamide (12.0 mL) was added gradually at 0° C. to a mixed liquid containing sodium hydride (62 wt % in oil, 1.74 g, 45 mmol) and anhydrous N,N-dimethylformamide (18.0 mL). Following stirring of the resulting mixed liquid at this temperature for 30 minutes, a mixed liquid containing 4-iodobenzyl bromide (11.6 g, 39.0 mmol) and anhydrous N,N-dimethylformamide (30 mL) was added. The resulting mixed liquid was stirred at room temperature for 3 hours, and a saturated aqueous solution of ammonium chloride was then added to halt the reaction. The organic layer was separated from the mixed liquid, and the water layer was extracted with ethyl acetate. The thus obtained organic layer was washed with a saturated saline solution and then dried using anhydrous magnesium sulfate. The organic layer was filtered, the filtrate was concentrated under reduced pressure, to the thus obtained residue were added lithium chloride (5.09 g, 120 mmol), water (1.08 mL) and N,N-dimethylformamide (100 mL), and the resulting mixture was heated for 12 hours at 160° C. The thus obtained mixed liquid was cooled to room temperature, water (100 mL) was added, and the mixture was extracted with ethyl acetate. The thus obtained organic layer was dried using anhydrous magnesium sulfate and filtered. The filtrate was concentrated under reduced pressure, and the resulting residue was purified by silica gel column chromatography (hexane:ethyl acetate=70:1), yielding the title compound (4h) (11.9 g, 25.2 mmol) as a yellow liquid in a yield of 84%.

$^1$H NMR (500 MHz, CDCl$_3$) δ 7.59 (d, 2H, J=8.5 Hz, Ar), 7.39 (d, 2H, J=8.5 Hz, Ar), 7.02 (d, 2H, J=8.5 Hz, Ar), 6.90 (d, 2H, J=9.0 Hz, Ar), 3.96 (q, 2H, J=7.2 Hz, CO$_2$CH$_2$CH$_3$), 2.93 to 2.83 (m, 3H, CH$_2$Ar and CHCH$_2$Ar), 2.76 to 2.68 (m, 2H, CH$_2$Ar), 1.03 (t, 3H, J=7.3 Hz, CO$_2$CH$_2$CH$_3$).

$^{13}$C NMR (CDCl$_3$, 125 MHz) δ 174.2, 138.4, 137.8, 137.4, 131.4, 130.9, 130.6, 120.3, 91.7, 60.4, 49.1, 37.6, 37.5, 14.0.

IR (neat) 2977, 2949, 2929, 1731, 1715, 1488, 1374, 1212, 1009, 805.1, 754.0, 648.0 cm$^{-1}$.

Example 37

Synthesis of 4,4'-((1E,1'E)-1,4-phenylenebis(ethen-2,1-diyl)bis(4,1-phenylene))bis(3-(4-bromobenzyl)-2-methylbutan-2-ol) (10a)

[Chemical Formula 65]

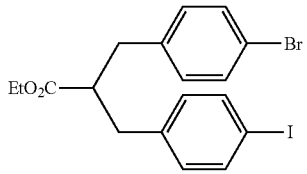

(10a)

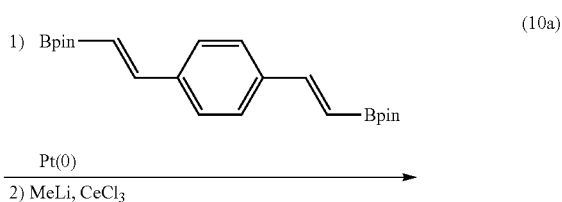

-continued

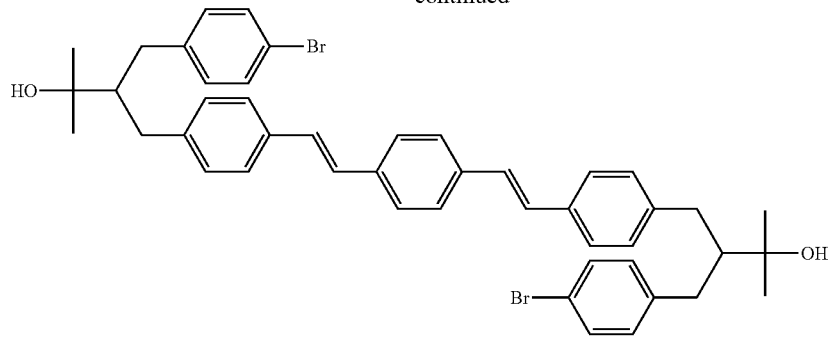

A mixed liquid of 1,4-bis((E)-2-(4,4,5,5-tetramethyl-1,3,2-dioxaborolan-2-yl)vinyl)benzene (764 mg, 2.00 mmol), ethyl 2-(4-bromobenzyl)-3-(4-iodophenyl)propanoate (1.09 g, 2.30 mmol), cesium carbonate (1.30 g, 4.00 mmol) and N,N-dimethylformamide (10.0 mL) in a reaction container was deaerated, and the air inside the reaction container was replaced with argon. A solution of tetrakistriphenylphosphineplatinum(0) (62.2 mg, 0.050 mmol) in N,N-dimethylformamide (3.30 mL) was then added to the mixed liquid. The thus obtained mixed liquid was stirred at 120° C. for 12 hours, and following cooling to room temperature, a saturated aqueous solution of ammonium chloride was added to halt the reaction. The mixed liquid was then extracted with ethyl acetate. The thus obtained organic layer was dried using anhydrous magnesium sulfate, and filtered. The filtrate was concentrated under reduced pressure, and the resulting residue was purified by silica gel column chromatography (hexane:ethyl acetate=8:1), yielding a yellow solid. Meanwhile, a mixed liquid of anhydrous cerium(III) chloride (2.958 g, 12.0 mmol) and tetrahydrofuran (32.0 mL) was stirred at room temperature for 12 hours, and following subsequent cooling to −78° C., an ether solution of methyllithium (7.5 mL, 1.6 M, 12.0 mmol) was added, and the mixture was stirred for 5 hours. To the resulting mixed liquid at −78° C. was added a solution of the above-prepared yellow solid in tetrahydrofuran (6.0 mL), and the resulting mixture was stirred for 2 hours. Following addition of a 0.1 M aqueous solution of acetic acid to the mixed liquid to halt the reaction, the mixture was extracted with ethyl acetate. The thus obtained organic layer was washed with water, dried using anhydrous sodium sulfate, and then filtered. The filtrate was concentrated under reduced pressure, and the residue was purified by silica gel column chromatography (hexane:ethyl acetate=3:1), yielding the title compound (10a) (428 mg, 0.54 mmol) as a colorless liquid in a yield of 27%.

$^1$H NMR (500 MHz, CDCl$_3$) δ 7.49 (s, 4H, Ar), 7.36 (d, 4H, J=8.5 Hz, Ar), 7.29 (d, 4H, J=8.5 Hz, Ar), 7.06 (d, 4H, J=4.0 Hz, CH=CH), 7.02 (d, 4H, J=8.0 Hz, Ar), 6.89 (d, 4H, J=8.0 Hz, Ar), 2.94 to 2.84 (m, 4H, CH$_2$Ar), 2.48 to 2.40 (m, 4H, CH$_2$Ar), 2.16 to 2.09 (m, 2H, CHCH$_2$Ar), 1.26 and 1.27 (2s, 12H, (CH$_3$)$_2$C).

$^{13}$C NMR (CDCl$_3$, 150 MHz) δ 141.1, 136.7, 135.1, 131.2, 130.7, 129.3, 128.2, 127.6, 126.7, 126.5, 74.0, 53.9, 36.7, 36.2, 27.8, 27.5.

IR (film) 3580, 3433, 2965, 2925, 1514, 1487, 1369, 1107, 1011, 963.3, 824.4, 791.6, 553.5 cm$^{-1}$.

Example 38

Synthesis of 1,4-bis((E)-4-(2-(4-bromobenzyl)-3-methyl-3-((triethylsilyl)oxy)butyl)styryl)benzene (10b)

[Chemical Formula 66]

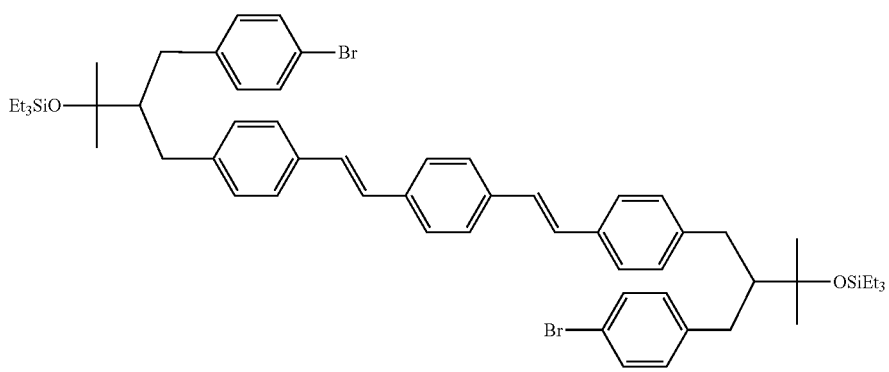

(10b)

Imidazole (136 mg, 2.0 mmol), triethylsilyl chloride (0.25 mL, 3.0 mmol) and N,N-dimethylformamide (2.50 mL) were added at 0° C. to 4,4'-((1E,1'E)-1,4-phenylenebis(ethen-2,1-diyl)bis(4,1-phenylene))bis(3-(4-bromobenzyl)-2-methylbutan-2-ol) (396 mg, 0.50 mmol). Following stirring of the resulting mixed liquid at room temperature for 12 hours, a saturated aqueous solution of ammonium chloride was added to halt the reaction. The organic layer was separated from the mixed liquid, and the water layer was extracted with ether. The resulting organic layer was washed with water, dried using anhydrous magnesium sulfate, and filtered. The filtrate was concentrated under reduced pressure, and the resulting residue was purified by silica gel column chromatography (hexane), yielding the title compound (10b) (444 mg, 0.43 mmol) as a yellow viscous solid in a yield of 87%.

$^1$H NMR (500 MHz, CDCl$_3$) δ 7.48 (s, 4H, Ar), 7.31 (d, 4H, J=8.0 Hz, Ar), 7.24 (d, 4H, J=8.0 Hz, Ar), 7.07 (d, 2H, J=16.5 Hz, CH=CH) 7.02 (d, 2H, J=16.5 Hz, CH=CH), 6.96 (d, 4H, J=8.0 Hz, Ar), 6.83 (d, 4H, J=8.0 Hz, Ar), 2.87 to 3.00 (m, 4H, CH$_2$Ar), 2.41 to 2.33 (m, 4H, CH$_2$Ar), 2.10 to 2.02 (m, 1H, CHCH$_2$Ar), 1.22 (s, 12H, (CH$_3$)$_2$C) 0.98 (t, J=7.8 Hz, 18H, (CH$_3$CH$_2$)$_3$Si), 0.62 (q, 12H, J=7.8 Hz, (CH$_3$CH$_2$)$_3$Si).

$^1$H NMR (CDCl$_3$, 150 MHz) δ 142.0, 141.8, 134.7, 131.0, 130.7, 129.3, 128.3, 127.4, 126.7, 126.2, 124.3, 119.0, 76.2, 54.9, 36.6, 36.1, 28.3, 28.1, 7.2, 6.8.

IR (neat) 2962, 2873, 1602, 2457, 1384, 1261, 1039, 797.4, 703.9 cm$^{-1}$.

Example 39

Synthesis of Polymer Compound (5a)

[Chemical Formula 67]

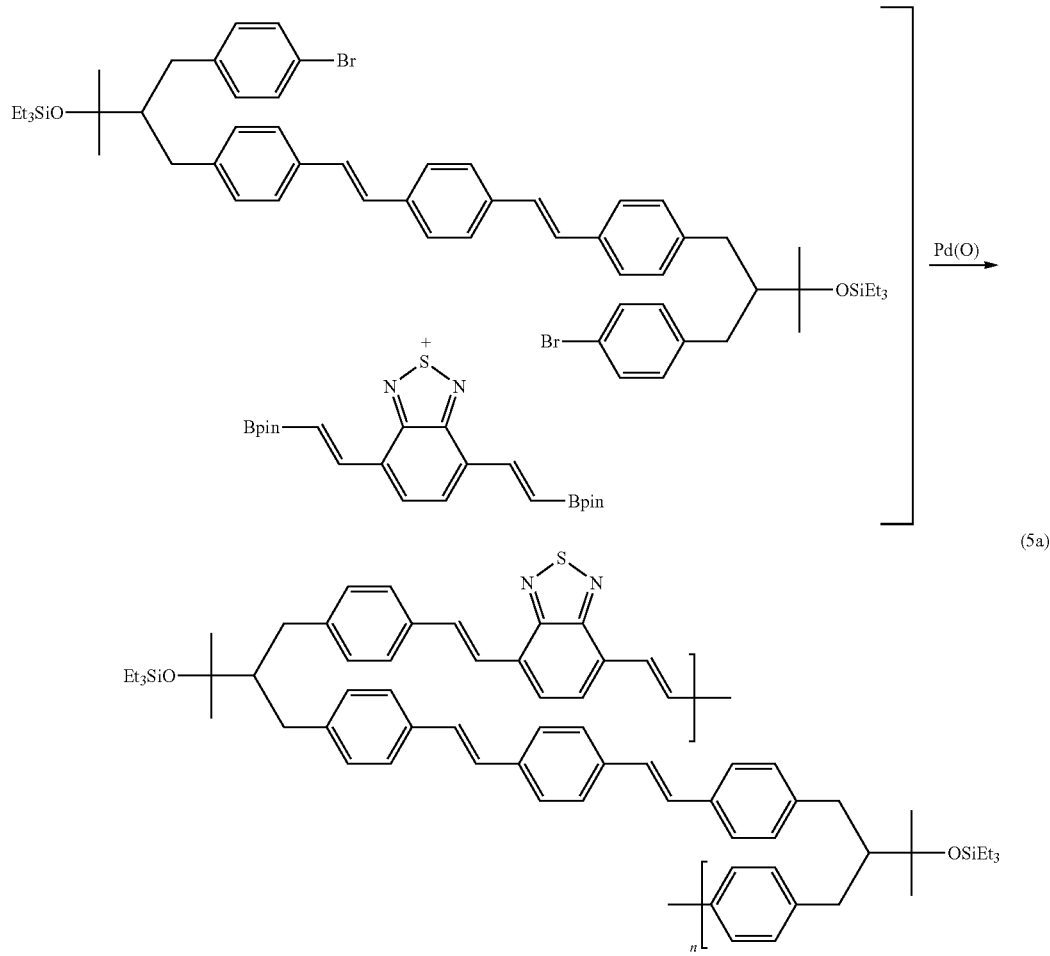

A mixed liquid of 1,4-bis((E)-4-(2-(4-bromobenzyl)-3-methyl-3-((triethylsilyl)oxy)butyl)styryl)benzene (510 mg, 0.50 mmol), 4,7-bis((E)-2-(4,4,5,5-tetramethyl-1,3,2-dioxaborolan-2-yl)vinyl)benzo[c][1,2,5]thiadiazole (220 mg, 0.5 mmol), tetra-n-butylammonium bromide (166 mg, 0.50 mmol), a 2 M aqueous solution of potassium carbonate (1.0 mL) and tetrahydrofuran (2.3 mL) in a reaction container was deaerated, and the air inside the reaction container was replaced with argon. A solution containing tetrakistriphenylphosphinepalladium(0) (23 mg, 0.020 mmol) in tetrahydrofuran (1.0 mL) was added to the mixed liquid. Following stirring of the resulting mixed liquid at 80° C. for 3 days, the temperature was cooled to room temperature, and a saturated aqueous solution of sodium hydrogen carbonate was added to halt the reaction. The mixed liquid was extracted using chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into hexane, the polymer compound precipitated as a solid. This solid was collected by filtration, washed with diethyl ether, and then dried under reduced pressure, yielding the polymer compound (5a) (173 mg, 0.165 mmol) as a brown solid in a yield of 33%.

GPC (solvent: THF, standard: poly-styrene: M$_n$=5.15×10$^3$, M$_w$=8.94×10$^3$, M$_w$/M$_n$=1.74.

UV absorption spectra: λ$_{abs\ max}$ 360 nm (in CH$_2$Cl$_2$), 355 nm (film).

Emission spectra: λ$_{em\ max}$ 559 nm (in CH$_2$Cl$_2$), 556 nm (film).

$^1$H NMR (500 MHz, CDCl$_3$) δ 7.52 to 6.68 (br m, 30H per a repeated unit, Ar), 3.06 to 2.84 (br, 4H per a repeated unit, CH$_2$Ar), 2.49 to 2.25 (br, 4H per a repeated unit, CH$_2$Ar), 2.20 to 1.98 (br, 2H per a repeated unit, CHCH$_2$Ar), 1.30 to 1.09 (br, 6H per a repeated unit, (CH$_3$)$_2$C), 1.04 to 0.79 (br, 9H per a repeated unit, (CH$_3$CH$_2$)$_3$Si), 0.68 to 0.44 (br, 6H per a repeated unit, (CH$_3$CH$_2$)$_3$Si).

IR (film) 2949, 2872, 1598, 1513, 1456, 1382, 1364, 1177, 1141, 1011, 959.4, 821.5, 721.2, 545.8 cm$^{-1}$.

Example 40

Synthesis of Polymer Compound (3k)

[Chemical Formula 68]

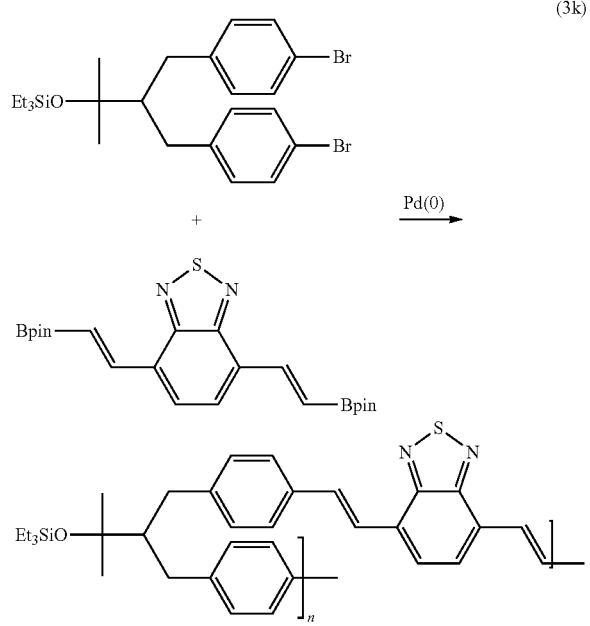

A mixed liquid of (3-(4-bromobenzyl)-4-(4-bromophenyl)-2-methylbutan-2-yloxy)triethylsilane (263 mg, 0.50 mmol), 4,7-bis((E)-2-(4,4,5,5-tetramethyl-1,3,2-dioxaborolan-2-yl)vinyl)benzo[c][1,2,5]thiadiazole (220 mg, 0.5 mmol), tetra-n-butylammonium bromide (161 mg, 0.50 mmol), a 2 M aqueous solution of potassium carbonate (1.0 mL) and tetrahydrofuran (2.3 mL) in a reaction container was deaerated, and the air inside the reaction container was replaced with argon. A solution containing tetrakistriphenylphosphinepalladium(0) (23 mg, 0.020 mmol) in tetrahydrofuran (1.0 mL) was added to the mixed liquid. Following stirring of the resulting mixed liquid at 80° C. for 3 days, the temperature was cooled to room temperature, and a saturated aqueous solution of sodium hydrogen carbonate was added to halt the reaction. The mixed liquid was extracted using chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into hexane, the polymer compound precipitated as a solid. This solid was collected by filtration, washed with diethyl ether, and then dried under reduced pressure, yielding the polymer compound (3k) (58.0 mg, 0.105 mmol) as a brown solid in a yield of 21%.

GPC (solvent: THF, standard: poly-styrene: M$_n$=3.60×10$^3$, M$_w$=7.64×10$^3$, M$_w$/M$_n$=2.12

UV absorption spectra: λ$_{abs\ max}$ 316 nm (in CH$_2$CH$_2$).
Emission spectra: λ$_{em\ max}$ 556 nm (in CH$_2$Cl$_2$).

$^1$H NMR (500 MHz, CDCl$_3$) δ 6.60 to 7.90 (m, 14H per a repeated unit, Ar and olefin), 2.70 to 3.10 (m, 2H per a repeated unit, CH$_2$), 2.30 to 2.50 (m, 2H per a repeated unit, CH$_2$), 0.40 to 1.90 (m, 22H per a repeated unit).

IR (film) 3059, 2970, 2932, 1593, 1567, 1473, 1424, 1384, 1070, 996.1, 776.2, 691.4 cm$^{-1}$.

Example 41

Synthesis of 2-methyl-3-(4-(thiophen-2-yl)benzyl)-4-(4-thiophen-4-yl)phenyl)butan-2-ol (2g)

[Chemical Formula 69]

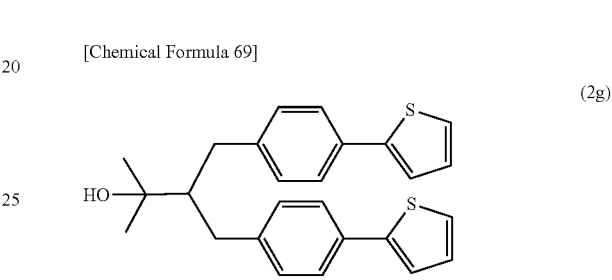

A mixed liquid of ethyl 2-(4-bromobenzyl)-3-(4-bromophenyl)propanoate (2.13 g, 5.0 mmol), 5,5-dimethyl-2-(thiophen-2-yl)-1,4,2-dioxaborinane (2.52 g, 12.0 mmol), tetrahydrofuran (23.3 mL) and a 2 M aqueous solution of sodium carbonate (10.0 mL) in a reaction container was deaerated, and the air inside the reaction container was replaced with argon. A solution containing tetrakistriphenylphosphinepalladium(0) (346 mg, 0.30 mmol) in tetrahydrofuran (10 mL) was added to the mixed liquid. Following stirring of the resulting mixed liquid at 80° C. for 20 hours, the temperature was cooled to room temperature, and a saturated aqueous solution of ammonium chloride was added to halt the reaction. The organic layer was separated from the mixed liquid, and the water layer was extracted with ethyl acetate. The thus obtained organic layer was washed with a saturated aqueous solution of sodium chloride, dried using anhydrous magnesium sulfate, and filtered. The filtrate was concentrated under reduced pressure, and the resulting residue was purified by flash silica gel column chromatography (hexane:ethyl acetate=10:1). Tetrahydrofuran (10 mL) was added to the resulting liquid, the solution was cooled to 0° C., an ether solution of methylmagnesium iodide (8.8 mL, 1.41 M, 12.5 mmol) was added, and the resulting mixed liquid was stirred for 5 hours. Subsequently, a saturated aqueous solution of ammonium chloride was added to the mixed liquid to halt the reaction, and the mixed liquid was then extracted with ethyl acetate. The thus obtained organic layer was washed with a saturated aqueous solution of sodium chloride, dried using anhydrous magnesium sulfate, and filtered. The filtrate was concentrated under reduced pressure, and the resulting residue was purified by silica gel column chromatography (hexane:ethyl acetate=5:1), yielding the title compound (2g) as a colorless solid in a yield of 65%.

$^1$H NMR (600 MHz, CDCl$_3$) δ 7.44 (d, 4H, J=8.0 Hz, Ar), 7.24 to 7.22 (m, 4H, Ar), 7.07 to 7.03 (m, 6H, Ar), 2.92 (dd, 2H, J=4.3, 14.0 Hz, CH$_2$Ar), 2.50 (dd, 2H, J=7.5, 14.5 Hz, CH$_2$Ar), 2.21 to 2.17 (m, 1H, CHCH$_2$Ar), 1.29 (s, 6H, (CH$_3$)$_2$C).

$^{13}$C NMR (CDCl$_3$, 150 MHz) δ 144.4, 141.4, 132.0, 129.5, 127.9, 125.9, 124.3, 122.7, 74.2, 53.9, 36.5, 27.7.

IR (film) 3466, 2976, 2933, 1500, 1432, 1258, 1211, 1236, 1026, 804.2, 693.3 cm$^{-1}$.

Example 42

Synthesis of 3-(4-(5-bromothiophen-2-yl)benzyl)-4-(4-(5-bromothiophen-2-yl)phenyl)-2-methylbutan-2-ol (7a)

[Chemical Formula 70]

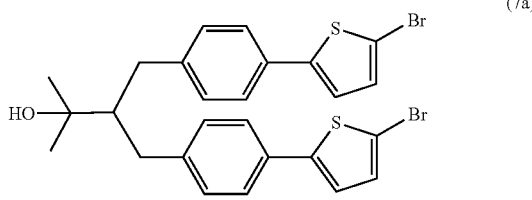

(7a)

A mixed liquid containing 2-methyl-3-(4-(thiophen-2-yl)benzyl)-4-(4-(thiophen-4-yl)phenyl)butan-2-ol (1.26 g, 3.0 mmol), N-bromosuccinimide (1.12 g, 6.3 mmol), methylene chloride (5.0 mL) and acetic acid (2.5 mL) was stirred for 6 hours, and water was then used to halt the reaction. The organic layer was separated from the mixed liquid, and the water layer was extracted with chloroform. The resulting organic layer was washed with a saturated aqueous solution of sodium hydrogen carbonate, and dried using anhydrous magnesium sulfate. Following filtering of the organic layer, the filtrate was concentrated under reduced pressure, and the resulting residue was purified by silica gel column chromatography (hexane:ethyl acetate=5:1), yielding the title compound (7a) (1.70 g, 2.94 mmol) as a colorless solid in a yield of 98%.

R$_f$: 0.48 (hexane:ethyl acetate/2:1)

$^1$H NMR (500 MHz, CDCl$_3$) δ 7.30 (d, 4H, J=8.0 Hz, Ar), 7.01 (d, 4H, J=8.0 Hz, Ar), 6.99 (d, 2H, J=4.0 Hz, Ar), 6.94 (d, 2H, J=4.0 Hz, Ar), 2.94 (dd, 2H, J=4.8, 14.3 Hz, CH$_2$Ar), 2.46 (dd, 21-1, J=7.8, 13.8 Hz, CH$_2$Ar), 2.21 to 2.14 (m, 1H, CHCH$_2$Ar), 1.29 (s, 6H, (CH$_3$)$_2$C).

IR (film) 3449, 2965, 2924, 2852, 1502, 1432, 1384, 1261, 1111, 977.7, 787.8, 671.1 cm$^{-1}$.

Example 43

Synthesis of ((3-(4-(5-bromothiophen-2-yl)benzyl)-4-(4-(5-bromothiophen-2-yl)phenyl)-2-methylbutan-2-yl)oxy)triethylsilane (7b)

[Chemical Formula 71]

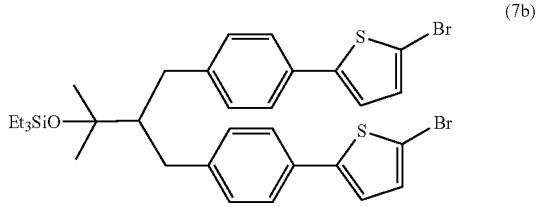

(7b)

Imidazole (245 mg, 3.6 mmol), triethylsilyl chloride (1.2 mL, 7.2 mmol) and N,N-dimethylformamide (10 mL) were added at 0° C. to 3-(4-(5-bromothiophen-2-yl)benzyl)-4-(4-(5-bromothiophen-2-yl)phenyl)-2-methylbutan-2-ol (1.15 g, 2.0 mmol). Following stirring of the resulting mixed liquid at room temperature for 12 hours, a saturated aqueous solution of ammonium chloride was added to halt the reaction. The organic layer was separated from the mixed liquid, and the water layer was extracted with ether. The resulting organic layer was washed with a saturated aqueous solution of sodium chloride, and dried using anhydrous magnesium sulfate. Following filtering of the organic layer, the filtrate was concentrated under reduced pressure, and the resulting residue was purified by silica gel column chromatography (hexane), yielding the title compound (7b) (1.35 g, 1.95 mmol) as a colorless solid in a yield of 98%.

$^1$H NMR (600 MHz, CDCl$_3$) δ 7.23 (d, 4H, J=8.0 Hz, Ar), 6.96 (d, 4H, J=4.0 Hz, Ar), 6.96 to 6.92 (m, 4H, Ar), 6.90 (d, 2H, J=4.0 Hz, Ar), 3.00 (dd, 2H, J=4.8, 14.3 Hz, CH$_2$Ar), 2.38 (dd, 2H, J=8.0, 14.5 Hz, CH$_2$Ar), 2.15 to 2.08 (m, 1H, CHCH$_2$Ar), 1.25 (s, 6H, (CH$_3$)$_2$C), 0.99 (t, J=7.8 Hz, 9H, (CH$_3$CH$_2$)$_3$Si), 0.62 (q, 6H, J=8.0 Hz, (CH$_3$CH$_2$)$_3$Si).

$^{13}$C NMR (CDCl$_3$, 150 MHz) δ 146.0, 142.5, 130.8, 130.7, 129.5, 125.2, 122.6, 110.7, 76.1, 54.8, 36.6, 28.1, 7.2, 6.9.

IR (film) 2952, 2873, 1504, 1434, 1206, 1144, 1041, 978.7, 788.7, 741.5, 672.1 cm$^{-1}$.

Example 44

Synthesis of Polymer Compound (11a)

[Chemical Formula 72]

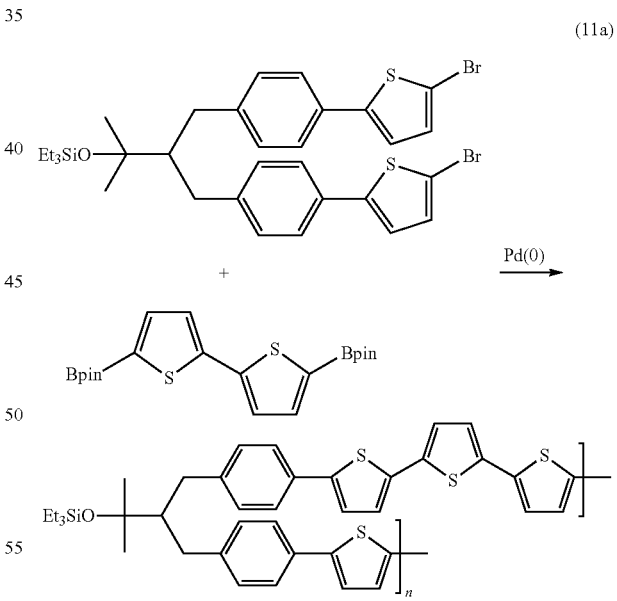

A mixed liquid of (3-(4-(5-bromothiophen-2-yl)benzyl)-4-(4-(5-bromothiophen-2-yl)phenyl)-2-methylbutan-2-yl)oxy)triethylsilane (346 mg, 0.50 mmol), 5,5'-bis(4,4,5,5-tetramethyl-1,3,2-dioxaborolan-2-yl)-2,2'-bithiophene (209 mg, 0.50 mmol), tri-n-octylmethylammonium chloride (45 mg, 0.10 mmol), a 2 M aqueous solution of sodium carbonate (1.0 mL) and tetrahydrofuran (2.3 mL) in a reaction container was deaerated, and the air inside the reaction container was replaced with argon. A solution containing tetrakistriphenylphosphinepalladium(0) (23 mg, 0.020 mmol) in tetrahydrofuran (1.0 mL) was added to the mixed liquid. Following stirring of the resulting mixed liquid at 80° C. for 3 days, the temperature was cooled to room temperature, and a saturated aqueous solution of sodium hydrogen carbonate was added to halt the reaction. The mixed liquid was extracted using chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into methanol, the polymer compound precipitated as a solid. This solid was collected by filtration, washed with ether, and then dried under reduced pressure, yielding the polymer compound (11a) (69.5 mg, 0.10 mmol) as a brown solid in a yield of 20%.

GPC (solvent: THF, standard: poly-styrene: $M_n$=2.78×10$^3$, $M_w$=3.12×10$^3$, $M_w/M_n$=1.12.

UV absorption spectra: $\lambda_{abs\ max}$ 400 nm (in $CH_2Cl_2$).
Emission spectra: $\lambda_{em\ max}$ 504 nm (in $CH_2Cl_2$).
$^1$H NMR (500 MHz, CDCl$_3$) δ 7.40 to 6.80 (br m, 16H per a repeated unit, Ar), 3.09 to 2.96 (br, 2H per a repeated unit, CH$_2$Ar), 2.45 to 2.30 (br, 2H per a repeated unit, CH$_2$Ar), 2.20 to 2.10 (br, 1H per a repeated unit, CHCH$_2$Ar), 1.35 to 1.20 (br, 6H per a repeated unit, (CH$_3$)$_2$C), 1.05 to 0.93 (br, 9H per a repeated unit, (CH$_3$CH$_2$)$_3$Si), 0.70 to 0.55 (br, 6H per a repeated unit, (CH$_3$CH$_2$)$_3$Si).
IR (film) 2949, 2872, 1598, 1513, 1456, 1382, 1364, 1177, 1141, 1011, 959.4, 821.5, 721.2, 545.8 cm$^{-1}$.

Example 45

Synthesis of Polymer Compound (11b)

[Chemical Formula 73]

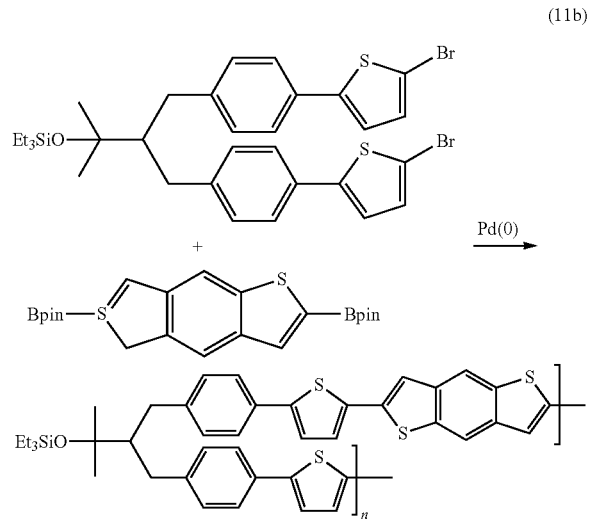

A mixed liquid of ((3-(4-(5-bromothiophen-2-yl)benzyl)-4-(4-(5-bromothiophen-2-yl)phenyl)-2-methylbutan-2-yl)oxy)triethylsilane (346 mg, 0.50 mmol), 2,6-bis(4,4,5,5-tetramethyl-1,3,2-dioxaborolan-2-yl)benzo[1,2-b:4,5-b']dithiophene (221 mg, 0.50 mmol), tri-n-octylmethylammonium chloride (45 mg, 0.10 mmol), a 2 M aqueous solution of sodium carbonate (1.0 mL) and tetrahydrofuran (2.3 mL) in a reaction container was deaerated, and the air inside the reaction container was replaced with argon. A solution containing tetrakistriphenylphosphinepalladium (0) (23 mg, 0.020 mmol) in tetrahydrofuran (1.0 mL) was added to the mixed liquid. Following stirring of the resulting mixed liquid at 80° C. for 3 days, the temperature was cooled to room temperature, and a saturated aqueous solution of sodium hydrogen carbonate was added to halt the reaction. The mixed liquid was extracted using chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into methanol, the polymer compound precipitated as a solid. This solid was collected by filtration, washed with ether, and then dried under reduced pressure, yielding the polymer compound (11b) (284 mg, 0.39 mmol) as a light green solid in a yield of 78%.

GPC (solvent: THF, standard: poly-styrene: $M_n$=3.22×10$^3$, $M_w$=4.99×10$^3$, $M_w/M_n$=1.55.

UV absorption spectra: $\lambda_{abs\ max}$ 269 nm (in $CH_2Cl_2$), 271 nm (film).
Emission spectra: $\lambda_{em\ max}$ 432 nm (in $CH_2Cl_2$), 448 nm (film).
$^1$H NMR (500 MHz, CDCl$_3$) δ 8.74 to 6.78 (br m, 16H per a repeated unit, Ar), 3.16 to 2.97 (br, 2H per a repeated unit, CH$_2$Ar), 2.46 to 2.29 (br, 2H per a repeated unit, CH$_2$Ar), 2.26 to 2.10 (br, 1H per a repeated unit, CHCH$_2$Ar), 1.40 to 1.19 (br, 6H per a repeated unit, (CH$_3$)$_2$C), 1.09 to 0.94 (br, 9H per a repeated unit, (CH$_3$CH$_2$)$_3$Si), 0.74 to 0.58 (br, 6H per a repeated unit, (CH$_3$CH$_2$)$_3$Si).
IR (film) 2949, 2872, 1598, 1513, 1456, 1382, 1364, 1177, 1141, 1011, 959.4, 821.5, 721.2, 545.8 cm$^{-1}$.

Example 46

Synthesis of 4-(4-bromobenzyl)-5-(4-bromophenyl)-3,3-dimethylpentan-1-ol (4i)

[Chemical Formula 74]

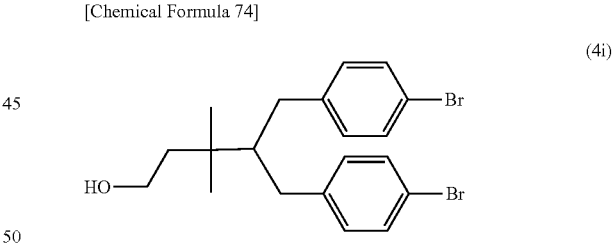

4,4'-(2-(2-methylbut-3-en-2-yl)propan-1,3-diyl)bis(bromobenzene) (1.229 g, 2.91 mmol) in a reaction container was deaerated, and the air inside the reaction container was replaced with argon. Tetrahydrofuran (20 mL) and a 0.4 M tetrahydrofuran solution of 9-borabicyclo[3.3.1]nonane (8 mL, 3.2 mmol) were then added to the container. The thus obtained mixed liquid was stirred at room temperature for 2 hours, and a 1 M aqueous solution of sodium hydroxide (11.6 mL) and a 35% solution of hydrogen peroxide (6.7 mL) were then added to the mixed liquid. The resulting mixed liquid was stirred overnight at room temperature, and a saturated aqueous solution of ammonium chloride was then added to halt the reaction. The organic layer was separated from the mixed liquid, and the water layer was extracted with diethyl ether. The thus obtained organic layer was washed with a saturated saline solution and then dried using anhydrous sodium sulfate. The organic layer was then filtered, the filtrate was concentrated under reduced pressure, and the resulting residue was purified by silica gel column chromatography (hexane:diethyl ether=3:1), yielding the title compound (4l) (1.15 g, 2.61 mmol) as a colorless liquid in a yield of 90%.

$^1$H NMR (CDCl$_3$, 600 MHz) δ 7.25 (d, 4H, J=8.4 Hz, Ar), 6.79 (d, 4H, J=8.4 Hz, Ar), 3.68 (t, 2H, J=7.2 Hz, OCH$_2$CH$_2$), 2.82 (dd, 2H, J=4.2, 14.0 Hz, CH$_2$Ar), 2.31 (dd, 2H, J=8.4, 14.0 Hz, CH$_2$Ar), 1.88 (m, 1H, CHCH$_2$Ar), 1.67 (t, 2H, J=7.2 Hz, OCH$_2$CH$_2$), 0.97 (s, 6H, C(CH$_3$)$_2$).

$^{13}$C NMR (CDCl$_3$, 150 MHz) δ 141.3, 131.1, 130.6, 119.3, 59.5, 51.7, 42.7, 36.4, 36.0, 25.7.

IR (neat) 3352, 2961, 1488, 1449, 1403, 1367, 1199, 1179, 1102, 1072, 1011, 983.5, 833.1, 795.5, 687.5 cm$^{-1}$.

Example 47

Synthesis of ((4-(4-bromobenzyl)-5-(4-bromophenyl)-3,3-dimethylpentyl)oxy)triisopropylsilane (4j)

[Chemical Formula 75]

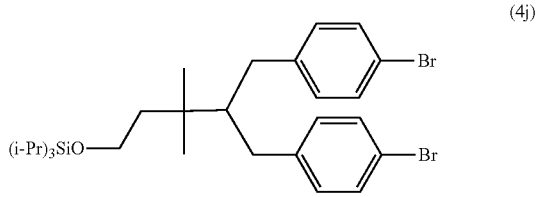

(4j)

A mixture of 4-(4-bromobenzyl)-5-(4-bromophenyl)-3,3-dimethylpentan-1-ol (0.974 g, 2.34 mmol) and 1,3-diaza-2,4-cyclopentadiene (0.351 g, 5.15 mmol) in a reaction container was deaerated, and the air inside the reaction container was replaced with argon. N,N-dimethylformamide (12 mL) and triisopropylsilyl chloride (0.68 g, 3.51 mmol) were then added to the mixed liquid. The thus obtained mixed liquid was stirred overnight at room temperature, and a sufficient amount of water was added to halt the reaction. The organic layer was separated from the mixed liquid, and the water layer was extracted with diethyl ether. The thus obtained organic layer was washed with a saturated saline solution and then dried using anhydrous magnesium sulfate. The organic layer was then filtered, the filtrate was concentrated under reduced pressure, and the resulting residue was purified by silica gel column chromatography (hexane:diethyl ether=50:1), yielding the title compound (4j) (1.16 g, 1.94 mmol) as a light yellow liquid in a yield of 83%.

$^1$H NMR (CDCl$_3$, 600 MHz) δ 7.24 (d, 4H, J=8.4 Hz, Ar), 6.78 (d, 4H, J=8.4 Hz, Ar), 3.73 (t, 2H, J=7.2 Hz, OCH$_2$CH$_2$), 2.83 (dd, 2H, J=8.4, 14.0 Hz, CH$_2$Ar), 2.30 (dd, 2H, J=4.8, 14.0 Hz, CH$_2$Ar), 1.84 (m, 1H, CHCH$_2$Ar), 1.65 (t, 2H, J=7.2 Hz, OCH$_2$CH$_2$), 1.06 (21H, ((CH$_3$)$_2$CH)$_3$Si), 0.96 (s, 6H, (CH$_3$)$_2$C).

$^{13}$C NMR (CDCl$_3$, 150 MHz) δ 141.4, 131.1, 130.6, 119.2, 60.0, 52.2, 42.6, 36.3, 36.1, 25.7, 18.1, 12.0.

IR (neat) 2961, 2941, 2865, 1488, 1464, 1404, 1260, 1097, 1073, 1012, 882.3, 801.3, 681.7, 658.6 cm$^{-1}$.

Example 48

Synthesis of poly-[CH$_2$—CH(C(CH$_3$)$_2$CH$_2$CH$_2$OSi (CH(CH$_3$)$_2$)$_3$—CH$_2$-1,4-(phenylene)-2,5-(thiophenylene)-2,5-(thiophenylene)-1,4-(phenylene)] (3l)

[Chemical Formula 76]

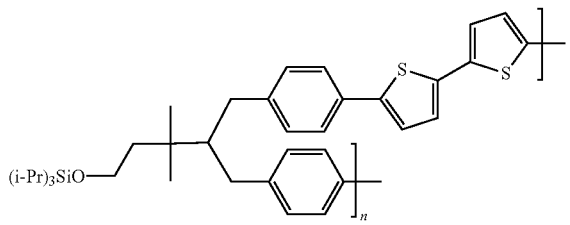

(3l)

A mixed liquid of ((4-(4-bromobenzyl)-5-(4-bromophenyl)-3,3-dimethylpentyl)oxy)triisopropylsilane (0.300 g, 0.5 mmol), 5,5'-bis(4,4,5,5-tetramethyl-1,3,2-dioxaborolan-2-yl)-2,2'-bithiophene (0.209 g, 0.5 mmol), tri-n-octylmethylammonium chloride (40 mg, 0.1 mmol), a 2 M aqueous solution of sodium carbonate (1.0 mL) and tetrahydrofuran (2 mL) in a reaction container was deaerated, and the air inside the reaction container was replaced with argon. A solution containing tetrakistriphenylphosphinepalladium(0) (35 mg, 0.03 mmol) in tetrahydrofuran (1.0 mL) was added to the mixed liquid. Following stirring of the resulting mixed liquid at 80° C. for 3 days, the temperature was cooled to room temperature, and a saturated aqueous solution of sodium hydrogen carbonate was added to halt the reaction. The mixed liquid was extracted with chloroform, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into methanol, the polymer compound precipitated as a solid. This solid was collected by filtration, washed with methanol, and then dried under reduced pressure, yielding the title polymer compound (3l) (0.290 g, 0.48 mmol) as a dark brown solid in a yield of 96%.

GPC (solvent: THF, standard: poly-styrene: $M_n$=4.37×10$^3$, $M_w$=6.82×10$^3$, $M_w/M_n$=1.56.

$^1$H NMR (CDCl$_3$, 600 MHz) δ 7.43 to 6.64 (br m, 12H per a repeated unit, Ar), 3.88 to 3.67 (br, 2H per a repeated unit, OCH$_2$CH$_2$), 3.03 to 2.80 (br, 2H per a repeated unit, CH$_2$Ar), 2.46 to 2.25 (br, 2H per a repeated unit, CH$_2$Ar), 2.02 to 1.89 (br, 1H per a repeated unit, CHCH$_2$Ar), 1.76 to 1.59 (br, 2H per a repeated unit, OCH$_2$CH$_2$), 1.21 to 0.90 (br m, 27H per a repeated unit, (CH$_3$)$_2$CH)$_3$Si and (CH$_3$)$_2$C).

$^{13}$C NMR (CDCl$_3$, 150 MHz) δ 149.2, 142.9, 141.9, 136.2, 131.2, 131.0, 129.4, 127.8, 125.2, 124.2, 123.2, 123.1, 60.1, 52.2, 42.6, 36.5, 36.2, 25.8, 18.1, 12.0, 1.0.

IR (KBr) 2962, 2939, 2864, 1497, 1462, 1444, 1261, 1095, 1021, 881.3, 798.4, 681.7, 658.6 cm$^{-1}$.

UV absorption: $\lambda_{Abs\ max}$=368 nm (10$^{-5}$ M in CH$_2$Cl$_2$)

Fluorescence emission: $\lambda_{em\ max}$=463 nm ($10^{-6}$M in $CH_2Cl_2$)

Example 49

Synthesis of poly-[$CH_2$—$CH(C(CH_3)_2CH_2CH_2OSi(CH(CH_3)_2)_3$—$CH_2$-1,4-(phenylene)-(E)-1,2-(ethenylene)-1,4-(phenylene)-(E)-1,2-(ethenylene)) (3m)

[Chemical Formula 77]

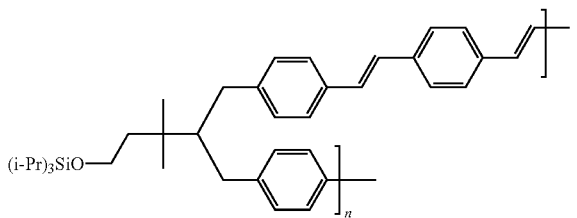

(3m)

A mixture of ((4-(4-bromobenzyl)-5-(4-bromophenyl)-3,3-dimethylpentyl)oxy)triisopropylsilane (0.210 g, 0.35 mmol), palladium(0) acetate (3.2 mg, 0.014 mmol), N,N-dimethyl-β-alanine (2.2 mg, 0.014 mmol) and potassium carbonate (195 mg, 1.4 mmol) in a reaction container was deaerated, and the air inside the reaction container was replaced with argon. A solution containing 1,4-divinylbenzene (45.8 mg, 0.35 mmol) in N-methyl-2-pyrrolidone (3.5 mL) was then added to the mixed liquid. The thus obtained mixed liquid was stirred at 130° C. for 3 days, and following cooling to room temperature, a saturated aqueous solution of sodium hydrogen carbonate was added to halt the reaction. The mixed liquid was extracted with methylene chloride, and the thus obtained organic layer was washed with water, dried using anhydrous sodium sulfate, and filtered. The filtrate was concentrated under reduced pressure, and the resulting residue was dissolved in a small amount of chloroform. When the thus obtained solution was poured into methanol, the polymer compound precipitated as a solid. This solid was collected by filtration, washed with methanol, and then dried under reduced pressure, yielding the title polymer compound (3m) (27 mg) as a yellow-brown solid in a yield of 13%.

GPC (solvent: THF, standard: poly-styrene: $M_n$=9.12×$10^3$, $M_w$=1.12×$10^4$, $M_w/M_n$=1.23.

$^1$H NMR (CDCl$_3$, 600 MHz) δ 7.51 to 6.48 (br m, 16H per a repeated unit, Ar and CH=CH), 3.83 to 3.64 (br, 2H per a repeated unit, OCH$_2$CH$_2$), 2.98 to 2.78 (br, 2H per a repeated unit, CH$_2$Ar), 2.49 to 2.29 (br, 2H per a repeated unit, CH$_2$Ar), 2.01 to 1.86 (br, 1H per a repeated unit, CH$_2$Ar), 1.77 to 1.51 (br, 2H per a repeated unit, OCH$_2$CH$_2$), 1.17 to 0.86 (br m, 27H per a repeated unit, (CH$_3$)$_2$CH)$_3$Si and (CH$_3$)$_2$C).

IR (neat) 2961, 2864, 1487, 1463, 1366, 1260, 1094, 1016, 881.3, 800.3, 736.7, 682.7 cm$^{-1}$.

UV absorption: $\lambda_{abs\ max}$=255 nm, ($10^{-5}$ M in $CH_2Cl_2$)

Fluorescence emission: $\lambda_{em\ max}$=423 nm ($10^{-6}$M in $CH_2Cl_2$)

Example 50

Synthesis of ethyl 2,2-bis(4-bromobenzyl)-3-oxobutanoate (4k)

[Chemical Formula 78]

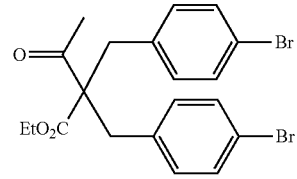

(4k)

Ethyl acetoacetate (0.632 mL, 5 mmol) was added to a solution containing NaH (0.493 g, 11.25 mmol) in DMF (5 mL), and the resulting mixture was stirred at 0° C. for 30 minutes. 1-bromo-4-(bromomethyl)benzene (2.788 g, 11.15 mmol) was added to the mixed liquid, and the resulting mixture was stirred at room temperature for 12 hours. The mixed liquid was then poured into a saturated aqueous solution of NaHCO$_3$, and extracted with ethyl acetate. The organic layer was washed with a saturated saline solution, dried using MgSO$_4$, and then concentrated under reduced pressure, yielding the title compound (4k) in a yield of 90%.

$^1$H NMR (600 MHz, CDCl$_3$) δ 7.38 (d, J=8.4 Hz, 4H), 6.97 (d, J=8.4, 4H), 4.11 (q, J=6.6 Hz, 2H), 3.14 and 3.10 (2d, J=14.4 and 14.4 Hz, each 2H), 1.97 (s, 3H), 1.18 (t, J=6.6 Hz, 3H).

$^{13}$C NMR (150 MHz, CDCl$_3$) δ 205.1, 171.3, 135.1, 131.7, 131.4, 121.0, 65.7, 61.5, 39.3, 29.1, 13.8.

Example 51

Synthesis of 3-(4-bromobenzyl)-4-(4-bromophenyl)butan-2-one (41)

A mixed liquid containing LiCl (0.175 g, 4 mmol), ethyl 2,2-bis(4-bromobenzyl)-3-oxobutanoate (0.94 g, 2 mmol) and H$_2$O (0.036 mL) in DMF (4 mL) was stirred under heating at 120° C. for 48 hours. The mixed liquid was then cooled to room temperature, water (10 mL) was added, and the resulting mixture was extracted with ethyl acetate. The resulting organic layer was washed with a saturated saline solution and then dried using MgSO$_4$. The organic layer was concentrated under reduced pressure, and then purified using silica gel column chromatography, yielding the title compound (41) in a yield of 52%.

$^1$H NMR (500 MHz, CDCl$_3$) δ 7.39 (d, J=8.0 Hz, 4H), 7.00 (d, J=8.0, 4H), 3.10 to 3.03 (m, 1H), 2.87 (dd, J=8.5, 13.5 Hz, 2H), 2.64 (d, J=5.5, 13.5 Hz, 2H), 1.80 (s, 3H).

$^{13}$C NMR (125 MHz, CDCl$_3$) δ 211.1, 138.0, 131.6, 130.5, 120.3, 56.0, 37.3, 31.6.

Example 52

Synthesis of 4,4'-(2-(4-chlorobut-2-en-2-yl)propane-1,3-diyl)bis(bromobenzene) (4m)

[Chemical Formula 79]

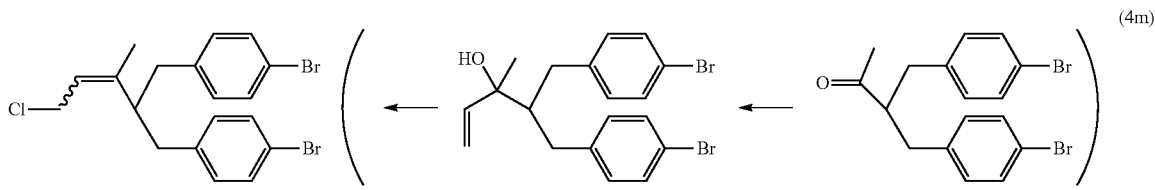

Vinylmagnesium bromide (5.7 mL, 0.35 M in THF, 2.0 mmol) was added at 0° C. to a solution containing 3-(4-bromobenzyl)-4-(4-bromophenyl)butan-2-one (396 mg, 1.0 mmol) in THF (5 mL), forming a mixed liquid. Following stirring of the mixed liquid for 2 hours, a saturated aqueous solution of ammonium chloride was added, and the resulting mixture was extracted with ethyl acetate. The organic layer was washed with a saturated saline solution, and then dried using $Na_2SO_4$. The organic layer was concentrated under reduced pressure, yielding a crude product of 4-(4-bromobenzyl)-5-(4-bromophenyl)-3-methylpent-1-en-3-ol.

Methylene chloride (5 mL) was added to this crude product, and following cooling to 0° C., $BCl_3$ (1.3 mL, 1.0 M in heptane, 1.3 mmol) was added. Following stirring for 10 minutes, a saturated aqueous solution of $NaHCO_3$ was added, and the mixture was extracted with ethyl acetate. The resulting organic layer was washed with a saturated saline solution, and dried using $MgSO_4$. The organic layer was then concentrated under reduced pressure, and the resulting crude product was purified by silica gel column chromatography, yielding the title compound (4m) (trans/cis mixture) in a two-stage yield of 82%.

$^1$H NMR (500 MHz, $CDCl_3$) δ 7.37 (d, J=8.0 Hz, 4H), 6.95 (d, J=8.0 Hz, 4H), 5.22, (t, J=8.0 Hz, 1H), 3.93 (d, J=8.0 Hz, 2H), 2.70 to 2.48 (m, 5H), 1.62 (s, 3H). $R_f$ 0.74 (TLC, Merk 2554, hexane/$Et_2O$=1:1 (v/v))

Example 53

Synthesis of 4,4'-(2-(2-methylbut-3-en-2-yl)propane-1,3-diyl)bis(bromobenzene) (4n)

[Chemical Formula 80]

MeMgI (3.21 mL, 1.4 M in ether, 4.5 mmol) was added at 0° C. to a mixed liquid containing (1,3-dimesityl-1H-imidazol-2(3H)-ylidene)copper(I)chloride (244 mg, 0.60 mmol) in ether (5 mL), and the resulting mixture was stirred for 10 minutes. A solution containing 4,4'-(2-(4-chlorobut-2-en-2-yl)propane-1,3-diyl)bis(bromobenzene) (1.33 g, 3.0 mmol) in ether (4 mL) was then added, and the resulting mixed liquid was stirred at 0° C. for 12 hours. A saturated aqueous solution of ammonium chloride was added to the mixed liquid, and the mixture was extracted with ether. The thus obtained organic layer was washed with a saturated saline solution, and dried using $MgSO_4$. The organic layer was then concentrated under reduced pressure, and the resulting residue was purified by silica gel column chromatography, yielding the title compound (4n) (1.23 g) in a yield of 97%.

$^1$H NMR (600 MHz, $CDCl_3$) δ 7.23 (d, J=8.4 Hz, 4H), 6.76 (d, J=8.4 Hz, 4H), 5.84 (dd, J=10.2, 17.4 Hz, 1H), 5.03 to 4.99 (m, 2H), 2.80 (dd, J=4.2, 13.8 Hz, 2H), 2.27 (dd, J=8.4, 13.8 Hz, 2H), 1.89 to 1.83 (m, 1H), 1.04 (s, 6H).

$^{13}$C NMR (150 MHz, $CDCl_3$) δ 147.4, 141.3, 131.0, 130.7, 119.2, 111.8, 52.0, 40.9, 36.5, 24.7.

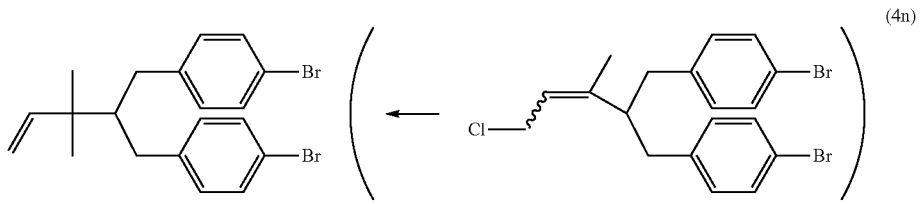

Example 54

Synthesis of Compound (4o)

[Chemcial Formula 81]

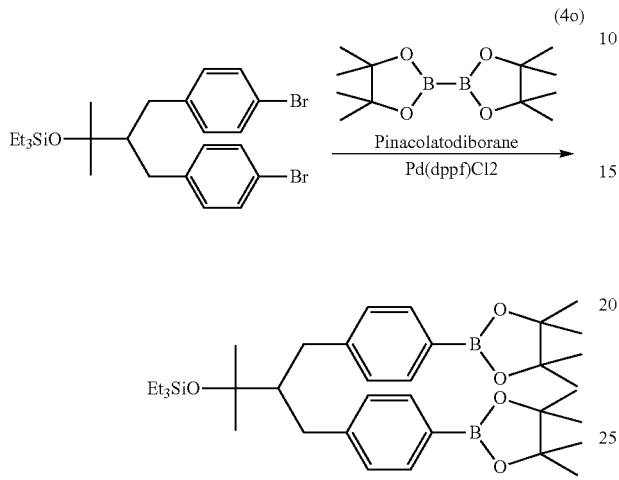

Under a nitrogen atmosphere, a 500 mL four-neck flask was charged with the compound (4b) (11.00 g, 20.9 mmol) obtained in the example 17, bis(pinacolato)diboron (12.13 g, 47.8 mmol) and potassium acetate (14.22 g, 145 mmol), DME (293 mL) was added, and the resulting mixture was deaerated with nitrogen for 30 minutes. Pd(dppf)Cl$_2$—CH$_2$Cl$_2$ (1.51 g, 1.85 mmol) was then added to the flask, and the resulting mixture was stirred under heat at an internal temperature of 87° C. for 4 hours. Following completion of the reaction, the reaction mixture was poured into water (200 mL), and the resulting mixture was extracted with ethyl acetate (200 mL×3 repetitions). The organic layer was washed with a saturated saline solution (200 mL×1 repetition), and then dried using magnesium sulfate (20g). The solvent was removed from the organic layer under reduced pressure, and a silica gel 60N from Kanto Chemical Co., Inc. was used to purify the residue by silica gel column chromatography (hexane→hexane/ethyl acetate=10/1), yielding a light yellow solid (10.21 g). Recrystallization from ethanol (300 mL) yielded 7.00 g (yield: 54%) of the compound (4o) as a white solid.

Example 55

Synthesis of Polymer Compound (6a)

(Preparation of Pd Catalyst)

In a glove box under a nitrogen atmosphere at room temperature, tris(dibenzylideneacetone)dipalladium (73.2 g, 80 mop was weighed into a sample tube, anisole (15 mL) was added, and the mixture was stirred for 30 minutes. In a similar manner, tri-tert-butylphosphine (129.6 g, 640 μmol) was weighed into a sample tube, anisole (5 mL) was added, and the mixture was stirred for 5 minutes. The two solutions were then mixed and stirred at room temperature for 30 minutes to obtain a catalyst.

[Chemical Formula 82]

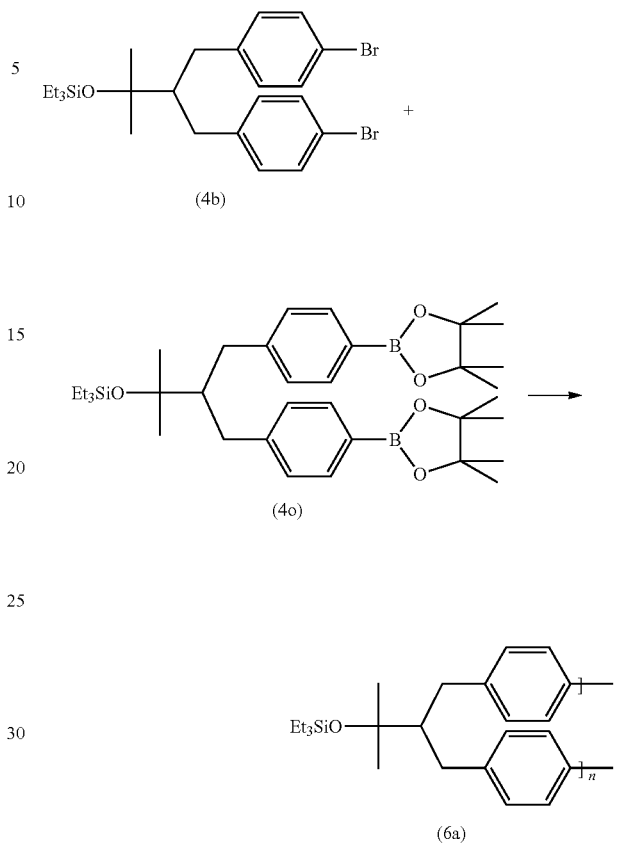

A three-neck round-bottom flask was charged with the compound (4b) (1.8 mmol) obtained in the example 17, the compound (4o) (1.8 mmol) obtained in the example 54 and anisole (20 mL), and the previously prepared Pd catalyst solution (2.5 mL) was then added. The thus obtained mixed liquid was stirred for 30 minutes, and a 10% aqueous solution of tetraethylammonium hydroxide (12 mL) was then added. All of the solvents were thoroughly deaerated by nitrogen bubbling for at least 30 minutes prior to use. The mixed liquid was then heated under reflux for 2 hours. All of the operations up until this point were performed under a stream of nitrogen.

Following completion of the reaction, the mixed liquid was washed with water and then poured into a mixture of methanol and water (9:1). The precipitate that formed was colleted by suction filtration, and washed with methanol-water (9:1). The thus obtained precipitate was dissolved in toluene, and then re-precipitated from methanol. The precipitate was once again collected by suction filtration and dissolved in toluene, triphenylphosphine (polymer-bound on styrene-divinylbenzene copolymer) (manufactured by Strem Chemicals Inc, 200 mg per 100 mg of the polymer) was added, and the resulting mixture was stirred overnight. Following completion of the stirring, the triphenylphosphine (polymer-bound on styrene-divinylbenzene copolymer) and other insoluble substances were removed by filtration, and the filtrate was concentrated using a rotary evaporator. The residue was then dissolved in toluene, and re-precipitated from methanol-acetone (8:3). The thus obtained precipitate was collected by suction filtration and washed with methanol-acetone (8:3). The resulting precipitate was then vacuum dried, yielding the polymer compound (6a) as a white solid.

GPC (solvent: THF, standard: poly-styrene: $M_w$=10,200, $M_w/M_n$=1.60.

Example 56

Synthesis of Polymer Compound (3k)

[Chemical Formula 83]

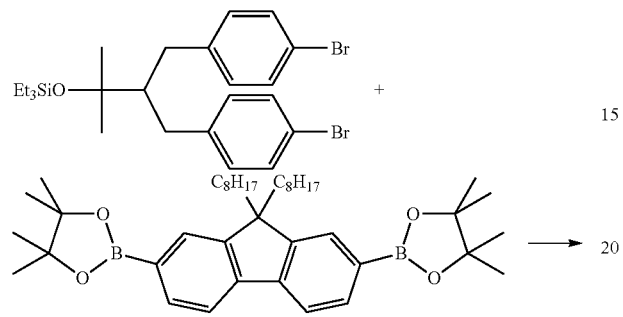

(3k)

With the exception of replacing the compound (4o) with 2,7-bis(4,4,5,5-tetramethyl-1,3,2-dioxaborolan-2-yl)-9,9-di-n-octylfluorene, the polymer compound (3k) was synthesized in the same manner as that described for the example 55.

GPC (solvent: THF, standard: poly-styrene: $M_w$=17,800, $M_w/M_n$=1.7.

Example 57

Synthesis of Polymer Compound (6b)

[Chemical Formula 84]

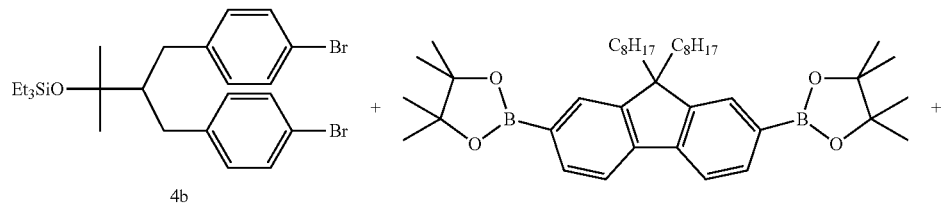

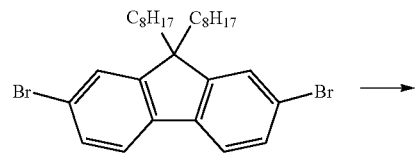

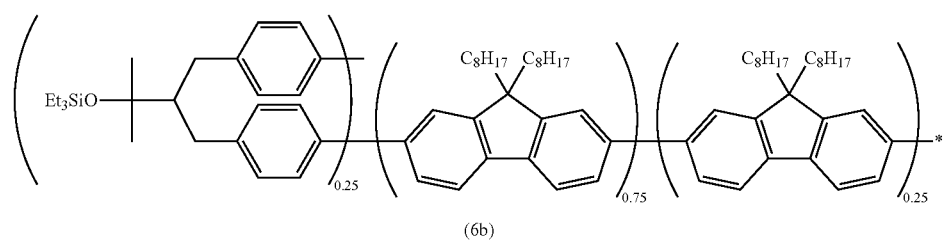

(6b)

With the exceptions of using the compound (4b) (0.9 mmol) obtained in the example 17, 2,7-bis(4,4,5,5-tetramethyl-1,3,2-dioxaborolan-2-yl)-9,9-di-n-octylfluorene (1.8 mmol) and 2,7-dibromo-9,9-di-n-octylfluorene (0.9 mmol), the polymer compound (6b) was synthesized in the same manner as that described for the example 55.

GPC (solvent: THF, standard: poly-styrene: $M_w$=23,200, $M_w/M_n$=1.72.

INDUSTRIAL APPLICABILITY

The compound and polymer compound of the present invention are able to adopt a stacked structure in which the π-conjugated groups are stacked upon each other. By using the reactive compound of the present invention and the methods of producing the above compound and polymer compound, the compound and polymer compound of the present invention can be obtained with good efficiency. As a result of adopting a stacked structure, the compound and polymer compound of the present invention exhibit unique properties, making them useful as materials for organic devices.

The invention claimed is:

1. A polymer compound represented by a general formula 3 shown below:

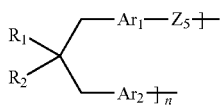

Formula 3 wherein each of $R_1$ and $R_2$ independently represents a group selected from the group consisting of a hydrogen atom, aliphatic substituents composed of C and H, aromatic substituents composed of C and H, aliphatic substituents composed of C, H and X, wherein X represents a hetero atom, and aromatic substituents composed of C, H and X, wherein X represents a hetero atom, $Z_5$ represents a group selected from the group consisting of divalent aromatic rings composed of C and H, divalent aromatic rings composed of C, H and X, wherein X represents a hetero atom, divalent groups containing an aromatic ring and a double-bonded and/or triple-bonded conjugated structure composed of C and H, and divalent groups containing a double-bonded and/or triple-bonded conjugated structure composed of C, H and X, wherein X represents a hetero atom, each of $Ar_1$ and $Ar_2$ independently represents a group selected from the group consisting of divalent aromatic rings composed of C and H, and divalent aromatic rings composed of C, H and X (wherein X represents a hetero atom), n represents an integer of 2 or greater, and $R_1$ is a hydrogen atom, and $R_2$ is a carbon atom having not more than 2 hydrogen atoms bonded thereto.

2. The polymer compound according to claim 1, wherein the number-average molecular weight is within a range from 1,000 to 500,000.

3. The polymer compound according to claim 1, wherein the number-average molecular weight is within a range from 2,500 to 100,000.

4. The polymer compound according to claim 1, wherein $R_2$ is carbon atom having not more than 1 hydrogen atom bonded thereto.

5. The polymer compound according to claim 1, wherein two or more of the aromatic rings within the polymer compound adopt a stacked structure.

6. The polymer compound according to claim 1, wherein an emission wavelength of the polymer compound differs from emission wavelength for stand-alone structure of $Z_5$, $Ar_1$, or $Ar_2$.

7. A composition comprising the polymer compound according to claim 1.

8. An organic device comprising the polymer compound according to claim 1.

* * * * *